US011306118B2

(12) United States Patent
Fernie et al.

(10) Patent No.: US 11,306,118 B2
(45) Date of Patent: Apr. 19, 2022

(54) UV-B ABSORBING COMPOUNDS ISOLATED FROM PLANTS

(71) Applicant: MAX-PLANCK-GESELLSCHAFT ZUR FÖRDERUNG DER WISSENSCHAFTEN E.V., Munich (DE)

(72) Inventors: Alisdair R. Fernie, Werder (DE); Takayuki Tohge, Berlin (DE); Regina Wendenburg, Berlin (DE); Hirofumi Ishihara, Golm-Potsdam (DE); Ronan Sulpice, County Galway (IE); Mark Stitt, Potsdam (DE)

(73) Assignee: Max-Planck-Gesellschaft zur Förderung der Wissenschaften E.V., Munich (DE)

( * ) Notice: Subject to any disclaimer, the term of this patent is extended or adjusted under 35 U.S.C. 154(b) by 259 days.

(21) Appl. No.: 16/592,975

(22) Filed: Oct. 4, 2019

(65) Prior Publication Data
US 2020/0079812 A1 Mar. 12, 2020

Related U.S. Application Data

(62) Division of application No. 15/580,089, filed as application No. PCT/EP2016/063085 on Jun. 8, 2016, now abandoned.

(30) Foreign Application Priority Data

Jun. 9, 2015 (EP) ..................... 15171291

(51) Int. Cl.
| | |
|---|---|
| C12N 9/10 | (2006.01) |
| C12N 15/82 | (2006.01) |
| C07H 17/07 | (2006.01) |
| C12Q 1/68 | (2018.01) |
| C07H 21/04 | (2006.01) |
| C12Q 1/6895 | (2018.01) |
| A61K 8/60 | (2006.01) |
| A61Q 17/04 | (2006.01) |

(52) U.S. Cl.
CPC .............. *C07H 17/07* (2013.01); *A61K 8/60* (2013.01); *A61Q 17/04* (2013.01); *C07H 21/04* (2013.01); *C12N 9/1029* (2013.01); *C12N 15/8271* (2013.01); *C12Q 1/68* (2013.01); *C12Q 1/6895* (2013.01); *C12Q 2600/13* (2013.01)

(58) Field of Classification Search
None
See application file for complete search history.

(56) References Cited

PUBLICATIONS

Keskin et al., 2004, A new, structurally nonredundant, diverse data set of protein-protein interfaces and its implications, Protein Science 13: 1043-1055.*

Guo et al., 2004, Protein tolerance to random amino acid change, Proceedings of the National Academy of Sciences USA 101: 9205-9210.*

Thornton et al., 2000, From structure to function: approaches and limitations, Nature Structural Biology, structural genomic supplement, Nov. 2000: 991-994.*

*Arabidopsis thaliana* locus AT2G22960 information, available online at https://www.arabidopsis.org/servlets/TairObject?type=locus&name=At2g22960, accessed on Aug. 16, 2021.*

Korn et al., "Heterosis in the freezing tolerance, and sugar and flavonoid contents of crosses between *Arabidopsis thaliana* accessions of widely varying freezing tolerance" Plant, Cell and Environment (2008) 31, 813-827.

Matsuda et al. "Mass spectra-based framework for automated structural elucidation of metabolome data to explore phytochemical diversity" Frontiers in Plant Science (2011) vol. 2, Article 40.

Stobiecki et al. "Profiling of phenolic glycosidic conjugates in leaves of *Arabidopsis thaliana* using LC/MS" (2006) Metabolomics, vol. 2, No. 4, 197-219.

Dixon et al. "Stress-Induced Phenylpropanoid Metabolism" (1995) The Plant Cell, vol. 7, 1085-1097.

Lois et al. "Severe sensitivity to ultraviolet radiation in an *Arabidopsis* deficient in flavonoid accumulation II. Mechanisms of UV-resistance in *Arabidopsis*" Planta (1994) 194:504-509.

Chapple et al. "An *Arabidopsis* Mutant Defective in the General Phenylpropanoid Pathway" (1992) The Plant Cell, vol. 4, 1413-1424.

Chapple "Genetic characterization of secondary metabolism in *Arabidopsis*" (1994) Genetic Engineering of Plant Secondary Metabolism, Chapter 10, Plenum Press, New York.

Dosimetry description, p. 381 extracted from From Dermatology, Otto Braun-Falco, Gerd Plewig, Helmut H. Wolff, Richard K. Winkelmann, Springer Science & Business Media, Nov. 11, 2013, 1235 Seiten.

* cited by examiner

*Primary Examiner* — Bratislav Stankovic
(74) *Attorney, Agent, or Firm* — Kowert, Hood, Munyon, Rankin & Goetzel, P.C.; Gareth M. Sampson

(57) ABSTRACT

The present invention relates to compounds according to general formula (I) with enhanced absorption of UV-B irradiation. The present invention also relates to an UV-B tolerant plant and a method for enhanced production of compounds according to general formula (I) in a plant or plant cell. Furthermore, the invention relates to a nucleic acid sequence SEQ-ID No. 1 encoding FPT2 catalyzing the production of compounds according to general formula (I). The invention further relates to compositions comprising compounds according to general formula (I). Furthermore, the invention relates to a method of conferring UV-B tolerance to a plant as well as an UV-B tolerant plant comprising the nucleic acid sequence SEQ-ID No. 1 encoding FPT2 catalyzing the production of compounds according to general formula (I).

7 Claims, 12 Drawing Sheets
Specification includes a Sequence Listing.

A.

SEQUENCE LISTING

<160> NUMBER OF SEQ ID NOS: 22

<210> SEQ ID NO 1
<211> LENGTH: 1305
<212> TYPE: DNA
<213> ORGANISM: Artificial Sequence

```
<220> FEATURE:
<223> OTHER INFORMATION: cDNA of C24 FPT2

<400> SEQUENCE: 1
atgagaactt tttcacccaa gttgctgctt cttcttttac ttgttttaag acatcatgct      60
gaatctggct ctatcgtcaa gtttcttccc ggttttgaag ccctcttcc tttcgaactt      120
gaaaccgggt acatcggtat tggtgaagaa gaagaactgc aatcgtttta ctatttcatt      180
aagtctgaga agaatccaaa agaagatcct cttcttcttt ggatatctgg aggacctggt      240
tgctcttcta tttctgctct tcttttgag aatggacctg tggctctaaa gttcgaggtt       300
tacaatgaaa ctctccctta tttggtctct actacatatt catggaccaa gatgacgaac      360
gtattattct tggatcagcc tattggagtt ggcttctcct acaaaagaac tccaaatctt      420
gataaatcga gtgacacaat agaagtattg cggatatacg aatttcttca gaagtggcta      480
ggtgaacatc ctgagttttt ctccaacact ttttacgtag gaggagattc ttattccggt      540
aagattgttc cagctatcgt tgataaaatc tcacaagaaa attatttgtg ctgcaaacct      600
ccaataaatc ttcagggtta tgttctcgga aacccaataa caaatttgga atctgattct      660
aactatcgta ttccatatgc tcatggaatg gcattaattt ctgatgagct ctacgaatcc      720
ctgaagagaa actgcaaagg aagatataaa accgtggatc catctaacaa aaaatgtttg      780
aaacttgttg aaaaatacaa taagtgttct gataaaatat ttagaaact aatattatta       840
ccacagtgtg atgaaagatc tccactctgc tggggctacc acagtacact agctaaatat      900
tgggccaatg acgagagggt acgtgaagct cttcaaataa gaaagggaag tataggaaaa      960
tggatacgat gtaatacgaa tatacattac ggtgacgaca ttattagcag cataccatat     1020
catatgaata acagcatcaa cggataccga tctctcattt acagtggtga tcacgatatg     1080
gaggtaccct tccttgcaac tgaagcttgg ataagatctc tcaattatcc tattattgat     1140
gattggaggc cttggataat aaacaatcag atttcaggat acacgatgac ctatgccaat     1200
aagatgacat atgctactat caagggaggt ggacacactg cagagtataa accagcggag     1260
agctttatca tgttccaacg atggatcagt ggccagtctc tgtaa                   1305

<210> SEQ ID NO 2
<211> LENGTH: 434
<212> TYPE: PRT
<213> ORGANISM: Arabidopsis thaliana
<220> FEATURE:
<221> NAME/KEY: MISC_FEATURE
<222> LOCATION: (1)..(434)
<223> OTHER INFORMATION: amino acid sequence coded by SEQ-ID No. 1

<400> SEQUENCE: 2

Met Arg Thr Phe Ser Pro Lys Leu Leu Leu Leu Leu Val Leu
1               5                  10                  15

Arg His His Ala Glu Ser Gly Ser Ile Val Lys Phe Leu Pro Gly Phe
                20                  25                  30

Glu Gly Pro Leu Pro Phe Glu Leu Glu Thr Gly Tyr Ile Gly Ile Gly
            35                  40                  45

Glu Glu Glu Glu Leu Gln Ser Phe Tyr Tyr Phe Ile Lys Ser Glu Lys
        50                  55                  60

Asn Pro Lys Glu Asp Pro Leu Leu Leu Trp Ile Ser Gly Gly Pro Gly
65                  70                  75                  80

Cys Ser Ser Ile Ser Ala Leu Leu Phe Glu Asn Gly Pro Val Ala Leu
                85                  90                  95
```

```
Lys Phe Glu Val Tyr Asn Glu Thr Leu Pro Tyr Leu Val Ser Thr Thr
                100                 105                 110

Tyr Ser Trp Thr Lys Met Thr Asn Val Leu Phe Leu Asp Gln Pro Ile
            115                 120                 125

Gly Val Gly Phe Ser Tyr Lys Arg Thr Pro Asn Leu Asp Lys Ser Ser
        130                 135                 140

Asp Thr Ile Glu Val Leu Arg Ile Tyr Glu Phe Leu Gln Lys Trp Leu
145                 150                 155                 160

Gly Glu His Pro Glu Phe Phe Ser Asn Thr Phe Tyr Val Gly Gly Asp
                165                 170                 175

Ser Tyr Ser Gly Lys Ile Val Pro Ala Ile Val Asp Lys Ile Ser Gln
            180                 185                 190

Glu Asn Tyr Leu Cys Cys Lys Pro Pro Ile Asn Leu Gln Gly Tyr Val
        195                 200                 205

Leu Gly Asn Pro Ile Thr Asn Leu Glu Ser Asp Ser Asn Tyr Arg Ile
210                 215                 220

Pro Tyr Ala His Gly Met Ala Leu Ile Ser Asp Glu Leu Tyr Glu Ser
225                 230                 235                 240

Leu Lys Arg Asn Cys Lys Gly Arg Tyr Lys Thr Val Asp Pro Ser Asn
                245                 250                 255

Lys Lys Cys Leu Lys Leu Val Glu Lys Tyr Asn Lys Cys Ser Asp Lys
            260                 265                 270

Ile Phe Arg Glu Leu Ile Leu Leu Pro Gln Cys Asp Glu Arg Ser Pro
        275                 280                 285

Leu Cys Trp Gly Tyr His Ser Thr Leu Ala Lys Tyr Trp Ala Asn Asp
290                 295                 300

Glu Arg Val Arg Glu Ala Leu Gln Ile Arg Lys Gly Ser Ile Gly Lys
305                 310                 315                 320

Trp Ile Arg Cys Asn Thr Asn Ile His Tyr Gly Asp Asp Ile Ile Ser
                325                 330                 335

Ser Ile Pro Tyr His Met Asn Asn Ser Ile Asn Gly Tyr Arg Ser Leu
            340                 345                 350

Ile Tyr Ser Gly Asp His Asp Met Glu Val Pro Phe Leu Ala Thr Glu
        355                 360                 365

Ala Trp Ile Arg Ser Leu Asn Tyr Pro Ile Ile Asp Asp Trp Arg Pro
370                 375                 380

Trp Ile Ile Asn Asn Gln Ile Ser Gly Tyr Thr Met Thr Tyr Ala Asn
385                 390                 395                 400

Lys Met Thr Tyr Ala Thr Ile Lys Gly Gly His Thr Ala Glu Tyr
                405                 410                 415

Lys Pro Ala Glu Ser Phe Ile Met Phe Gln Arg Trp Ile Ser Gly Gln
            420                 425                 430

Ser Leu

<210> SEQ ID NO 3
<211> LENGTH: 1227
<212> TYPE: DNA
<213> ORGANISM: Artificial Sequence
<220> FEATURE:
<223> OTHER INFORMATION: cDNA of C24 FPT1

<400> SEQUENCE: 3
atgaaatcaa cactaaaatt gctgcttctg cttctgttta tgttaaacca tcatgttgat     60
tctggctcta tcgtcaagtt tcttcccggc tttgaaggcc ctcttccttt cgaactcgaa    120
```

```
accgggtaca ttggtattgg tgaggaagag gaagtacagt tgttctacta ctttataaag    180
tctgagagaa atccaaaaga agaccctctt cttctctggt taagtggagg acctggatgt    240
tcatctatca ctggccttct tttcgagaat ggacctttgg ctttgaagtc cgaggtttac    300
aatggaagtg tcccttcttt ggtctctact acatattcgt ggacaaagac ggcgaacata    360
atattcttgg atcagcctat tggagctggc ttctcctact caagaatccc acttattgat    420
acgcctagtg acacaggcga agttaagaat atccatgagt ttctccaaaa gtggttaagc    480
aagcatccac agttttcttc caatcctttc tatgctagcg gagattctta ttccggtatg    540
attgttccag ccctcgttca agaaatttcg aaaggaaatt atatatgttg caaacctcct    600
ataaatctac agggctatat actcgggaac ccaataacat attttgaagt cgaccaaaac    660
tatcgcattc catttctca tggaatggca cttatttcag atgaactata cgagtcaatt    720
aggagagact gcaaaggaaa ttatttcaac gtggatccac gtaacacaaa atgtttgaaa    780
cttgttgaag aataccataa gtgtaccgac gaactaaatg aattcaatat attatcacca    840
gattgcgaca cgacatctcc tgattgcttt gtatatccat attatctcct tggctactgg    900
atcaacgacg agagcgttcg cgatgctctt catgttaata agagcagtat tggaaaatgg    960
gagcgatgta cttatcaaaa tagaatccca tacaacaaag acatcaataa cagcatacca   1020
taccatatga ataacagtat tagtggctac cgatctctca tctacagtgg tgatcatgat   1080
ttggtggttc ctttccttgc aactcaagcc tggataaaat ctctaaatta ctccatcatt   1140
catgaatgga gaccttggat gattaaagat caaatcgctg gtatataat atattttgt     1200 gttatacacg agaacttatt ccaataa                                       1227

<210> SEQ ID NO 4
<211> LENGTH: 408
<212> TYPE: PRT
<213> ORGANISM: Arabidopsis thaliana
<220> FEATURE:
<221> NAME/KEY: MISC_FEATURE
<222> LOCATION: (1)..(408)
<223> OTHER INFORMATION: amino acid sequence coded by SEQ-ID No. 3

<400> SEQUENCE: 4

Met Lys Ser Thr Leu Lys Leu Leu Leu Leu Leu Phe Met Leu Asn
1               5                   10                  15

His His Val Asp Ser Gly Ser Ile Val Lys Phe Leu Pro Gly Phe Glu
            20                  25                  30

Gly Pro Leu Pro Phe Glu Leu Glu Thr Gly Tyr Ile Gly Ile Gly Glu
        35                  40                  45

Glu Glu Glu Val Gln Leu Phe Tyr Tyr Phe Ile Lys Ser Glu Arg Asn
    50                  55                  60

Pro Lys Glu Asp Pro Leu Leu Leu Trp Leu Ser Gly Pro Gly Cys
65                  70                  75                  80

Ser Ser Ile Thr Gly Leu Leu Phe Glu Asn Gly Pro Leu Ala Leu Lys
                85                  90                  95

Ser Glu Val Tyr Asn Gly Ser Val Pro Ser Leu Val Ser Thr Thr Tyr
            100                 105                 110

Ser Trp Thr Lys Thr Ala Asn Ile Ile Phe Leu Asp Gln Pro Ile Gly
        115                 120                 125

Ala Gly Phe Ser Tyr Ser Arg Ile Pro Leu Ile Asp Thr Pro Ser Asp
    130                 135                 140

Thr Gly Glu Val Lys Asn Ile His Glu Phe Leu Gln Lys Trp Leu Ser
145                 150                 155                 160
```

Lys His Pro Gln Phe Ser Ser Asn Pro Phe Tyr Ala Ser Gly Asp Ser
                165                 170                 175

Tyr Ser Gly Met Ile Val Pro Ala Leu Val Gln Glu Ile Ser Lys Gly
            180                 185                 190

Asn Tyr Ile Cys Cys Lys Pro Ile Asn Leu Gln Gly Tyr Ile Leu
            195                 200                 205

Gly Asn Pro Ile Thr Tyr Phe Glu Val Asp Gln Asn Tyr Arg Ile Pro
        210                 215                 220

Phe Ser His Gly Met Ala Leu Ile Ser Asp Glu Leu Tyr Glu Ser Ile
225                 230                 235                 240

Arg Arg Asp Cys Lys Gly Asn Tyr Phe Asn Val Asp Pro Arg Asn Thr
                245                 250                 255

Lys Cys Leu Lys Leu Val Glu Glu Tyr His Lys Cys Thr Asp Glu Leu
            260                 265                 270

Asn Glu Phe Asn Ile Leu Ser Pro Asp Cys Asp Thr Thr Ser Pro Asp
        275                 280                 285

Cys Phe Val Tyr Pro Tyr Tyr Leu Leu Gly Tyr Trp Ile Asn Asp Glu
    290                 295                 300

Ser Val Arg Asp Ala Leu His Val Asn Lys Ser Ser Ile Gly Lys Trp
305                 310                 315                 320

Glu Arg Cys Thr Tyr Gln Asn Arg Ile Pro Tyr Asn Lys Asp Ile Asn
                325                 330                 335

Asn Ser Ile Pro Tyr His Met Asn Asn Ser Ile Ser Gly Tyr Arg Ser
            340                 345                 350

Leu Ile Tyr Ser Gly Asp His Asp Leu Val Val Pro Phe Leu Ala Thr
        355                 360                 365

Gln Ala Trp Ile Lys Ser Leu Asn Tyr Ser Ile His Glu Trp Arg
370                 375                 380

Pro Trp Met Ile Lys Asp Gln Ile Ala Gly Tyr Ile Ile Tyr Phe Cys
385                 390                 395                 400

Val Ile His Glu Asn Leu Phe Gln
            405

<210> SEQ ID NO 5
<211> LENGTH: 23
<212> TYPE: DNA
<213> ORGANISM: Artificial Sequence
<220> FEATURE:
<223> OTHER INFORMATION: forward primer for amplification of FPT2 cDNA
      (At2g22960)

<400> SEQUENCE: 5
atgagaactt tttcacccaa gtt                                          23

<210> SEQ ID NO 6
<211> LENGTH: 23
<212> TYPE: DNA
<213> ORGANISM: Artificial Sequence
<220> FEATURE:
<223> OTHER INFORMATION: reverse primer for amplification of FPT2 cDNA
      (At2g22960)

<400> SEQUENCE: 6
tcatcatctc ttattattac aga                                          23

<210> SEQ ID NO 7
<211> LENGTH: 737
<212> TYPE: DNA

<213> ORGANISM: Artificial Sequence
<220> FEATURE:
<223> OTHER INFORMATION: cDNA of Col0 FPT2-1

<400> SEQUENCE: 7

```
atgagaactt tttcacccaa gttgctgctt cttcttttac ttgttttaag acatcatgct    60
gaatctggct ctatcgtcaa gtttcttccc ggttttgaag ccctcttcc tttcgaactt    120
gaaaccgggg ctaccacagt acactagcta aatattgggc caatgacgag agggtacgtg   180
aagctcttca ataagaaag ggaagtatag gaaaatggat acgatgtaat tcgaatatac    240
attacgatga cgacattatt agcagcatac catatcatat gaataacagc atcaacggat   300
accgatctct tatttacagg tttgattaaa attacatttt aaagaatcga tctagttctc   360
tatacaaact atgcggtttt tggtaaacag tggtgatcac gatatggagg tacctttcct   420
tgcaactgaa gcttggataa gatctcttaa ttatcctatt attgatgatt ggaggccttg   480
gataataaac aatcagattg ctgggtgaat aattttttaca atttttttttt ttgcttcttt  540
attcattaac tcagtcgaat catgagctca ttagtcattt tgaaatccct cttacgattt   600
tcttggacag atacacgatg acctatgcca ataagatgac atatgctact atcaagggag   660
gtggacacac tgcagagtat aaaccagcgg agagctttat catgttccaa cgatggatca   720
gtggccagcc tctgtaa                                                  737
```

<210> SEQ ID NO 8
<211> LENGTH: 651
<212> TYPE: DNA
<213> ORGANISM: Artificial Sequence
<220> FEATURE:
<223> OTHER INFORMATION: cDNA of Col0 FPT2-2

<400> SEQUENCE: 8

```
atgagaactt tttcacccaa gttgctgctt cttcttttac ttgttttaag acatcatgct    60
gaatctggct ctatcgtcaa gtttcttccc ggttttgaag ccctcttcc tttcgaactt    120
gaaaccgggg ctaccacagt acactagcta aatattgggc caatgacgag agggtacgtg   180
aagctcttca ataagaaag ggaagtatag gaaaatggat acgatgtaat tcgaatatac    240
attacgatga cgacattatt agcagcatac catatcatat gaataacagc atcaacggat   300
accgatctct tatttacagt ggtgatcacg atatggaggt acctttcctt gcaactgaag   360
cttggataag atctcttaat tatcctatta ttgatgattg gaggccttgg ataataaaca   420
atcagattgc tggatacacg atgacctatg ccaataagat gacatatgct actatcaagg   480
caagttttt ttttttgttc ttactcttaa tgttttttat tacacaaatc attttgtttc    540
tcagtaactg ttttgagggg tttactatag ggaggtggac acactgcaga gtataaacca   600
gcggagagct ttatcatgtt ccaacgatgg atcagtggcc agcctctgta a             651
```

<210> SEQ ID NO 9
<211> LENGTH: 631
<212> TYPE: DNA
<213> ORGANISM: Artificial Sequence
<220> FEATURE:
<223> OTHER INFORMATION: cDNA of Col0 FPT2-3

<400> SEQUENCE: 9

```
atgagaactt tttcacccaa gttgctgctt cttcttttac ttgttttaag acatcatgct    60
gaatctggct ctatcgtcaa gtttcttccc ggttttgaag ccctcttcc tttcgaactt    120
gaaaccgggg ctaccacagt acactagcta aatattgggc caatgacgag agggtacgtg   180
```

```
aagctcttca aataagaaag ggaagtatag gaaaatggat acgatgtaat tcgaatatac    240
attacgatga cgacattatt agcagcatac catatcatat gaataacagc atcaacggat    300
accgatctct tatttacagg tttgattaaa attacatttt aaagaatcga tctagttctc    360
tatacaaact atgcggtttt tggtaaacag tggtgatcac gatatggagg tacctttcct    420
tgcaactgaa gcttggataa gatctcttaa ttatcctatt attgatgatt ggaggccttg    480
gataataaac aatcagattg ctggatacac gatgacctat gccaataaga tgacatatgc    540
tactatcaag ggaggtggac acactgcaga gtataaacca gcggagagct tatcatgtt     600 ccaacgatgg atcagtggcc agcctctgta a                                   631
```

```
<210> SEQ ID NO 10
<211> LENGTH: 560
<212> TYPE: DNA
<213> ORGANISM: Artificial Sequence
<220> FEATURE:
<223> OTHER INFORMATION: cDNA of Col0 FPT2-4

<400> SEQUENCE: 10
```

```
atgagaactt tttcacccaa gttgctgctt cttcttttac ttgttttaag acatcatgct     60
gaatctggct ctatcgtcaa gtttcttccc ggttttgaag gccctcttcc tttcgaactt    120
gaaaccgggg ctaccacagt acactagcta aatattgggc caatgacgag agggtacgtg    180
aagctcttca aataagaaag ggaagtatag gaaaatggat acgatgtaat tcgaatatac    240
attacgatga cgacattatt agcagcatac catatcatat gaataacagc atcaacggat    300
accgatctct tatttacagt ggtgatcacg atatggaggt acctttcctt gcaactgaag    360
cttggataag atctcttaat tatcctatta ttgatgattg gaggccttgg ataataaaca    420
atcagattgc tggatacacg atgacctatg ccaataagat gacatatgct actatcaagg    480
gaggtggaca cactgcagag tataaaccag cggagagctt atcatgttc caacgatgga    540 tcagtggcca gcctctgtaa                                               560
```

```
<210> SEQ ID NO 11
<211> LENGTH: 24
<212> TYPE: DNA
<213> ORGANISM: Artificial Sequence
<220> FEATURE:
<223> OTHER INFORMATION: forward primer of set 1 for amplification of
      FPT2 genome sequence

<400> SEQUENCE: 11
tggactagta cgagaattgc aaag                                           24
```

```
<210> SEQ ID NO 12
<211> LENGTH: 20
<212> TYPE: DNA
<213> ORGANISM: Artificial Sequence
<220> FEATURE:
<223> OTHER INFORMATION: reverse primer of set 1 for amplification of
      FPT2 genome sequence

<400> SEQUENCE: 12
accgggaaga aacttgacga                                                20
```

```
<210> SEQ ID NO 13
<211> LENGTH: 18
<212> TYPE: DNA
<213> ORGANISM: Artificial Sequence
<220> FEATURE:
```

<223> OTHER INFORMATION: forward primer of set 2 for amplification of
      FPT2 genome sequence

<400> SEQUENCE: 13
cgtggagcga ccagtgat                                                    18

<210> SEQ ID NO 14
<211> LENGTH: 20
<212> TYPE: DNA
<213> ORGANISM: Artificial Sequence
<220> FEATURE:
<223> OTHER INFORMATION: reverse primer of set 2 for amplification of
      FPT2 genome sequence

<400> SEQUENCE: 14
cttcacgtac cctctcgtca                                                  20

<210> SEQ ID NO 15
<211> LENGTH: 21
<212> TYPE: DNA
<213> ORGANISM: Artificial Sequence
<220> FEATURE:
<223> OTHER INFORMATION: forward primer of set 3 for amplification of
      FPT2 genome sequence

<400> SEQUENCE: 15
cttatgcagg gctaccacag t                                                21

<210> SEQ ID NO 16
<211> LENGTH: 22
<212> TYPE: DNA
<213> ORGANISM: Artificial Sequence
<220> FEATURE:
<223> OTHER INFORMATION: reverse primer of set 3 for amplification of
      FPT2 genome sequence

<400> SEQUENCE: 16
accactgttt accaaaaacc gc                                               22

<210> SEQ ID NO 17
<211> LENGTH: 22
<212> TYPE: DNA
<213> ORGANISM: Artificial Sequence
<220> FEATURE:
<223> OTHER INFORMATION: forward primer of set 4 for amplification of
      FPT2 genome sequence

<400> SEQUENCE: 17
atatcatatg aataacagca tc                                               22

<210> SEQ ID NO 18
<211> LENGTH: 20
<212> TYPE: DNA
<213> ORGANISM: Artificial Sequence
<220> FEATURE:
<223> OTHER INFORMATION: reverse primer of set 4 for amplification of
      FPT2 genome sequence

<400> SEQUENCE: 18
gcatagggca tcatcatctc                                                  20

<210> SEQ ID NO 19
<211> LENGTH: 19
<212> TYPE: DNA
<213> ORGANISM: Artificial Sequence
<220> FEATURE:
<223> OTHER INFORMATION: forward primer for amplification of FPT1 cDNA

```
                (At2g22920)

<400> SEQUENCE: 19
atgaaatcaa caccaaaat                                                19

<210> SEQ ID NO 20
<211> LENGTH: 23
<212> TYPE: DNA
<213> ORGANISM: Artificial Sequence
<220> FEATURE:
<223> OTHER INFORMATION: reverse primer for amplification of FPT1 cDNA
      (At2g22920)

<400> SEQUENCE: 20
atttaggtaa ggtcattcaa gta                                           23

<210> SEQ ID NO 21
<211> LENGTH: 10
<212> TYPE: PRT
<213> ORGANISM: Artificial Sequence
<220> FEATURE:
<223> OTHER INFORMATION: amino acid (aa) sequence of a variant of
      BLOCK 1
<220> FEATURE:
<221> NAME/KEY: MISC_FEATURE
<222> LOCATION: (7)..(9)
<223> OTHER INFORMATION: x = random amino acid
<220> FEATURE:
<221> NAME/KEY: MISC_FEATURE
<222> LOCATION: (7)..(9)
<223> OTHER INFORMATION: Xaa can be any naturally occuring amino acid

<400> SEQUENCE: 21

Gly Pro Gly Cys Ser Ser Xaa Xaa Xaa Leu
1               5                   10

<210> SEQ ID NO 22
<211> LENGTH: 6
<212> TYPE: PRT
<213> ORGANISM: Arabidopsis thaliana
<220> FEATURE:
<221> NAME/KEY: MISC_FEATURE
<222> LOCATION: (1)..(6)
<223> OTHER INFORMATION: amino acid (aa) sequence of a variant of
      BLOCK 2

<400> SEQUENCE: 22

Gly Asp Ser Tyr Ser Gly
1               5
```

UV-B ABSORBING COMPOUNDS ISOLATED FROM PLANTS

The present invention relates to compounds according to general formula (I) with enhanced absorption of UV-B irradiation. The present invention also relates to a UV-B tolerant transgenic plant and a method for enhanced production of compounds according to general formula (I) in a plant or plant cell using a transgenic plant. Furthermore, the invention relates to a nucleic acid sequence (SEQ-ID No.1) encoding FPT2, which catalyzes the production of compounds according to general formula (I).

The present invention therefore comprises a claim for a given product, namely the compounds according to general formula (I), an independent claim for a process especially adapted for the manufacture of these compounds, independent claims referring to a use of these compounds and in addition an independent claim referring to nucleic acid constructs and transgenic plants specifically designed for carrying out said process for manufacture of the inventive compounds.

The invention further relates to compositions comprising compounds according to general formula (I). Furthermore, the invention relates to a method of conferring UV-B tolerance to a plant as well as an UV-B tolerant plant comprising the nucleic acid sequence SEQ-ID No.1 encoding FPT2, which catalyzes the production of compounds according to general formula (I).

BACKGROUND OF THE INVENTION

It is intended to contribute to the solution of environmental problems caused by destroying the ozone layer and serious problems concerning the food resources in the $21^{st}$ century. The zonal average ultraviolet irradiance reaching the Earth's surface has continuously increased since 1979 at all latitudes except the equatorial zone even though the total area of the ozone hole has slightly decreased since 2006, most likely due to efforts restricting usage of chlorofluorocarbons.

The dependency of plants upon sunlight inevitably brings them into exposure to ultraviolet light, including that in the wavelength range 280-320 nm (UV-B). This wavelength range is potentially damaging to DNA, RNA and proteins and furthermore leads to increased production of free radicals that can activate transposons and cause mutations. Thus although only 0.5% of energy reaching the earth is in this wavelength range the risk of UV-B damage is profound. The potential impact of UV-B irradiation on natural plant populations could greatly impair crop yields since the detrimental effects described above combine to considerably constrain plant seed yields and seed germination rates. For this reason, plants have been under considerable natural selective pressure to generate elegant mechanisms to both sense and to respond to the presence UV-B irradiation.

One aspect of the response in land plants is the production of additional antioxidant sunscreen pigments including flavonoids and hydroxycinnamates, which belong to phenylpropanoids.

Flavonoids constitute a relatively diverse family of aromatic molecules that are derived from phenylalanine and malonyl-coenzyme A (malonyl-CoA). In the phenylpropanoid pathway, chalcone synthase (CHS) uses malonyl-CoA and 4-coumaroyl-CoA as substrates. Afterwards, chalcone isomerase (CHI) catalyses ring closure to form a flavanone. Further enzymes in the pathway are: flavanone 3-hydroxylase (F3H), dihydroflavonol 4-reductase (DFR), flavonoid 3'-hydroxylase (F3'H) and flavonoid 3',5' hydroxylase (F3'5H).

Natural variance screening has been carried out in many plant species including *Arabidopsis*. However, with regard to the accumulation of specific primary and secondary metabolites relatively few studies have focused on phenylpropanoid metabolism. However, plants with enhanced UV-B irradiation protection mechanisms are urgently needed, because the vast majority of people on earth are dependent on plant-based diet. Furthermore, phenolic compounds with the ability of defence against UV-B irradiation are needed as well.

Therefore, a primary object of the present invention was the provision of compounds that absorb UV-B irradiation and thereby protect biological materials as well as non-biological materials from damaging exposure to UV-B irradiation. Further object of the invention was the provision of genetically modified organisms, capable of providing compounds that absorb UV-B irradiation and thereby protect biological material from damaging exposure to UV-B irradiation.

An additional object of the present invention was the provision of formulations and compositions comprising such compounds.

The objective of the present invention is solved by the teaching of the independent claims. Further advantageous features, aspects and details of the invention are evident from the dependent claims, the description, the figures, and the examples of the present application.

DESCRIPTION OF THE INVENTION

Assessment of levels of various phenylpropanoids in flowers in a set of 72 *Arabidopsis thaliana* ecotypes was performed by the inventors. Application of liquid chromatography-mass spectrometry resulted in the detection of unknown chemical structures. MS-MS fragmentation studies suggested that these unknown peaks are novel flavonol derivatives. In order to characterize the chemical structure of these peaks large amounts of the C24 accession that accumulated these compounds were re-grown and purified. Column chromatography and HPLC analysis was carried out (see Example 1 and 2).

Surprisingly, compounds according to general formula (I), novel phenylacylated flavonol-glycosides, named saiginols, which display enhanced UV-B absorbent properties (FIG. 3 a-c), were detected. However, compounds according to general formula (I) do not absorb in the photosynthetically active radiation range. Accordingly, there is no trade off against photosynthetic efficiency. Furthermore, the position of the phenylacyl moieties of the compounds according to general formula (I) is structural distinct from all phenylacylated flavonols reported to date. Characterization of a compound according to general formula (I) was performed by NMR. FIG. 3d shows a computational estimation of the most stable stereochemical structure of a compound according to general formula (I).

According to an aspect of some embodiments of the present invention a compound of general formula (I) is provided

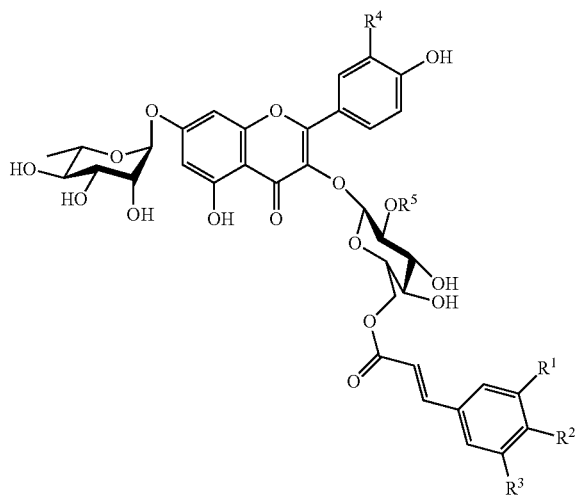

wherein

R¹, R² and R³ are independently of each other selected from: —H, —OH, and —OCH₃;

R⁴ is selected from —H, —OH, and —OCH₃;

R⁵ represents —H, or

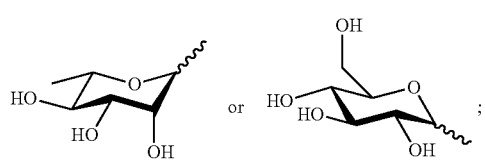

and enantiomers, mixtures of enantiomers, diastereoisomers, mixtures of diastereoisomers, hydrates and solvates thereof.

According to an aspect of some embodiments of the present invention a compound of general formula (II) is provided

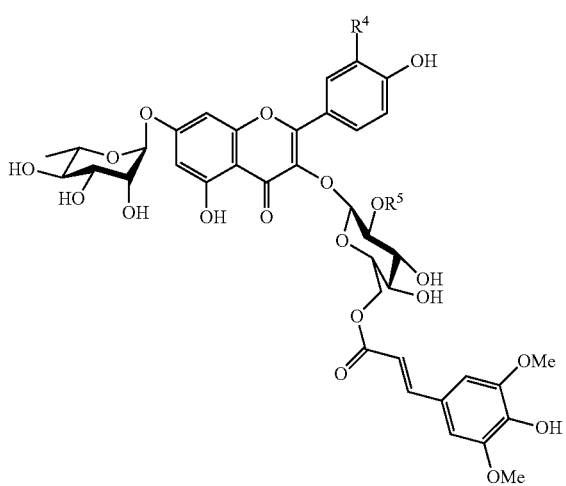

wherein

R⁴ is selected from —H, —OH, and —OCH₃;

R⁵ represents —H, or

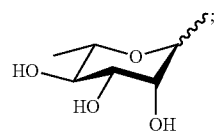

and enantiomers, mixtures of enantiomers, diastereoisomers, mixtures of diastereoisomers, hydrates and solvates thereof.

According to an aspect of some embodiments of the present invention a compound of general formula (III) is provided (III)

[structure III]

wherein

R⁴ is selected from —H, —OH, and —OCH₃;

R⁵ represents —H, or

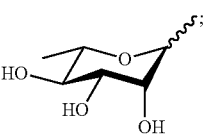

and enantiomers, mixtures of enantiomers, diastereoisomers, mixtures of diastereoisomers, hydrates and solvates thereof.

The term "saiginols", as used herein, refers to the compounds according to the general formula (I), as given above. Since the general formulas (II) (III) and (IV) fall under general formula (I), the term "saiginols", as used herein, refers also to the compounds according to general formula (II), (III) and (IV) as given below.

According to an aspect of some embodiments of the present invention a compound of general formula (IV) is provided (IV)
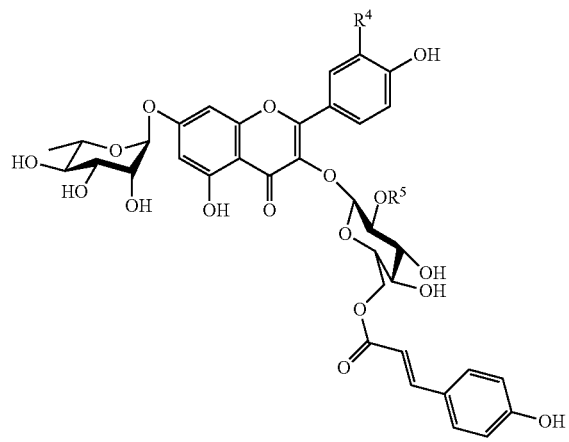
wherein
R⁴ is selected from —H, —OH, and —OCH₃;
R⁵ represents —H, or
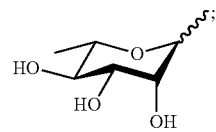
and enantiomers, mixtures of enantiomers, diastereoisomers, mixtures of diastereoisomers, hydrates and solvates thereof.
Preferably, the compounds according to the present invention are selected from:
Saiginol A*
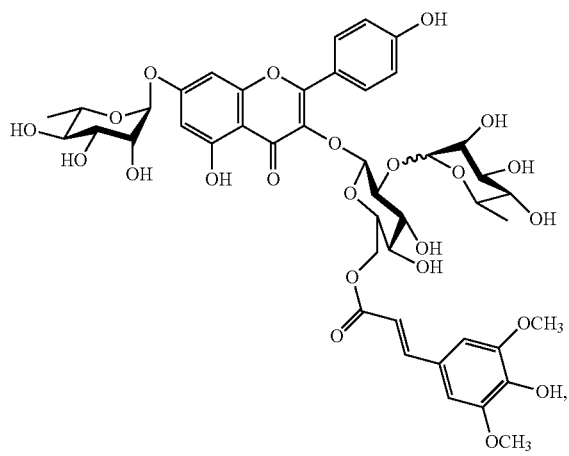
R⁵ = Rha (α/β)
Saiginol B*
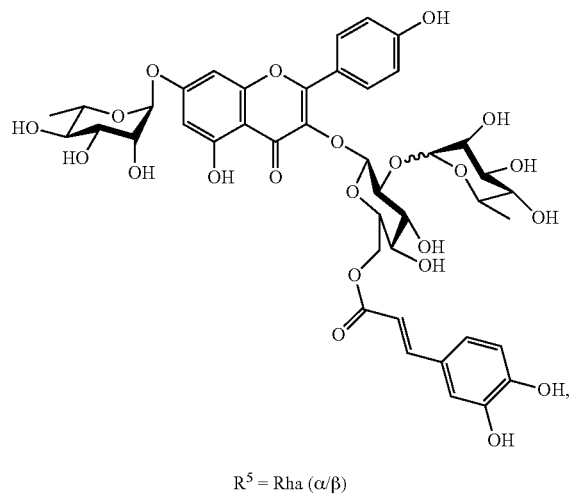
R⁵ = Rha (α/β)
Saiginol C*
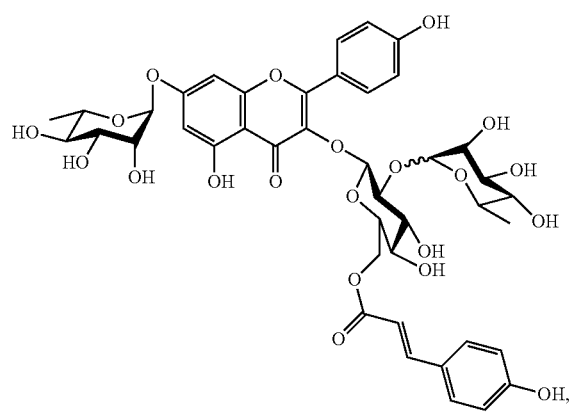
R⁵ = Rha (α/β)
Saiginol D
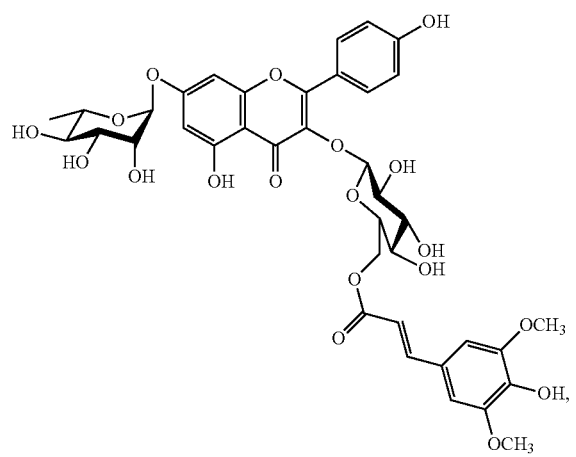

Saiginol E
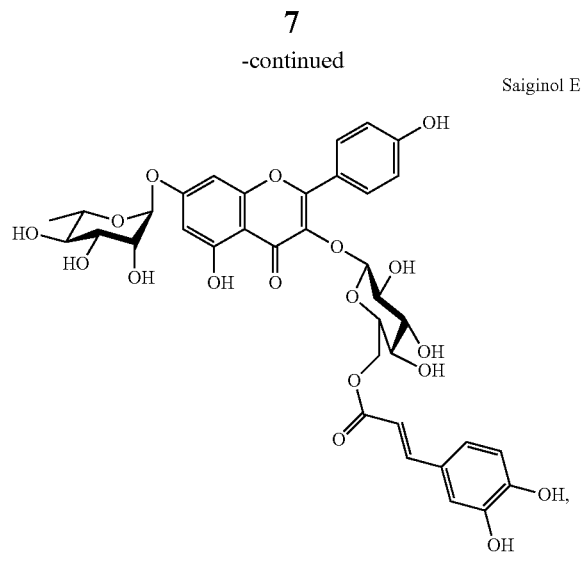
Saiginol F
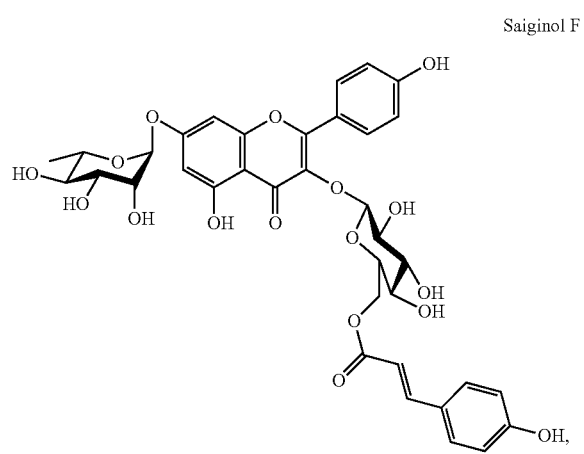
Saiginol G*
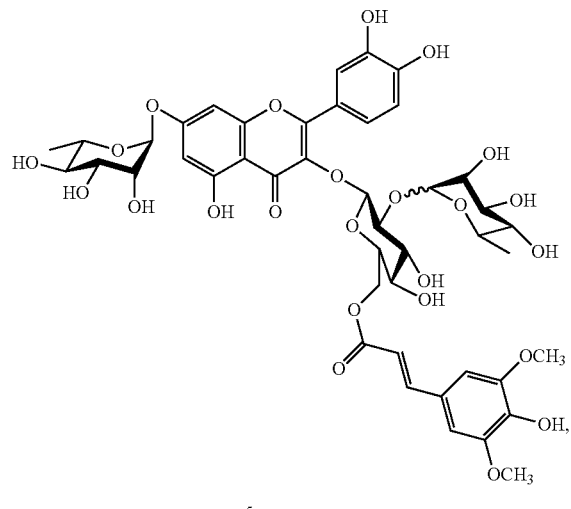
$R^5$ = Rha (α/β)
Saiginol H*
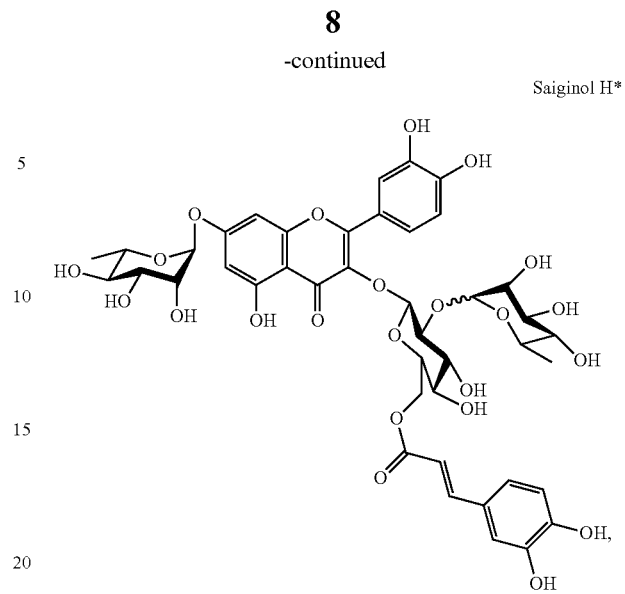
$R^5$ = Rha (α/β)
Saiginol I*
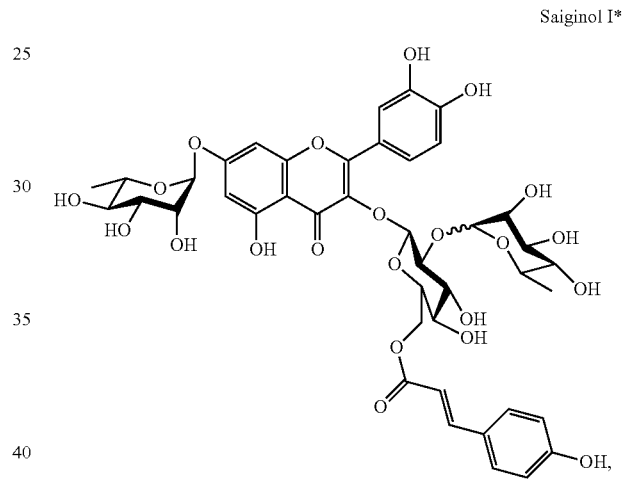
$R^5$ = Rha (α/β)
Saiginol J
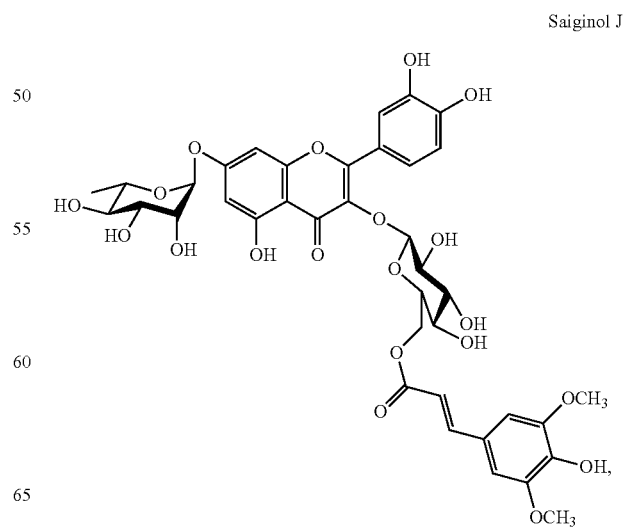

Saiginol K
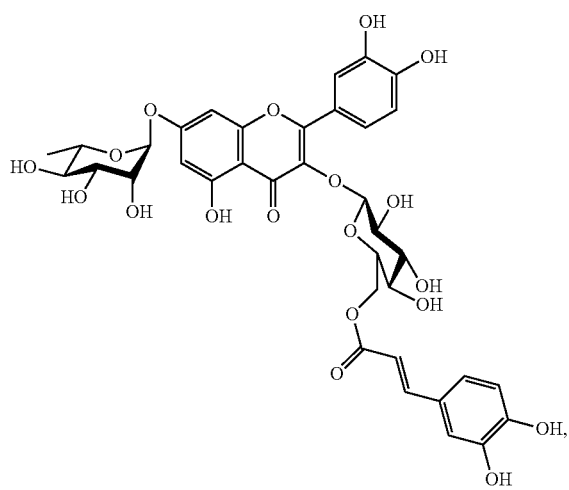
Saiginol N*
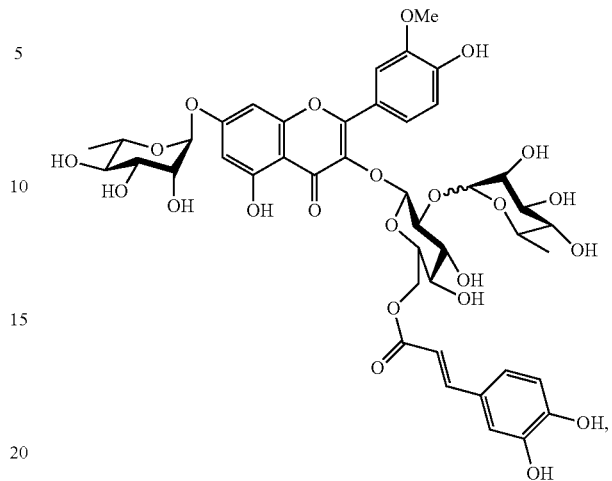
$R^5$ = Rha (α/β)
Saiginol L
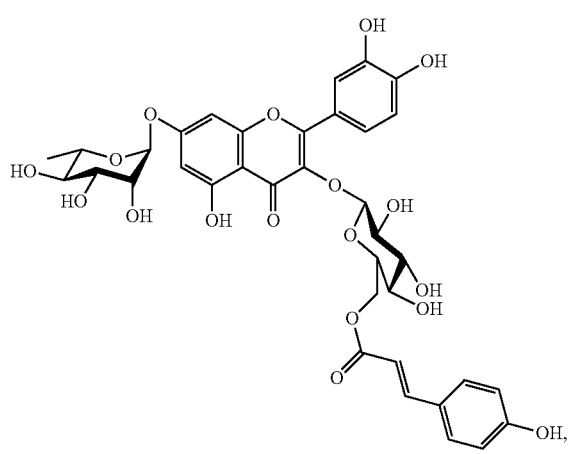
Saiginol O*
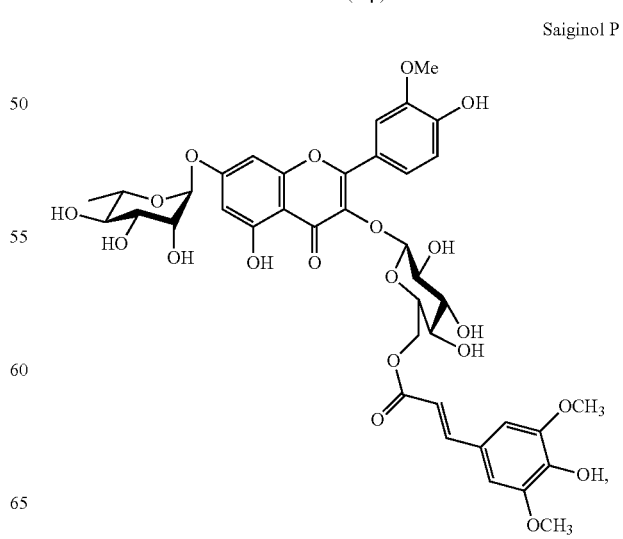
$R^5$ = Rha (α/β)
Saiginol M*
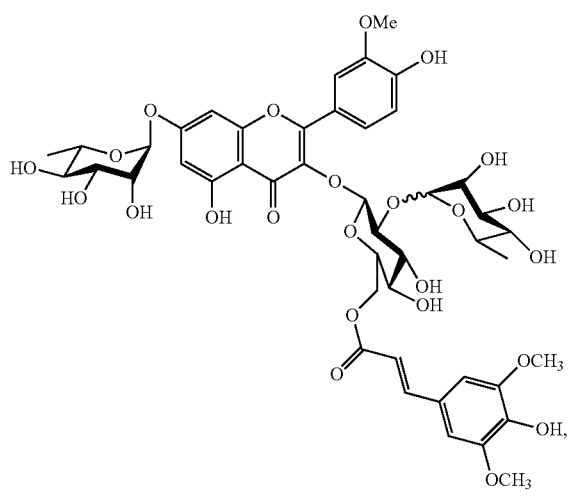
$R^5$ = Rha (α/β)
Saiginol P Saiginol Q

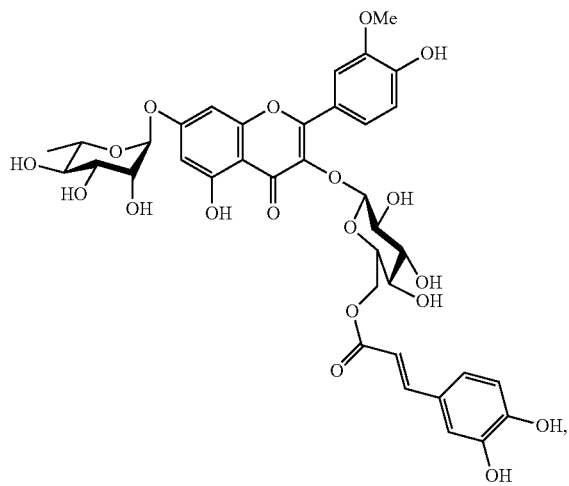

Saiginol A

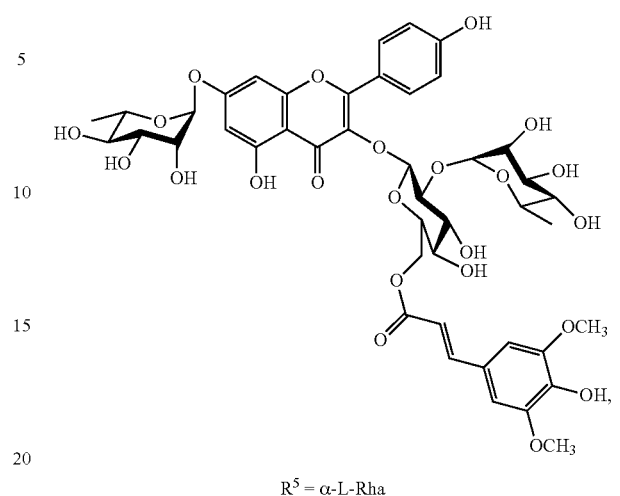

$R^5$ = α-L-Rha

Saiginol B

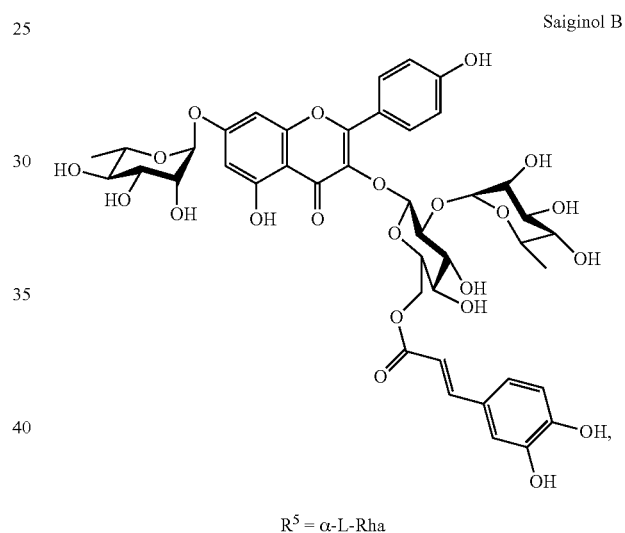

$R^5$ = α-L-Rha

Saiginol R

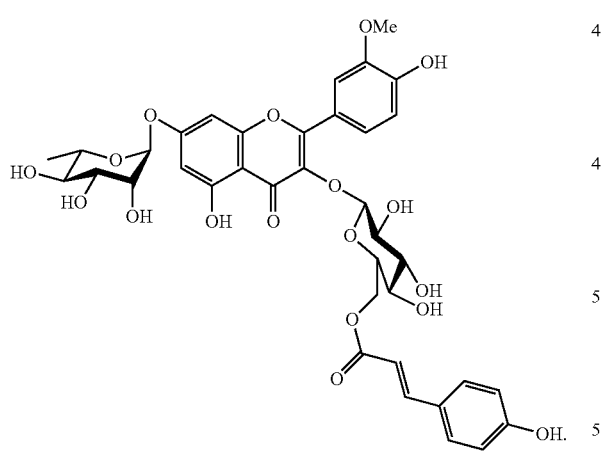

Saiginol C

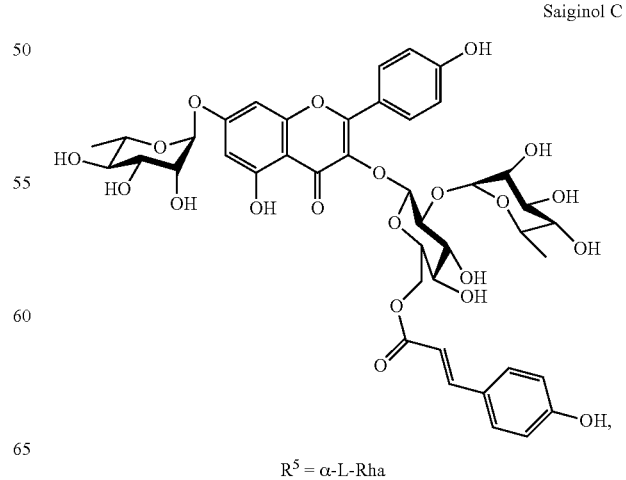

$R^5$ = α-L-Rha

Please note that the abbreviation "Rha", as used herein, stands for the monosaccharide rhamnose. However, in preferred embodiments of the present invention "Rha", if not indicated otherwise, is L-rhamnose (also sometimes designated specifically as L-Rha). Even more preferably, the compounds according to the present invention are selected from:

Saiginol D
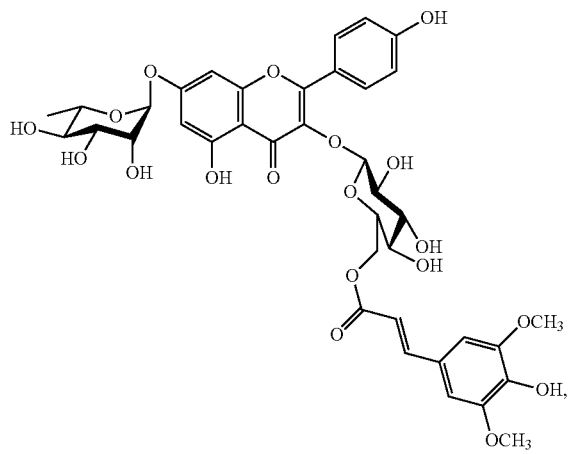
Saiginol E
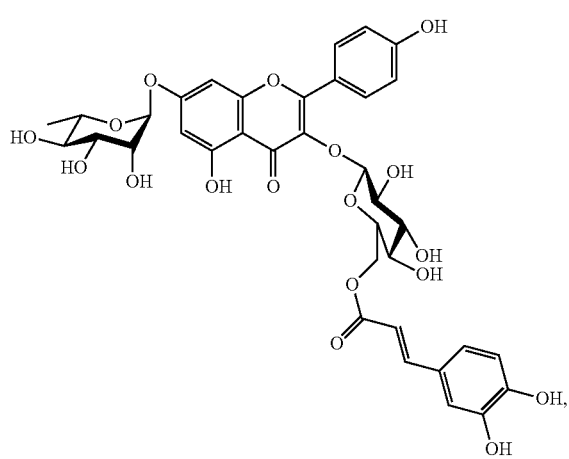
Saiginol F
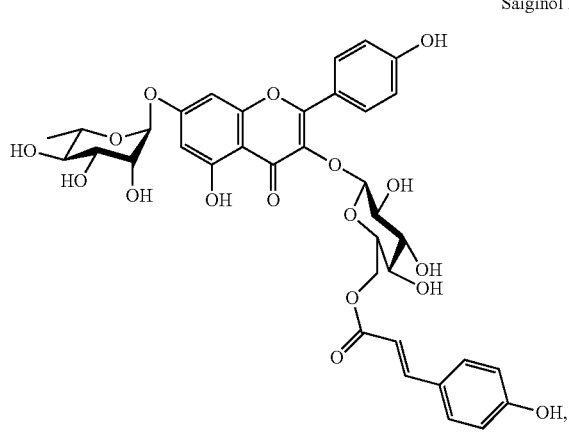
Saiginol G
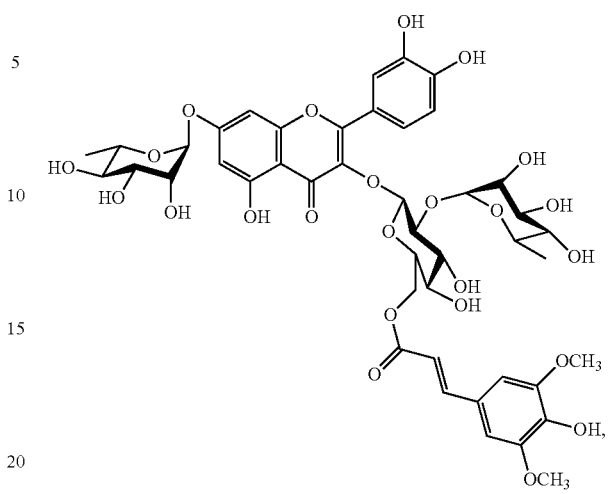
R⁵ = α-L-Rha
Saiginol H
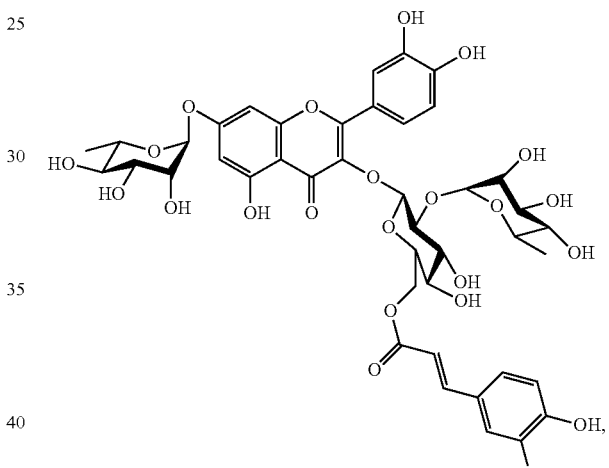
R⁵ = α-L-Rha
Saiginol I
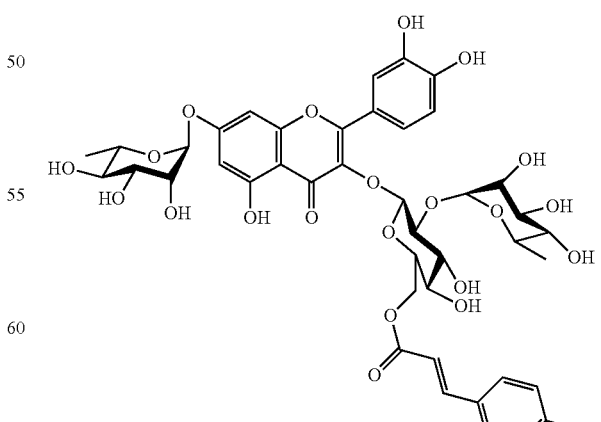
R⁵ = α-L-Rha Saiginol J
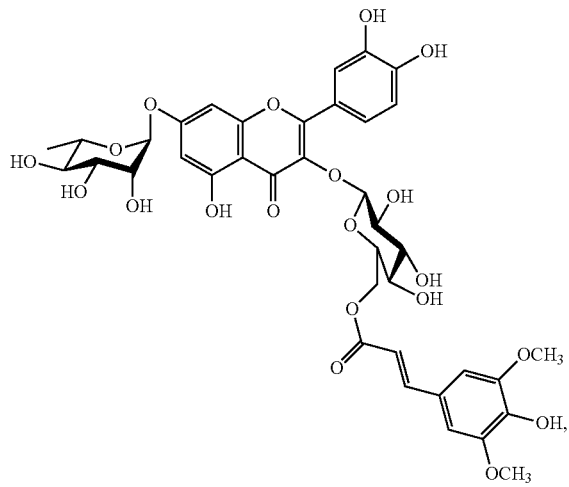
Saiginol M
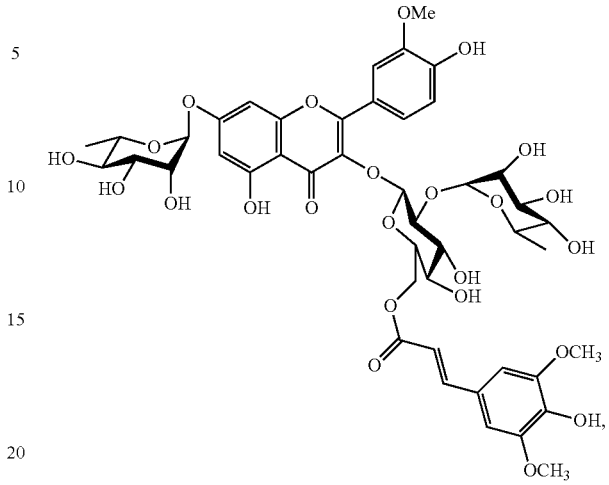
$R^5$ = α-L-Rha
Saiginol K
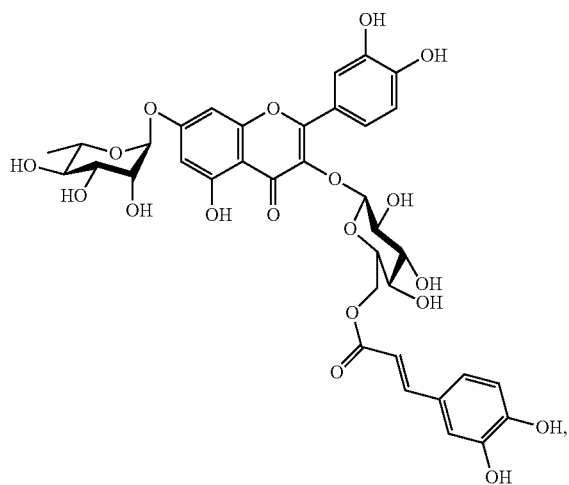
Saiginol N
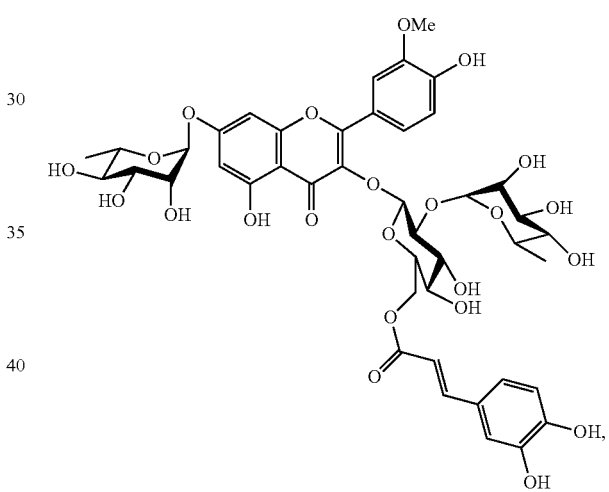
$R^5$ = α-L-Rha
Saiginol L
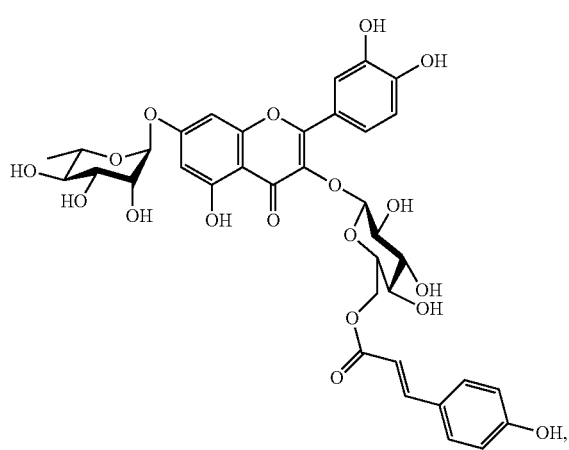
Saiginol O
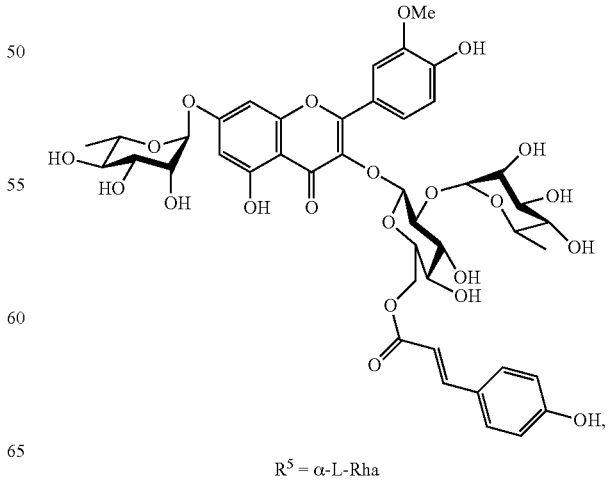
$R^5$ = α-L-Rha

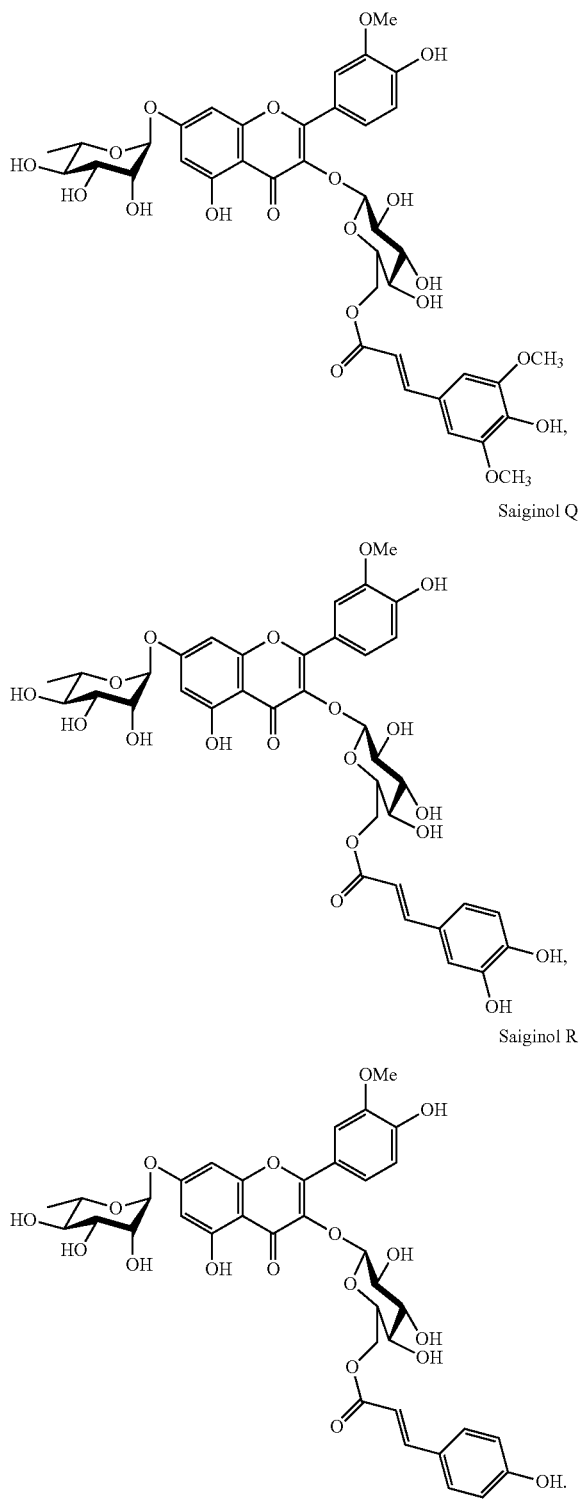

Saiginol P

Saiginol Q

Saiginol R

The inventive compounds according to general formula (I) accumulate in the floral petal and to a lesser extent in the stamen and pistil, but are absent in pollen (FIG. 1). However, inventors found that Col0 populations do not produce the inventive compounds according to general formula (I). The presence or absence of the inventive compounds according to general formula (I) was assessed by LC-MS (FIG. 5).

Furthermore, inventors generated reciprocal introgression lines harboring chromosome segmental substitutions of Col0 (non-producing the inventive compounds according to general formula (I)) in C24 (producing the inventive compounds according to general formula (I)), or substitutions of C24 in Col0 were re-grown (see also Example 5). Intriguingly, inventors found a loss-of-function line in the C24 population which mapped to the same genome region as the gain-of-function line in the Col0 population (see FIGS. 4 and 6).

Given that this genomic region on chromosome 2 of *Arabidopsis* harbors a total of 829 genes (FIG. 4), the inventors further performed transcript profiling in order to compare gene expression in the gain-of-function donor line (C24) and its recurrent parent (Col0). Expression levels were generally very similar between the genotypes although a number of genes were significantly different between producing and non-producing accessions including several transposable elements.

However, only two genes were dramatically altered between Col0 and C24, whereas the remaining 827 genes which were localized to the chromosomal segment substitution exhibited regular expression. The altered genes were renamed as putative flavonol phenylacyltransferases 1 (FPT1—At2g22920) and 2 (FPT2—At2g22960) (FIG. 7). The nucleic acid sequence of FPT2 (from C24) is referred to SED ID NO:1 and the nucleic acid sequence of FPT1 (from C24) is referred to SED ID NO:3.

Flavonol Phenylacyltransferase 2 (FPT2)

According to an aspect of some embodiments of the present invention a nucleic acid sequence, which has at least 80% sequence identity to SEQ-ID No.1, wherein the nucleic acid sequence encodes a polypeptide having phenylacyltransferase activity, is provided. In other words one embodiment of the present invention refers to a nucleic acid sequence, which has at least 80% sequence identity to SEQ-ID No.1, wherein the nucleic acid sequence encodes an enzyme having the same functionality as SEQ ID No. 1. Having the same functionality means that the enzyme or polypeptide comprises at least one part having phenylacyltransferase activity and thus is suitable to synthesize at least one compound of the invention.

According to a preferred embodiment of the present invention, a nucleic acid sequence which has at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, or 100% sequence identity to SEQ-ID No.1, wherein the nucleic acid sequence encodes a polypeptide having phenylacyltransferase activity, is provided.

The term "sequence identity", as used herein, indicates the percentage match of sequences by using an alignment between two sequences. An alignment is simply a correspondence between the sequences, in which each character in a sequence is assigned no more than one (maybe none) of the symbols in the other sequence, and in which the order of the symbols in the sequence is maintained, but in which gaps might be introduced into one or both sequence(s) to maximize identity. The sequence identity is usually and also in regard to the present invention calculated as the total number of matches (identical characters in both sequences at a certain position of the alignment) divided by the total length of the alignment of the two sequences and finally multiplied by 100. "Total length of the alignment", does thereby not refer to the length of the overlap between two aligned sequences, but to the entire length spanned by the aligned sequences, i.e. two sequences of 100 amino acids each, having an identical series of amino acids only in the last 10 amino acids of the first sequence and the first 10 amino acids of the second sequence, would result in a total alignment having a total length of 190 amino acids. Thus "sequence identity" is usually expressed as the percentage (%) of matches (identical characters) in positions from an alignment of two molecular sequences. The above concept can be used to determine the sequence identity of two polypeptide sequences (i.e. amino acid sequences) as well as of two nucleotide sequences (i.e. DNA or RNA). Sequences can be aligned with the use of a variety of computer programs known in the art, as for example BioEdit (Hall, T. A. (1999), *Nucl. Acids. Symp. Ser.* 41, 95-98).

Another aspect of the present invention is directed to an isolated nucleic acid molecule comprising a nucleic acid sequence having at least 80% or higher (as mentioned before) sequence identity to SEQ-ID No. 1, and encoding a polypeptide having phenylacyltransferase activity. Preferably no modifications like deletions, insertions or replacement of amino acids are made within the active site of the protein. Preferably all modifications which lead to the above-mentioned sequence identity deviant from 100% are present at amino acid positions of the enzyme outside the active site of the enzyme. In case one or more modifications are present within the active site of the enzyme, these modifications shall not decrease the catalytic activity of the enzyme.

The present invention is also related to a nucleic acid molecule encoding a polypeptide which is capable of conferring resistance against UV-B irradiation in a plant, in which said polypeptide is expressed, said nucleic acid molecule comprising or consisting of a nucleic acid sequence encoding at least the mature form of a polypeptide comprising the amino acid sequence as given in SEQ-ID No. 2.

The present invention is also related to a nucleic acid molecule encoding a polypeptide which is capable of conferring resistance against UV-B irradiation in a plant, in which said polypeptide is expressed, said nucleic acid molecule comprising or consisting of a nucleic acid sequence comprising the coding regions of the DNA sequence as given in SEQ-ID No. 1.

The present invention is also related to a nucleic acid molecule encoding a polypeptide which is capable of conferring resistance against UV-B irradiation in a plant, in which said polypeptide is expressed, said nucleic acid molecule comprising or consisting of a nucleic acid sequence encoding a polypeptide having at least 80% sequence identity to SEQ ID No: 2.

The present invention is also related to a nucleic acid molecule encoding a polypeptide which is capable of conferring resistance against UV-B irradiation in a plant, in which said polypeptide is expressed, said nucleic acid molecule comprising or consisting of a nucleic acid sequence encoding a polypeptide having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ-ID No.2. Thereby it is preferred that the functionality or enzyme activity of said polypeptide is not changed or not decreased.

Nucleic acid molecules and nucleic acid sequences according to the present invention may be provided in recombinant form or free or substantially free of nucleic acid or genes of the species of interest or origin other than the sequence encoding a polypeptide with the required function. The nucleic acid molecules and nucleic acid sequences (and their encoded polypeptide products) may also be (i) isolated and/or purified from their natural environment (although not necessarily in pure form per se), or (ii) in substantially pure or homogeneous form.

Nucleic acid molecules and nucleic acid sequences according to the present invention may include cDNA, RNA, genomic DNA, preferably the intact gene, and may be wholly or partially synthetic (constructs'). Where a DNA sequence is specified, e. g. with reference to a figure or SEQ-ID No., unless context requires otherwise, the RNA equivalent, in which T (thymine) is replaced by U (uracil), is also encompassed. Also encompassed is the complement of the various disclosed sequences, which may be used in probing experiments, or in down-regulation of the sequence.

Isolated nucleic acid molecules can be produced by standard techniques. For example, polymerase chain reaction (PCR) techniques can be used to obtain an isolated nucleic acid containing a nucleic acid sequence described herein. PCR can be used to amplify specific sequences from DNA as well as RNA, including sequences from total genomic DNA or total cellular RNA. Various PCR methods are described, for example, in PCR Primer: A Laboratory Manual, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleic acid sequence modifications can be introduced into a template nucleic acid. Isolated nucleic acids can also be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring DNA.

The term "isolated", as used herein, means that the material is removed from its original environment (e.g. the natural environment, if it is naturally occurring). For example, a naturally occurring nucleic acid present in a living plant is not isolated, but the same nucleic acid separated from some or all of the coexisting (e.g. proteins, other nucleic acids) materials in the natural system, is isolated. Such nucleic acids could be part of a vector and/or such nucleic acids could be part of a nucleic acid construct, and still be isolated in that such a vector or construct is not part of its natural environment.

Nucleic acid molecules and nucleic acid sequences of the present invention may be optimized for plant expression. Examples of such sequence modifications include, but are not limited to, an altered G/C content to more closely approach the G/C content typically found in the plant species of interest, and the removal of codons atypically found in the plant species commonly referred to as codon optimization.

The phrase "codon optimization", as used herein, refers to the selection of appropriate DNA nucleotides for use within a structural gene or fragment thereof that approaches codon usage within the plant of interest. Therefore, an optimized gene or nucleic acid sequence refers to a gene in which the nucleic acid sequence of a native or naturally occurring gene has been modified in order to utilize statistically-preferred or statistically-favoured codons within the plant. The nucleic acid sequence typically is examined at the DNA level and the coding region optimized for expression in the plant species determined using any suitable procedure, for example as described in Sardana et al. (1996, Plant Cell Reports 15:677-681). A table of codon usage from highly expressed genes of dicotyledonous plants is compiled using the data of Murray et al. (1989, Nuc Acids Res. 17:477-498).

The nucleic acid sequence of the present invention can be, for example, utilized in preparation of recombinant polypeptides (or recombinant proteins) as well as in production of transformant plants with enhanced UV-B tolerance.

In preparing recombinant polypeptides, generally, a nucleic acid sequence encoding the polypeptides of the present invention is inserted into an appropriate expression vector, the expression vector is transferred into an appropriate cell, the transformed cell is cultivated and the expressed polypeptides according to the invention is purified.

According to an aspect of some embodiments of the present invention a polypeptide which has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 93%, at least 94%, at least 95%, at least 96%, at least 97%, at least 98%, at least 99%, or 100% sequence identity to SEQ-ID No. 2, wherein the polypeptide has phenylacyltransferase activity, is provided.

Another aspect of the present invention is related to a nucleic acid sequence encoding for a polypeptide having at least at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 93%, at least 94%, at least 95%, at least 96%, at least 97%, at least 98%, at least 99%, or 100% sequence identity to SEQ-ID No. 2, wherein the polypeptide has phenylacyltransferase activity.

The present invention is also directed to an isolated nucleic acid molecule comprising a nucleotide sequence encoding a polypeptide having phenlyacyltransferase activity and having an amino acid sequence with at least 70% sequence identity to SEQ-ID No. 2.

The present invention is also directed to an isolated nucleic acid molecule comprising a nucleotide sequence encoding a polypeptide having phenlyacyltransferase activity and having an amino acid sequence with at least 80% sequence identity to SEQ-ID No. 2.

The present invention is also directed to an isolated nucleic acid molecule comprising a nucleotide sequence encoding a polypeptide having phenlyacyltransferase activity and having an amino acid sequence with at least 90% sequence identity to SEQ-ID No. 2.

The term "sequence identity", as used herein, indicates the percentage match of sequences by using an alignment between two sequences. An alignment is simply a correspondence between the sequences, in which each character in a sequence is assigned no more than one (maybe none) of the symbols in the other sequence, and in which the order of the symbols in the sequence is maintained, but in which gaps might be introduced into one or both sequence(s) to maximize identity. The sequence identity is usually calculated as the total number of matches (identical characters in both sequences at a certain position of the alignment) divided by the total length of the alignment of the two sequences and finally multiplied by 100. Thus "sequence identity" is usually expressed as the percentage (%) of matches (identical characters) in positions from an alignment of two molecular sequences. The above concept can be used to determine the sequence identify of two polypeptide sequences (i.e. amino acid sequences) as well as of two nucleotide sequences (i.e. DNA or RNA). Sequences can be aligned with the use of a variety of computer programs known in the art, as for example BioEdit (Hall, T. A. (1999), *Nucl. Acids. Symp. Ser.* 41, 95-98).

As it was already mentioned above, the isolated nucleic acid molecule according to the present invention or the polypeptide according to the present invention shall not be modified in its sequence to an extent that diminishes or even abolishes the enzymatic function of the polypeptide according to the present invention or the polypeptide encoded by the nucleic acid molecule according to the present invention. This means the phenylacyltransferase activity shall not be diminished or abolished, since this would impair the capability to synthesize the inventive saiginols.

In this context, it is preferred, if the inventive polypeptide has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 93%, at least 94%, at least 95%, at least 96%, at least 97%, at least 98%, or at least 99% sequence identity to SEQ-ID No. 2, wherein within said percentage of sequence identity a sequence is included, which is 100% identical to a region (also termed "BLOCK 1") from amino acid position 58 to amino acid position 107, preferably from amino acid position 63 to amino acid position 102, more preferably from amino acid position 68 to amino acid position 97, more preferably from amino acid position 70 to amino acid position 90, even more preferably from amino acid position 73 to amino acid position 92, and even more preferably from amino acid position 78 to amino acid position 87 of SEQ-ID No. 2, and wherein within said percentage of sequence identity also a sequence is included, which is 100% identical to a region (also termed "BLOCK 2") from amino acid position 155 to amino acid position 200, more preferably from amino acid position 160 to amino acid position 195, more preferably from amino acid position 165 to amino acid position 190, even more preferably from amino acid position 170 to amino acid position 185, and even more preferably from amino acid position 175 to amino acid position 180 of SEQ-ID No. 2.

It shall be understood that the given regions for BLOCK 1 and BLOCK 2 (as detailed above) can be freely combined with each other, i.e. it is not mandatory that the widest range of BLOCK 1 has to be combined with the widest range of BLOCK 2. Moreover, it shall be understood that the two regions, i.e. BLOCK 1 and BLOCK 2 can be separated from each other by a sequence of amino acids.

However, it is especially preferred in accordance with the invention, if the inventive polypeptide has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 93%, at least 94%, at least 95%, at least 96%, at least 97%, at least 98%, or at least 99% sequence identity to SEQ-ID No. 2, wherein within said percentage of sequence identity a sequence is included, which is 100% identical to a region (also termed "BLOCK 1") from amino acid position 78 to amino acid position 87 of SEQ-ID No. 2, and wherein within said percentage of sequence identity also a sequence is included, which is 100% identical to a region (also termed "BLOCK 2") from amino acid position 175 to amino acid position 180 of SEQ-ID No. 2.

It is even more preferred in accordance with the invention, if the inventive polypeptide has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 93%, at least 94%, at least 95%, at least 96%, at least 97%, at least 98%, or at least 99% sequence identity to SEQ-ID No. 2, wherein within said percentage of sequence identity a sequence is included, which is 100% identical to the amino acid sequence GPGCSSxxxL (SEQ-ID No. 21), wherein x represents a random amino acid, and wherein within said percentage of sequence identity also a sequence is included, which is 100% identical to the amino acid sequence GDSYSG (SEQ-ID No. 22).

Concerning an inventive nucleic acid molecule, this is slightly more complicated, since the redundancy of the genetic code, i.e. several nucleotide triplets may code for more than one amino acid, allows a certain variation of the codon triplets without affecting the sequence of the final polypeptide.

Thus, it is preferred, if the inventive nucleic acid sequence has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 93%, at least 94%, at least 95%, at least 96%, at least 97%, at least 98%, or at least 99% sequence identity to SEQ-ID No. 1, wherein within said percentage of sequence identity a sequence is included that encodes at least an amino acid sequence 100% identical to a region (also termed "BLOCK 1") from amino acid position 58 to amino acid position 107, preferably from amino acid position 63 to amino acid position 102, more preferably from amino acid position 68 to amino acid position 97, more preferably from amino acid position 70 to amino acid position 90, even more preferably from amino acid position 73 to amino acid position 92, and even more preferably from amino acid position 78 to amino acid position 87 of SEQ-ID No. 2, and wherein within said percentage of sequence identity also a sequence is included that encodes at least an amino acid sequence 100% identical to a region (also termed "BLOCK 2") from amino acid position 155 to amino acid position 200, more preferably from amino acid position 160 to amino acid position 195, more preferably from amino acid position 165 to amino acid position 190, even more preferably from amino acid position 170 to amino acid position 185, and even more preferably from amino acid position 175 to amino acid position 180 of SEQ-ID No. 2.

It is even more preferred, if the inventive nucleic acid sequence has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 93%, at least 94%, at least 95%, at least 96%, at least 97%, at least 98%, or at least 99% sequence identity to SEQ-ID No. 1, wherein within said percentage of sequence identity a sequence is included that encodes at least an amino acid sequence 100% identical to a region (also termed "BLOCK 1") from amino acid position 78 to amino acid position 87 of SEQ-ID No. 2, and wherein within said percentage of sequence identity also a sequence is included that encodes at least an amino acid sequence 100% identical to a region (also termed "BLOCK 2") from amino acid position 175 to amino acid position 180 of SEQ-ID No. 2.

Still even more preferred is an inventive nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 93%, at least 94%, at least 95%, at least 96%, at least 97%, at least 98%, or at least 99%, sequence identity to SEQ-ID No. 1, wherein within said percentage of sequence identity a sequence is included that encodes at least the amino acid sequence GPGCSSxxxL (SEQ-ID No. 21), wherein x represents a random amino acid, and wherein within said percentage of sequence identity also a sequence is included that encodes the amino acid sequence GDSYSG (SEQ-ID No. 22).

Amino acid or nucleotide positions, which are counted herein, start from the first letter in the respective sequence or SEQ-ID No. and start with "1".

Transgenic Plants

In order to experimentally test the function of the FPT proteins encoded by the DNA sequences SEQ-ID No. 1 and SEQ-ID No. 3, the inventors performed complementation assays in Col0 and knockout fpt1 and fpt2 mutants. CaMV 35S driven complementation of the Col0 fpt2 knockout mutant (FIG. 8) with the C24 allele of FPT2 resulted in the production of the compound according to the invention in flowers of the transgenic plant, however neither expression of the Col0 allele of FPT2 in the Col0 fpt2 knockout line nor expression of the Col0 or the C24 allele in the Col0 fpt1 mutants yielded flowers which produce compounds according to general formula (I). However, the total flavonol content is equivalent in all genotypes. Therefore, only FPT2 functions as a phenylacyltransferase in vivo, catalyzing the phenylacylation of precursors of compounds according to general formula (I) and accordingly finalizes the biosynthesis of compounds according to general formula (I).

Thus, another aspect of the present invention is related to convey the capability to produce the inventive saiginols to a plant or a plant cell.

Plant cells may be transformed stably or transiently with the nucleic acid constructs of the present invention. In stable transformation, the nucleic acid molecule of the present invention is integrated into the plant genome and as such it represents a stable and inherited trait. In transient transformation, the nucleic acid molecule is expressed by the cell transformed but it is not integrated into the genome and as such it represents a transient trait.

Techniques for introducing exogenous nucleic acid sequences to the genome of the chloroplasts are known to a person skilled in the art. For example, a technique for introducing exogenous nucleic acid sequences to the genome of the chloroplasts is involves the following procedures: First, plant cells are chemically treated so as to reduce the number of chloroplasts per cell to about one. Then, the exogenous nucleic acid is introduced via particle bombardment into the cells with the aim of introducing at least one exogenous nucleic acid molecule into the chloroplasts. The exogenous nucleic acid is selected such that it is integratable (i.e. it can be integrated) into the chloroplast's genome via homologous recombination, which is readily effected by enzymes inherent to the chloroplast.

Thus, a preferred embodiment of the present invention is directed to a method for expressing in the plant or plant cell a vector comprising a nucleic acid sequence having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 93%, at least 94%, at least 95%, at least 96%, at least 97%, at least 98%, at least 99%, or 100% identity to SEQ-ID No. 1.

The term "plant", as used herein, encompasses whole plants, ancestors and progeny of the plants and plant parts, including flower, leaf, root (including tubers), fruit, seed, shoot, stem, twig) and plant cells (homogeneous or heterogeneous populations of cells), tissues and organs. The plant may be in any form including suspension cultures, embryos, meristematic regions, callus tissue, leaves, gametophytes, sporophytes, pollen, and microspores. Plants that are particularly useful in the methods of the invention include all plants which are commercially or scientifically valuable and which taste, aroma or pigmentation modification is desired. A suitable plant for use with the method of the invention can be any potted plant, hydroponically-grown plant, field-grown plant, greenhouse-grown plant, in vitro-grown plant, in particular monocotyledonous and dicotyledonous plants including a fodder or forage legume, ornamental plant, food crop, tree, or shrub.

According to an exemplary embodiment of the present invention, the plant is selected from the genus *Arabidopsis*.

However, transformation methods can be used for any plant, and are not limited to *Arabidopsis*. In general, the plants which can be modified according to the invention and which for example show overexpression of a polypeptide according to the invention can be derived from any desired plant species. They can be monocotyledonous plants or dicotyledonous plants, preferably they belong to plant species of interest in agriculture, wood culture or horticulture interest, such as crop plants (e.g. maize, rice, barley, wheat, rye, oats etc.), potatoes, oil producing plants (e.g. oilseed rape, sunflower, pea nut, soy bean, etc.), cotton, sugar beet, sugar cane, leguminous plants (e.g. beans, peas etc.), wood producing plants, preferably trees, etc. Following transformation of desired plant with the nucleic acid according to the invention or a nucleic acid sequence encoding the polypeptide according to the invention, a plant may be regenerated, e.g. from single cells, callus tissue or leaf discs, as is standard in the art. Almost any plant can be entirely regenerated from cells, tissues and organs of the plant.

Even though both monocotyledonous plants and dicotyledonous plants can be used in accordance with the present invention (e.g. for transformation), it is especially preferred according to certain embodiments, if the plant used is dicotyledonous plant.

In case the plant used in accordance with the invention is a dicotyledonous plant, it is especially preferred, if the plant is selected from *Arabidopsis* and/or tomato and/or tobacco.

In case the plant used in accordance with the invention is a monocotyledonous plant, it is preferred, if the plant is selected from maize (corn), rice, barley, wheat, rye, oats, sorghum, millet, triticale, fonio, teff, and wild rice; more preferably from maize (corn), rice, barley, wheat, rye, oats; and especially preferably the plant used in accordance with the invention is rice.

Transient transformation can be effected by any of the direct DNA transfer methods described above or by viral infection using modified plant viruses.

In addition to the above, the nucleic acid molecule of the present invention can also be introduced into a chloroplast genome thereby enabling chloroplast expression.

According to an aspect of some embodiments of the present invention a vector comprising the nucleic acid sequence SEQ-ID No.1 is provided. Also preferred is a vector comprising the nucleic acid sequence according to claim 6.

The present invention is also related to a vector comprising a nucleic acid sequence having at least 80% (or higher as disclosed herein) sequence identity to SEQ-ID No. 1.

The present invention is additionally related to a vector comprising a nucleic acid sequence having at least 80% sequence identity to SEQ-ID No. 1, wherein the vector is an expression vector in which the nucleic acid sequence is operatively linked to one or more control sequences allowing the transcription and optionally expression in prokaryotic and/or eukaryotic host cells.

Another aspect of the present invention is related to a host cell containing a nucleic acid molecule comprising a nucleic acid sequence having at least 80% sequence identity (or higher as disclosed herein) to SEQ-ID No. 1;

or containing a vector comprising a nucleic acid sequence having at least 80% (or higher as disclosed herein) sequence identity to SEQ-ID No. 1, wherein the vector is an expression vector in which the nucleic acid sequence is operatively linked to one or more control sequences allowing the transcription and optionally expression said host cell.

The host cell according to the invention may be selected from bacterial cells, fungal cells, yeast cells, insect cells, vertebrate cells and plant cells. It is especially preferred in accordance with the invention, if the host cell is a plant cell. Thus, another aspect of the invention is related to a transgenic plant or a transgenic plant tissue comprising said plant cell.

"Vector", as used herein, is defined to include, inter alia, any plasmid, cosmid, phage or *Agrobacterium* binary vector in double or single stranded linear or circular form, which may or may not be self transmissible or mobilizable, and which can transform prokaryotic or eukaryotic hosts either by integration into the cellular genome or exist extrachromosomally (e.g. autonomous replicating plasmid with an origin of replication). Specifically included are shuttle vectors by which is meant a DNA vehicle capable, naturally or by design, of replication in two different host organisms, which may be selected from actinomycetes (and related species), bacteria and eukaryotic organisms (e.g. higher plant, mammalian, yeast or fungal cells). A vector including a nucleic acid according to the present invention does not need to include a promoter or other regulatory sequence, particularly if the vector is to be used to introduce the nucleic acid into cells for recombination into the genome.

Preferably the nucleic acid in the vector is under the control of, and operably linked to, an appropriate promoter or other regulatory elements for transcription in a host cell such as a microbial, e.g. bacterial, or plant cell. The vector may be a bifunctional expression vector which functions in multiple hosts. In the case of genomic DNA, this may contain its own promoter or other regulatory elements and in the case of cDNA this may be under the control of an appropriate promoter or other regulatory elements for expression in the host cell.

By "promoter", as used herein, is meant a sequence of nucleotides from which transcription may be initiated of DNA operably linked downstream (i.e. in the 3-direction on the sense strand of double-stranded DNA).

"Operably linked", as used herein, means joined as part of the same nucleic acid molecule, suitably positioned and oriented for transcription to be initiated from the promoter. DNA operably linked to a promoter is "under transcriptional initiation regulation" of the promoter.

Another embodiment of this aspect of the present invention provides a gene construct, preferably a replicable vector, comprising an inducible promoter operatively linked to a nucleotide sequence provided by the present invention.

The term "inducible" as used in connection with "promoter" is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus. The preferable situation is where the level of expression increases upon application of the relevant stimulus by an amount effective to alter a phenotypic characteristic. Thus an inducible (or "switchable") promoter may be used which causes a basic level of expression in the absence of the stimulus which level is too low to bring about a desired phenotype (and may in fact be zero). Upon application of the stimulus, expression is increased (or switched on) to a level which brings about the desired phenotype.

Possible regulatory elements permitting expression in prokaryotic host cells comprise, e.g., the PL, lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. In this context, suitable expression vectors are known in the art such as Okayama-Berg cDNA expression vector pcDV1 (Pharmacia), pCDM8, pRc/CMV, pcDNA1, pcDNA3 (Invitrogen), pSPORT1 (GIBCO BRL).

Particularly of interest in the present context are plant vectors. Specific procedures and vectors previously used with wide success upon plants are described in the prior art. Suitable promoters which operate in plants include the Cauliflower Mosaic Virus 35S (CaMV 35S) gene promoter that is expressed at a high level in virtually all plant tissues, the cauliflower meri 5 promoter that is expressed in the vegetative apical meristem as well as several well localised positions in the plant body, e.g. inner phloem, flower primordia, branching points in root and shoot and the *Arabidopsis thaliana* LEAFY promoter that is expressed very early in flower development. Other promoters include the rice actin promoter, tomato fruit-specific E8 promoter and flower specific promoter *APETALA*3 are suitable for the purpose.

The promoter may include one or more sequence motifs or elements conferring developmental and/or tissue specific regulatory control of expression.

Thus the vectors according to the invention may comprise a nucleotide sequence having at least 80% sequence identity (or higher as disclosed herein) to SEQ-ID No. 1, in addition to various sequences required to give them replicative, integrative and/or expression functionality. Such vectors can be used, for instance, to make plants into which they are introduced resistant to UV-B irradiation.

According to an aspect of some embodiments of the present invention a nucleic acid construct comprising a promoter that functions in plant cells is provided, operably linked to the nucleic acid sequence SEQ-ID No.1.

Conferring UV-B tolerance of FPT2 and by implication of compounds according to general formula (I) in plants was surprisingly proven by achieving an increased seed yield of FPT2-C24 overexpressing lines (FPT2C24-OX—FIG. 9*b*) and the gain-of-function NIL N09, in comparison to the non-producing wildtype Col0 as well as to the flavonoid less tt4 mutant lines, while being subjected to a range of UV-B treatments. The vigor of the NIL N09 and FPT2-C24 overexpressing lines was reflected in the number of leaves and inflorescences these lines produced (FIG. 9*a*).

The seed yield was considerably higher in the producing line (FPT2C24-OX) and the gain-of-function line (NIL N09) but also the germination rate of the seeds was doubled (FIG. 9*c*), revealing that the production of germinable seeds was almost five times higher in the gain-of-function (NIL N09) line and the C24-FPT2 overexpressing line than in lines that do not produce compounds according to general formula (I) (FIG. 9*c*).

Thus, another aspect of the present invention is related to a method of conferring UV-B tolerance to a plant, wherein the method comprises the steps of:
  (i) transforming a recipient plant with a vector comprising the nucleic acid sequence SEQ-ID No.1;
  (ii) producing one or more transgenic offspring of the recipient plant; and
  (iii) selecting the offspring for UV-B tolerance.

Thus, another aspect of the present invention is related to a method of conferring UV-B tolerance to a plant, wherein the method comprises the steps of:
  (i) transforming a recipient plant with a vector comprising a nucleic acid sequence having at least 80% sequence identity to SEQ-ID No.1;
  (ii) producing one or more transgenic offspring of the recipient plant; and
  (iii) selecting the offspring for UV-B tolerance.

Thus, another aspect of the present invention is related to a method of conferring UV-B tolerance to a plant, wherein the method comprises the steps of:
  (i) transforming a recipient plant with the nucleic acid according to claim 6 or 7 or the vector according to claim 8 or 9;
  (ii) producing one or more transgenic offspring of the recipient plant; and
  (iii) selecting the offspring for UV-B tolerance.

The sequence identity may be higher than 80% as disclosed herein so that any other of the sequence identity values as discloses herein can be used instead of the 80%.

The particular choice of a transformation technology will be determined by its efficiency to transform certain plant species as well as the experience and preference of the person practicing the invention with a particular methodology of choice. It will be apparent to the skilled person that the particular choice of a transformation system to introduce nucleic acid according to the invention into plant cells is not essential to or a limitation of the invention, nor is the choice of technique for plant regeneration.

As used herein, the phrase "UV-B tolerance" refers to genetically modified organisms, withstanding UV-B irradiation without damage of RNA, DNA or proteins for a period of time, compared to wildtype organisms. Thus, "UV-B tolerance" can for example be assessed by measuring vital parameters, known to a person skilled in the art, of organisms after UV-B irradiation treatment for 2 h per day for 28 days with 1000 mW/m$^2$.

As used herein, the phrase "UV-B tolerant plant" refers to genetically modified plants, withstanding UV-B irradiation without damage of RNA, DNA or proteins for a period of time, compared to wild type plants. Thus, "UV-B tolerance" of a plant can for example be assessed by measuring vital parameters, known to a person skilled in the art, of plants after UV-B irradiation treatment for 2 h per day for 28 days with 1000 mW/m$^2$.

Another aspect of the present invention is directed to a method for producing the compounds of general formula (I)-(IV) comprising expressing, overexpressing or synthesizing products of one or more nucleic acid molecules according to the invention in a host cell.

Therefore one preferred embodiment of the invention refers to a method for the preparation of at least one compound according to anyone of the general formulae (I)-(IV) using a UV-B tolerant plant comprising a nucleic acid that encodes a polypeptide which is suitable to synthesize a compound of anyone of the general formulae (I)-(IV) and wherein said nucleic acid has been introduced into the UV-B tolerant plant by genetic manipulation. In other words one preferred embodiment of the invention refers to a method for preparation of at least one compound according to anyone of the general formulae (I)-(IV) using a transgenic UV-B tolerant plant, wherein a nucleic acid which has been introduced into the UV-B tolerant transgenic plant codes for an enzyme suitable for synthesizing of at least one compound according to anyone of the general formulae (I)-(IV), preferably coding for FPT2. In general a host, preferably a plant such as a tobacco plant or an *Arabidopsis* line, is transformed to introduce a nucleic acid construct coding for the enzyme FPT2, such as a construct comprising the SEQ ID No. 1 and a suitable promotor. The introduced nucleic acid construct results in a transgenic plant, which overexpresses the enzyme FPT2 or which expresses the enzyme FPT2 only because of the introduced (transformed) nucleic acid construct.

The present invention is also directed to a method for producing the compounds of any one of the general formulae (I)-(IV) comprising expressing, overexpressing or synthesizing products of one or more nucleic acid molecules according to the invention in a host cell, wherein the host cell is a plant cell.

According to an aspect of some embodiments of the present invention a transgenic or genetically modified UV-B tolerant plant comprising a vector according to the present invention is provided, wherein the UV-B tolerant plant synthesizes the inventive compounds of anyone of the general formulae (I)-(IV). This means the plant has an improved UV-B tolerance because of introduction of the nucleic acid construct coding for the flavonol phenylacyltransferase by genetic manipulation, such as transformation. Therefore, one embodiment of the present invention is a UV-B tolerant transgenic plant comprising the nucleic acid sequence according to claim 6 or 7 or the vector according to claim 8 or 9 that synthesizes a compound of anyone of the general formulae (I)-(IV) and wherein the nucleic acid according to claim 6 or 7 or the vector according to claim 8 or 9 has been introduced into the UV-B tolerant transgenic plant by genetic manipulation. It is thereby preferred that the UV-B tolerant plant of the invention contains a vector comprising sequence ID No.1. Methods for transformation of plants, such as gene gun or viral infection, are commonly known in the art.

According to an aspect of some embodiments of the present invention an UV-B tolerant plant comprising a vector according to the present invention is provided, wherein the UV-B tolerant plant displays enhanced synthesis of the inventive compounds of anyone of the general formulae (I)-(IV).

As used herein, the term "enhanced" or "enhancing" refers to an increase in production of a compound according to anyone of the general formulae (I)-(IV), for example, by at least 5%, 10%, 15%, 20%, 30%, 50%, 100%, 200%, 250%, 400% or more. The increase in production of a compound according to general formula (I) may be in the emission level or in the internal pool level and can typically be determined with respect to a native plant (i.e., a plant not modified with the biomolecules of the invention, i.e. a non-genetically modified plant of the same species which is grown under the same growth conditions). The enhanced production of a compound according to anyone of the general formulae (I)-(IV) may be determined by any method known to one of ordinary skill in the art, as for example by headspace sampling, solvent extraction, solid phase micro extraction and the analysis by gas chromatography-mass spectrometry or any other analytical instrument.

According to an aspect of some embodiments of the present invention a transgenic or genetically modified UV-B tolerant plant comprising a nucleic acid construct according to the invention is provided, wherein the UV-B tolerant plant or the UV-B tolerant transgenic plant synthesizes at least one inventive compound of one of the general formulae (I)-(IV).

According to an aspect of some embodiments of the present invention a transgenic or genetically modified UV-B tolerant plant comprising a nucleic acid construct according to the invention is provided, wherein the UV-B tolerant plant display synthesis or enhanced synthesis of at least one inventive compound of anyone of the general formulae (I)-(IV).

Thereby the synthesis or enhanced synthesis is caused by a genetic manipulation. It is preferred that this genetic manipulation introduces said nucleic acid construct. This means the synthesis of at least one inventive compound of anyone of the general formulae (I)-(IV) is increased compared to the wildtype plant without said nucleic acid construct of the present invention.

Thus, a further aspect of the present invention is directed to a UV-B tolerant plant comprising the nucleic acid according to claim 6 or 7 or the vector according to claim 8 or 9 that synthesizes a compound according to anyone of the general formulae (I)-(IV) and wherein the nucleic acid according to claim 6 or 7 or the vector according to claim 8 or 9 has been introduced into the UV-B tolerant plant by genetic manipulation.

Another aspect of the present invention relates to a UV-B tolerant plant comprising the nucleic acid construct according to claim 12 that synthesizes a compound according to anyone of the general formulae (I)-(IV), wherein said nucleic acid construct has been introduced into the UV-B tolerant plant by genetic manipulation.

In another embodiment of the present invention purified or isolated nucleic acids or nucleic acid fragments complementary or antisense to the nucleic acids or nucleic acid fragments encoding FPT2 or functionally active fragments or variants thereof are provided. The present invention also provides substantially purified or isolated nucleic acids or nucleic acid fragments encoding amino acid sequences for a class of proteins which are related to FPT2, or functionally active fragments or variants thereof. Such proteins are herein referred to as FPT2-like.

By a FPT2-like polypeptide is meant that either one or both of the following criteria apply: (i) the gene which encodes the polypeptide is expressed in a similar manner to FPT2, and (ii) the polypeptide has similar functional activity to FPT2.

Use of the Saiginols According to the Invention

According to an aspect of some embodiments of the present invention a composition comprising the compound according to anyone of the general formulae (I)-(IV) is provided, optionally containing a cosmetically-acceptable carrier or excipient.

According to an aspect of some embodiments of the present invention a composition containing an inventive compound according to anyone of the general formulae (I)-(IV) for use as sunscreen is provided.

According to an aspect of some embodiments of the present invention a composition containing an inventive compound according to anyone of the general formulae (I)-(IV) for protection from UV-B radiation is provided.

According to an aspect of some embodiments of the present invention compounds according to anyone of the general formulae (I)-(IV) for use as UV-B protectants is provided.

According to an aspect of some embodiments of the present invention compounds according to anyone of the general formulae (I)-(IV) for use as UV-B protectants in a sunscreen is provided.

Another aspect of the present invention is the use of the compounds according to anyone of the general formulae (I)-(IV) in a sunscreen composition. Further provided is the cosmetic use of compounds according to the present invention as UV-B protectants.

The concentration of the compounds according to anyone of the general formulae (I)-(IV) in a composition according to the invention may be from about 0.1% by weight to about 10% by weight, preferably from about 0.5% by weight to about 5% by weight, preferably from about 0.5% by weight to about 2% by weight.

Compositions of the present invention may include a volatile solvent. By "volatile", as used herein, it is meant compounds that meet one or more of the following requirements: those compounds with a flash point below 150° C., such as less than about 130° C., such as less than about 50° C., such as less than about 25° C., and/or a boiling point of less than about 150° C., such as less than about 100° C., such as less than about 90° C.

By "solvent" it is meant, a compound that is capable (absent any other ingredients such as surfactants, co-solvents, etc.) of dissolving (e.g., forming a clear solution, such as one that transmits at least 25%, such as at least about 50% of light intensity of a 700 nm wavelength source through a 1 cm path length, as measured by conventional visible spectrophotometry) the compounds according to general formula (I). The volatile solvent is preferably cosmetically-acceptable and is preferably a liquid at room temperature. Furthermore, the volatile solvent is, in certain embodiments, miscible with water.

By "miscible with water", as used herein, it is meant that the volatile solvent is fully soluble in water in all proportions. Suitable examples of volatile solvents that are miscible with water include ethanol, propanol, and isopropanol. The volatile solvent, if not miscible with water, may, in certain embodiments, be soluble to at least some extent in isopropanol.

The amount of volatile solvent present in the composition may be from 10% to 60%, or from 20% to 55%, or from 30% to 50%. In certain embodiments, it is preferred if titanium oxide is present in the composition from 10% to 25%.

The composition of the invention can also comprise active materials and/or beneficial agents, such as conditioning agents, moisturising agents, emollients, astringent or antiperspirant compounds, biocidal compounds, sunscreens or UV absorbers, pigments, perfumes, anti-aging agents, enzymes, proteins, and vitamins.

As moisturizing agents can be mentioned for example glycerol, sorbitol, urea, collagen, gelatine, aloe vera, and hyaluronic acid. They can represent up to about 10% of the total weight of the composition.

In embodiment, where at least one emollient is present, the at least one emollient is preferably selected from alkylmonoglycerides, alkyldiglycerides, triglycerides such as oils extracted from plants and from vegetables (e.g., palm oil, coprah oil, cottonseed oil, soya bean oil, sunflower seed oil, olive oil, grapeseed oil, sesame oil, peanut oil, castor oil) or oils of animal origin (e.g., tallow, fish oils, etc.), derivatives of these oils such as hydrogenated oils, lanolin derivatives, mineral oils or paraffin oils, perhydrosqualane, squalene, diols such as 1,2-propanediol, 1,3-butanediol, cetyl alcohol (also referred to as 1-hexadecanol), stearyl alcohol, oleic alcohol, polyethylene glycols or polypropylene glycols, fatty esters such as isopropyl palmitate, 2-ethylhexyl cocoate, myristyl myristate, esters of lactic acid, stearic acid, behenic acid, isostearic acid, silicone oils such as polydimethylsiloxanes, silicone copolyols (dimethicone copolyol, cetyldimethicone copolyol), diphenyl-dimethicones, phenyltrimethicones, dimethiconols, with viscosities in the range about 20 to about 10000 mPa*s. They can represent up to about 20% by weight of the composition.

Flavour, essential oils, perfumes can for example include benzaldehyde, caraway oil, cardamon oil, cinnamon oil, ethylvanilin, *eucalyptus globulus* oil, glutamic acid, clove oil, orange oil, peppermint oil, thymol, phenethyl alcohol or their mixtures. They can represent up to about 3% of the total weight of the composition.

Proteins can for example include collagen, collagen derivatives and keratin. They can represent up to about 3% of the total weight of the composition.

Retinol, retinyl palmitate, tocopherol, tocopherol acetate, menadione, ascorbic acid and ascorbyl palmitate are examples of vitamins that can be included in the present compositions. They can represent up to about 0.5% of the total weight of the composition.

In another embodiment of the composition according to the invention said composition is in form of a cream, lotion, liquid or gel, with the effectiveness of a sunscreen.

Another aspect of the present invention is a composition for use as sunscreen comprising:
 a. Compounds according to general formula (I) in an amount from 0.1% to 10% of the total weight of the composition b. A volatile solvent in an amount of 10% to 60% of the total weight of the composition
c. Titanium oxide in an amount from 10% to 25% of the total weight of the composition
d. Moisturizing agents in an amount up to 10% of the total weight of the composition
e. Emollients in an amount up to 20% of the total weight of the composition
f. Proteins in an amount up to 3% of the total weight of the composition
g. Flavour in an amount up to 3% of the total weight of the composition
h. Vitamins in an amount up to 0.5% of the total weight of the composition It is clear to a skilled person that all ingredients of the sunscreen shall add up to 100% by weight.

An exemplary sunscreen composition containing the following components can be prepared according to the invention. Such a sunscreen may contain as active ingredients 15%-25% by weight titanium oxide and 5.0%-10.0% by weight saiginol A and may contain as inactive ingredients 50%-70% by weight ethanol, 2.0%-3.0% by weight hyaluronic acid, 3.0%-7.0% by weight grape seed oil, 1.5%-3.5% by weight sesame oil, 1.5%-3.5% by weight sunflower seed oil, and 0.05%-0.15% by weight tetrahexyldecyl ascorbate.

A quality of the instant composition is that the compounds according to general formula (I) have a critical wavelength of about 280 nm or greater.

In another embodiment, the sunscreen composition according to the invention has an SPF of at least 20, preferably an SPF of at least 25, more preferably SPF of at least 30, an even more preferably an SPF of at least 35.

The abbreviation "SPF", as used herein, stands for "sunburn protection factor" (sometimes also referred to as "sun protection factor"). The SPF is a measure of how much solar energy (in particular by UV radiation) is required to produce sunburn on protected skin (i.e. in the presence of sunscreen) relative to the amount of solar energy required to produce sunburn on unprotected skin (i.e. without sunscreen). An increasing SPF value means that also sunburn protection increases. The SPF can be determined experimentally under reproducible conditions on a meaningful number of test subjects (see for example ISO 24444:2010).

In a preferred embodiment of the invention the composition can be used as cosmetics with sunscreen effect.

All transgenic lines shown have a Col0 background. FPT1(Col), FPT1(C24), FPT2-1(Col0), FPT2-2(Col0) and FPT2(C24) indicate FPT1 cloned from Col0 and C24, FPT2 cloned from Col0 (FPT2-1 is shortest transcript and FPT2-1 is longest transcript) and C24 respectively. The chromatograms show ion extracted chromatogram for saiginol A (945m/z), B & I (901m/z), D (799m/z), G (961m/z) and J (815m/z), respectively.

Figure 9:
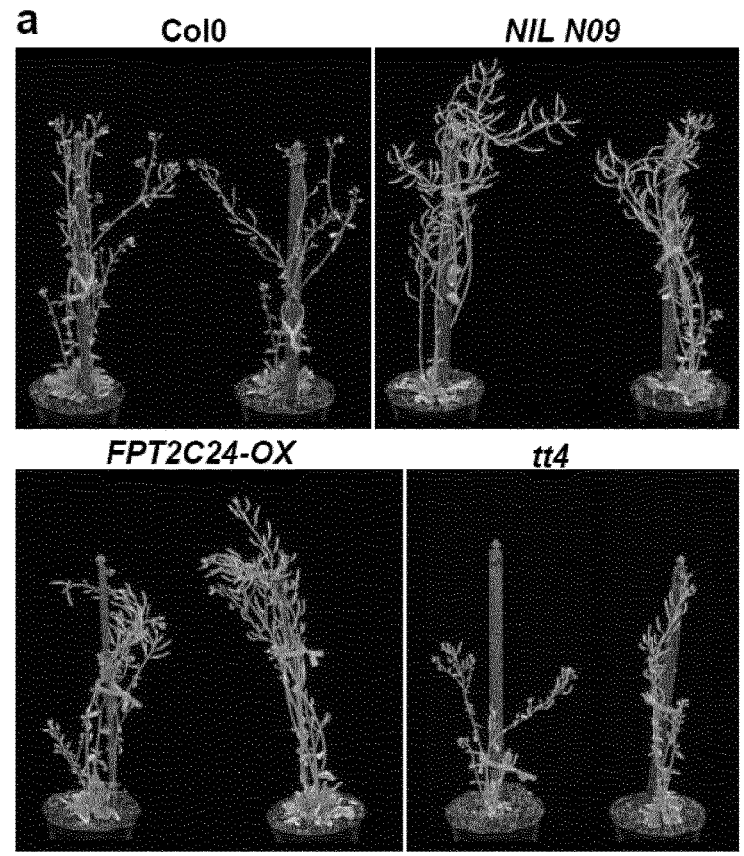
Figure 9:
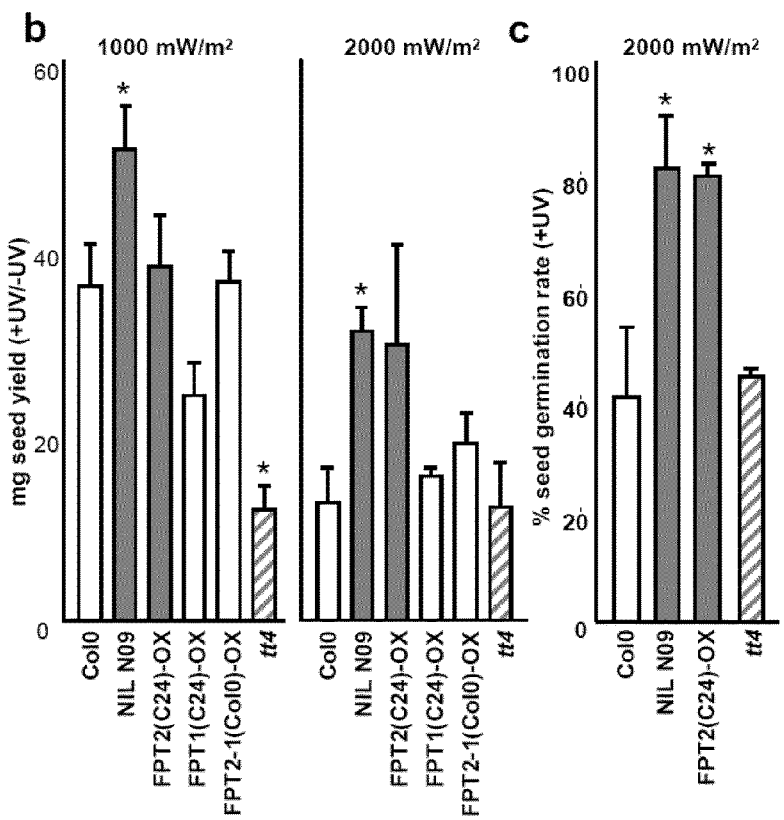

FIG. 9: Functional characterization of the role of saiginols in protection against UV-B irradiation.
  a) Representative photographs of the phenotypic changes of genotypes exhibiting modified flavonol contents following UV-B irradiation treatment (2h per day for 28 days with 1000 mW/m2 UV-B light irradiation)
  b) Seed yield after long-term (2 h per day for 28 days) UV-B treatment (1000 and 2000 mW/m2). Seeds were collected on a single plant basis but three individual plants per genotype were measured. Data is presented as mean+SE. *P<0.05.
  c) Germination rate using seeds obtained after UV-B irradiation (2h per day for 28 days with 2000 mW/m$^2$ UV-B light irradiation).

Figure 10:
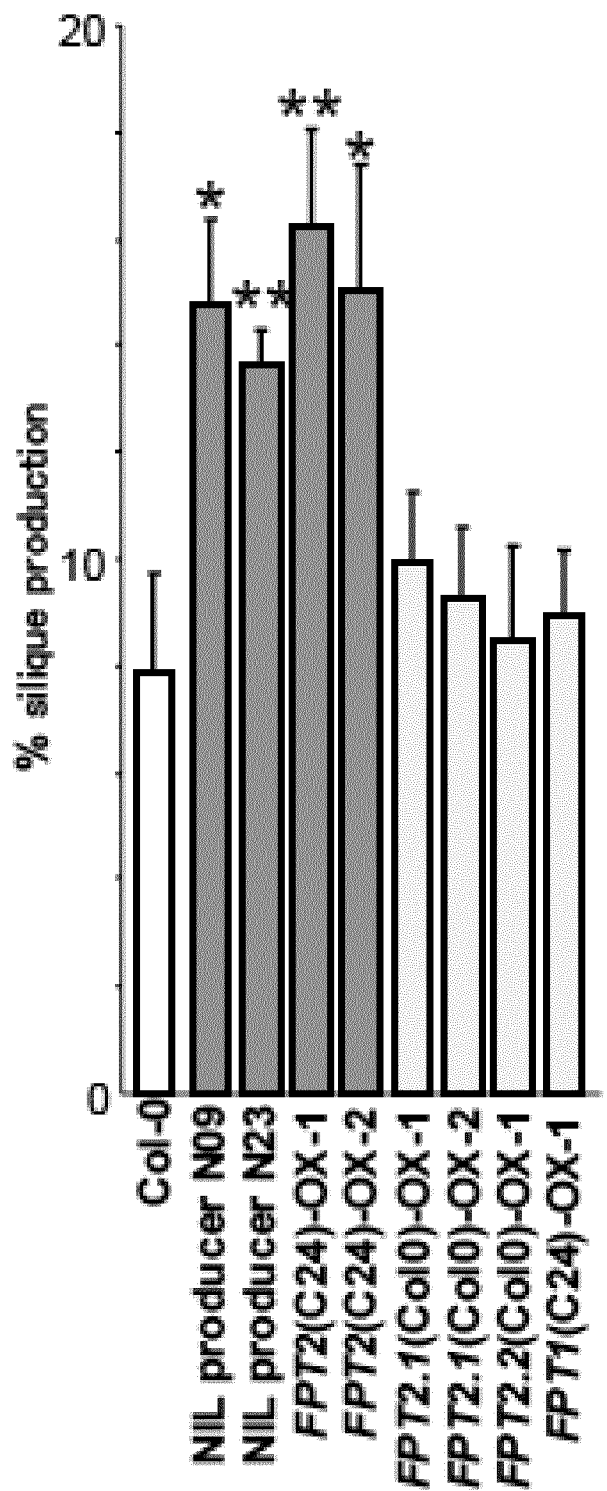

FIG. 10: Rate of silique production under UV-B irradiation after long-term (2 h per day) UV-B treatment (1 W/m$^2$) using the detached immature inflorescences of first bolting. Error bars indicate the SE of six biological replicates. Data is presented as mean±S.E.M. *P<0.05. Abbreviation foe indication of plant lines is as written in example 10. OX-1 and OX-2 designate independent overexpressing lines using the same construct.

Figure 11:
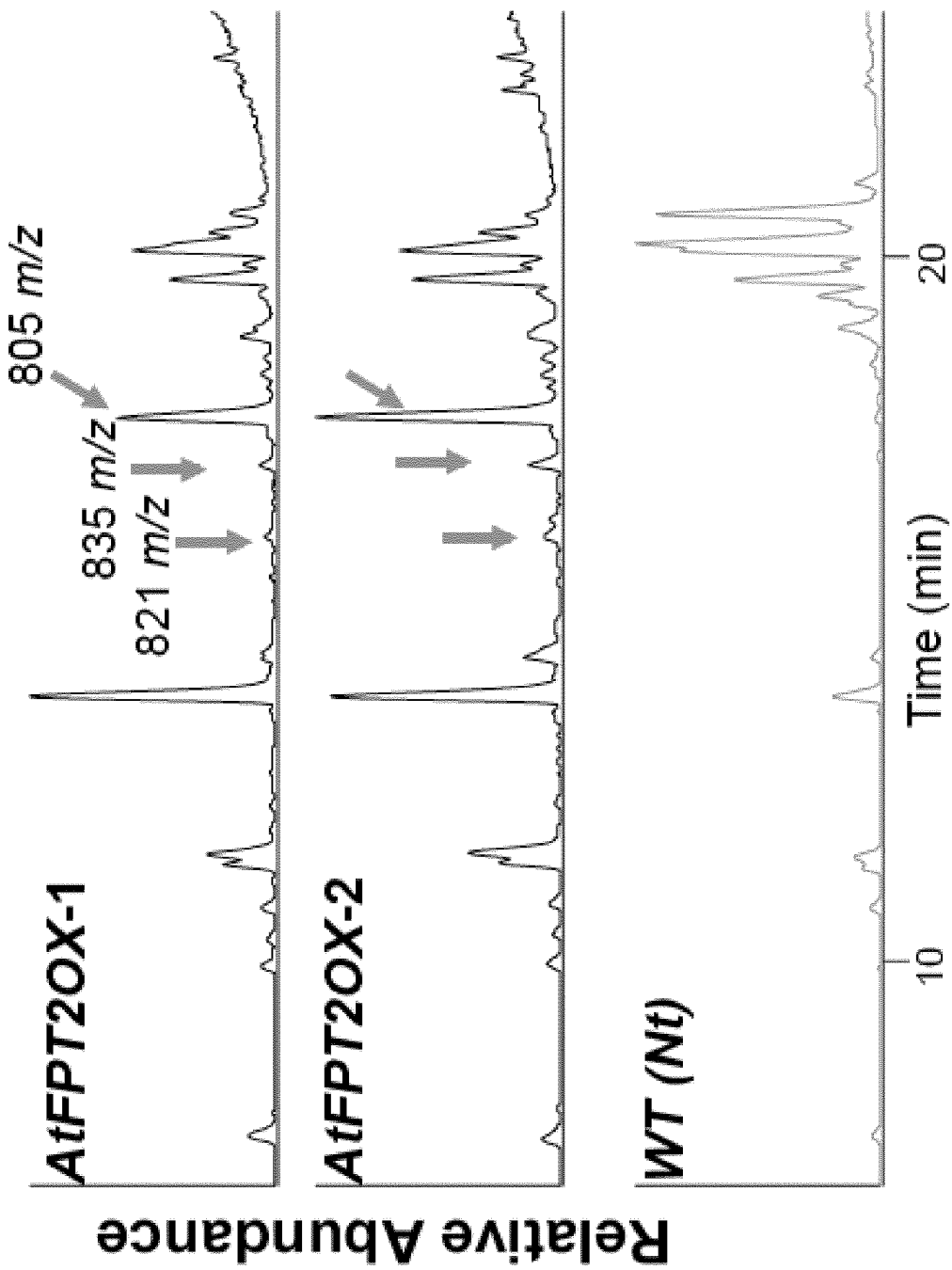

FIG. 11: AtFPT2 overexpressing transgenic tobbaco plants.
  Three metabolites (805, 821, 835 m/z), which are annotated phenyacylated flavonol-glycosides were observed in AtFPT2-OX tobacco transgenic plants. This figure shows results of example 13.

EXAMPLES

Plant Material
Accessions of *Arabidopsis thaliana* used in the present application were obtained from NASC the European *Ara-* bidopsis Stock Centre. Plants were cultured on agar plates in a growth chamber under normal long day light conditions (16 h day, 140-160 µmol photons m−2 −s 1, 20° C.; 8 h night, 16° C.) for 14 days and transferred to 10 soil. Flower materials were harvested from individual plants, immediately frozen in liquid nitrogen, and stored at −80° C. until further use.

Example 1: Secondary Metabolite Profiling by LC-MS

Given that considerable evidence has accumulated concerning the UV-B protective function of various phenylpropanoids during the processes of flower development, pollination and seed production assessment of levels of various phenylpropanoids in flowers in a set of 72 *Arabidopsis* ecotypes, which provided good coverage of the overall natural variability of the species, was performed by the inventors. Application of liquid chromatography-mass spectrometry (LC-MS) resulted in the detection of a total of 67 peaks consisting of 21 flavonoids, 12 glucosinolates, five hydroxycinnamates, eight polyamines, three putative lipid derivatives and 18 peaks of unknown chemical structure. All data were processed using Xcalibur 2.1 software (Thermo Fisher Scientific, Waltham, USA). Peak identification and annotation were performed in a combination approach using standard chemical confirmation, MSMS profiling, retention time profiling, mutant analysis, literature survey. In order to carry out mutant analysis for flavonoid derivatives, 14 mutants; ugt78d2 mutant (flavonoid-3-O-glucoside-less), tt7 mutant (quercetin and isorhamnetin derivatives-less), ugt78d1 mutant (flavonol-3-O-rhamnosides-less), ugt78d3 mutant (flavonol-3-O-arabinosides-less), omt1 mutant (isorhamnetin-derivatives-less), ugt89c1 mutant (flavonol-7-O-rhamnosides-less), tt4 mutant (all flavonoid-less), and pap1-D mutant (anthocyanin-overaccumulator), and La-er background tt mutant series obtained from NASC (tt3, tt4, tt5, tt6) were used.

Example 2: Procedure of Purification and Characterization of Saiginol A

MS-MS fragmentation studies suggested that these 18 peaks of unknown identity from Example 1 are novel flavonol derivatives. In order to characterize the chemical structure of these peaks, large amounts of the *Arabidopsis* accession C24, which accumulated these compounds, were re-grown and processed.

Column chromatography was carried out over ODS (Nacalai Tesque, Cosmosil 75C18-OPN). HPLC analysis was carried out on an Atlantis® (ϕ4.6×150 mm, Waters) at a flow rate of 0.5 ml min$^1$. Preparative HPLC was performed on a LC 10A system (Shimadzu) using an Inertsil® ODS-EP 5 m ($6.0×150 mm) at 30° C. and monitoring was accomplished by PDA (200-600 nm). HPLC-PDA-ESI-MS (HPLC/photodiode array detection/electrospray ionization mass spectrometry) was performed on a Finnigan LCQ-DECA mass spectrometer (ThermoQuest, San Jose, Calif., USA) and an Agilent HPLC 1100 series (Agilent Technologies, Palo Alto, Calif., USA). HR-ESI-MS was performed on an Exactive™ mass spectrometer (ThermoQuest, San Jose, Calif., USA). Optical rotations were determined on a JASCO P-1020. UV spectra were recorded on a JASCO V-560. NMR data were recorded on JEOL JNM ECP-600. The deuterated solvent CD3OD was used for peak 4. Coupling constants are expressed in Hz.

Plant Materials, Extraction and Purification

Plant samples (26.72 g fresh weight) were harvested and immediately frozen in liquid nitrogen, the whole of which was immediately extracted with methanol. After concentration, MeOH liquid extraction was extracted with n-hexane, $CHCl_3$ to remove low polarity metabolites. After the liquid-liquid partition and concentration, MeOH soluble fraction was obtained and was dissolved with $H_2O$. After liquid-liquid partition with n-BuOH, the n-BuOH fraction was obtained (256.9 mg).

This fraction was applied to ODS column (4 3.5×7 cm), and roughly separated by eluting with a gradient of $H_2O$ as solvent A and $CH_3CN$ as solvent B and the following elution profile [fraction 1: 0% $CH_3CN$, fraction 2: 10% $CH_3CN$, fraction 3: 20% $CH_3CN$, fraction 4: 30% $CH_3CN$, fraction 5: 40% $CH_3CN$, fraction 6: 50% $CH_3CN$, fraction 7: 60% $CH_3CN$, fraction 8: 70% $CH_3CN$, fraction 9 80% $CH_3CN$ and fraction 10: 100% $CH_3CN$ (elution solvent: 70 ml/fraction)] to give 10 fractions. After LC-MS analysis for trace of peak 4, fraction 2 to 4 was assembled (fraction A). Fraction A was applied to ODS column (ϕ3.5×7 cm) again, and separated by eluting with a gradient of $H_2O$ as solvent A and $CH_3CN$ as solvent B and the following elution profile [fraction A-1 and A-2: 0% $CH_3CN$, fraction A-3 and A-4: 10% $CH_3CN$, fraction A-5 to A-7: 20% $CH_3CN$, fraction A-8 to A-11: 30% $CH_3CN$ and fraction A-12: 100% $CH_3CN$ (elution solvent: 30 ml (fraction A-1 to A-5), 15 ml (fraction A-6 to A-12) to give 12 fractions.

After LC-MS analysis for trace of peak 4, fraction A-10 and A-11 were assembled (fraction B). Fraction B (12.0 mg) was applied to preparative HPLC using an isocratic elution (20% $CH_3CN$ in $H_2O$) at a flow rate of 4 ml/min to give peak 4 (3.5 mg).

Characterization of Saiginol A

Kaempferol-3-O-[2-O-(α-L-rhamnopyranosyl)-6-O-(sinapoyl)-β-D-glucopyranoside]-7-O-α-L-rhamnopyranoside Yellow amorphous solid. $[α]_D^{20}$ −54.1° (c 0.09, MeOH). UV (MeOH): $λ_{max}$ (logs): 201.5 (3.47), 223.0 (3.61), 266.5 (3.37), 331.5 (3.47). HRESI-MS: m/z 969.2637 ([M+Na]$^+$, calcd. for $C_{44}H_{50}O_{23}Na$, 969.2635). $^1H$ NMR (CD$_3$OD) δ: 6.25 (1H, br.s, H-6), 6.41 (1H, br.s, H-8), 7.90 (2H, d, J=8.8 Hz, H-2' and H-6'), 6.85 (2H, d, J=8.8 Hz, H-3' and H-5') (kaempferol; H-6, 8, H-2' to 6'), 5.75 (1H, d, J=7.2 Hz, H-1), 3.63 (1H, m, H-2), 3.58 (1H, m, H-3), 3.32 (1H, m, H-4), 3.51 (1H, m, H-5), 4.26 (1H, m, H-6a), 4.40 (1H, m, H-6b) (glucose; H-1 to H-6a,b), 5.23 (1H, br.s, H-1), 3.99 (1H, m, H-2), 3.75 (1H, m, H-3), 3.32 (1H, m, H-4), 3.97 (1H, m, H-5), 0.90 (1H, m, H-6) (rhamnose 1; H-1 to H-6), 6.66 (2H, s, H-2), 6.06 (1H, d, J=16.0, H-7a), 7.28 (1H, d, J=16.0, H-813), 3.87 (6H, s, —OCH$_3$) (sinapic acid; H-2, H-7c, H-8P and —OCH$_3$), 5.33 (1H, br.s, H-1), 3.47 (1H, m, H-2), 4.04 (1H, m, H-3), 3.76 (1H, m, H-4), 3.47 (1H, m, H-5), 1.18 (1H, m, H-6) (rhamnose 2; H-1 to H-6). $^{13}C$ NMR (CD$_3$OD) δ: 161.7, 134.5, 179.7, 159.7, 99.9, 163.2, 96.4, 157.9, 107.5, 123.2, 132.5, 116.4, 163.0, 116.4, 132.5 (kaempferol; C-2 to C-10 and C-1' to C-6'); 100.2, 80.2, 79.2, 74.3, 76.1, 64.6 (glucose; C-1 to C-6); 102.8, 70.4, 72.5, 72.6, 72.6, 17.2 (rhamnose 1; C-1 to C-6), 12.75, 107.0, 148.5, 139.5, 149.5, 107.0, 115.6, 147.0, 168.7 (sinapic acid; C1- to C-9), 99.9, 71.4, 71.8, 72.3, 73.9, 19.3 (rhamnose 2; C-1 to C-6). HMBC correlations from the anomeric proton (Rha1H-1, 6 5.23) to C-2 of glucose, the protons (glucose H-6a,b, 6 4.26 and 4.40) to C-9 of sinapic acid and the anomeric proton (Rha2H-1, 6 5.33) to C-7 of kaempferol were observed.

Example 3: UV-B Absorption Profile of Saiginol A

Figure 1:
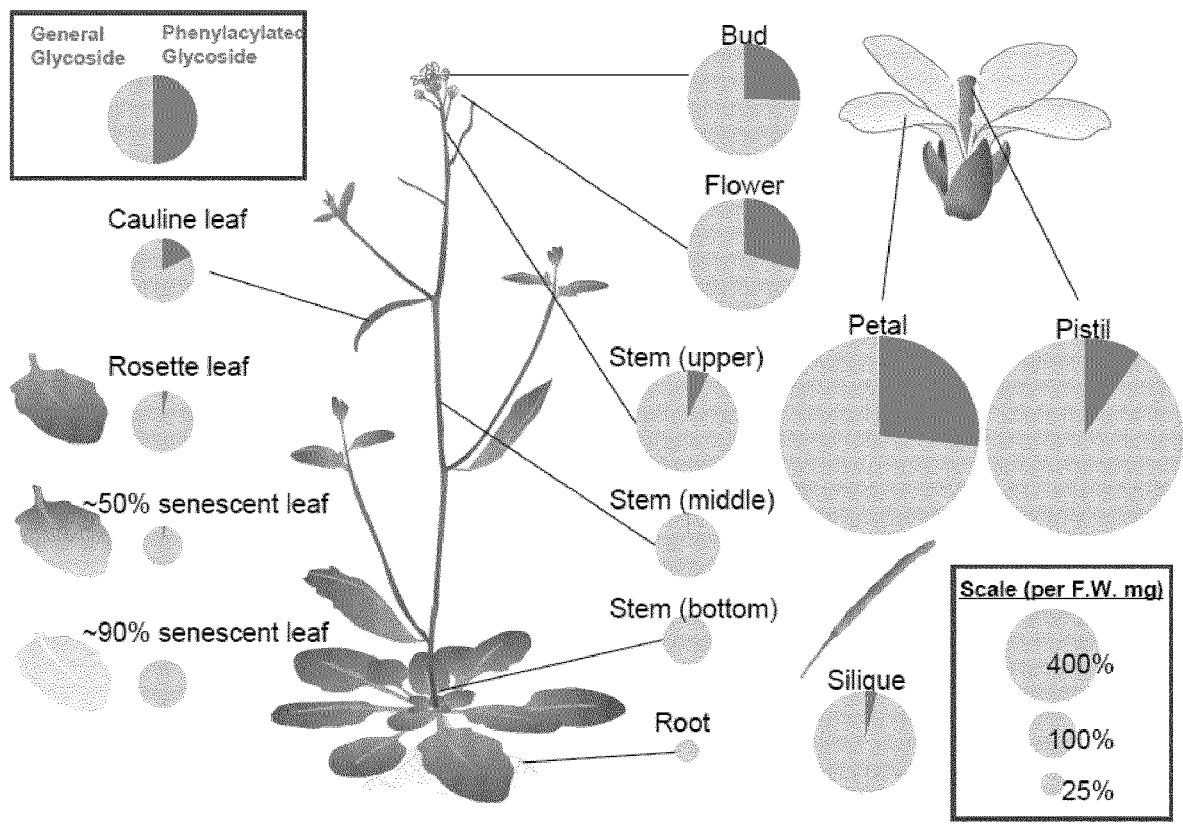
FIG. 1: Tissue specificity of the accumulation of saiginols. The relative ratio was estimated by using total peak area of general flavonol-glycosides and phenylacylated flavonol-glycosides.
Figure 2:
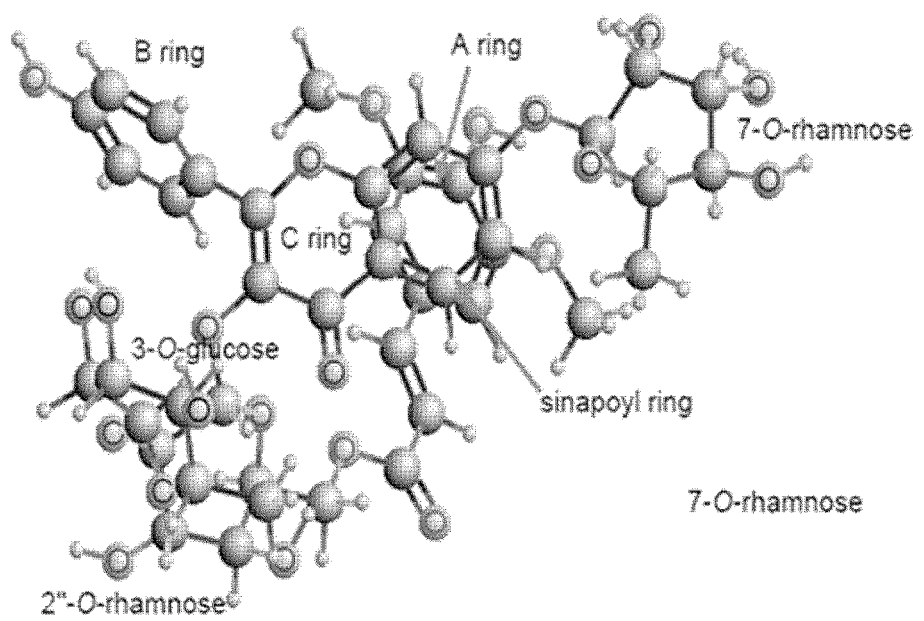
FIG. 2: Structural analysis of saiginol. A computational estimation of the most stable stereochemical structure of saiginol A is shown. The estimation was performed by MMFF94 of Marvin.
Figure 3:
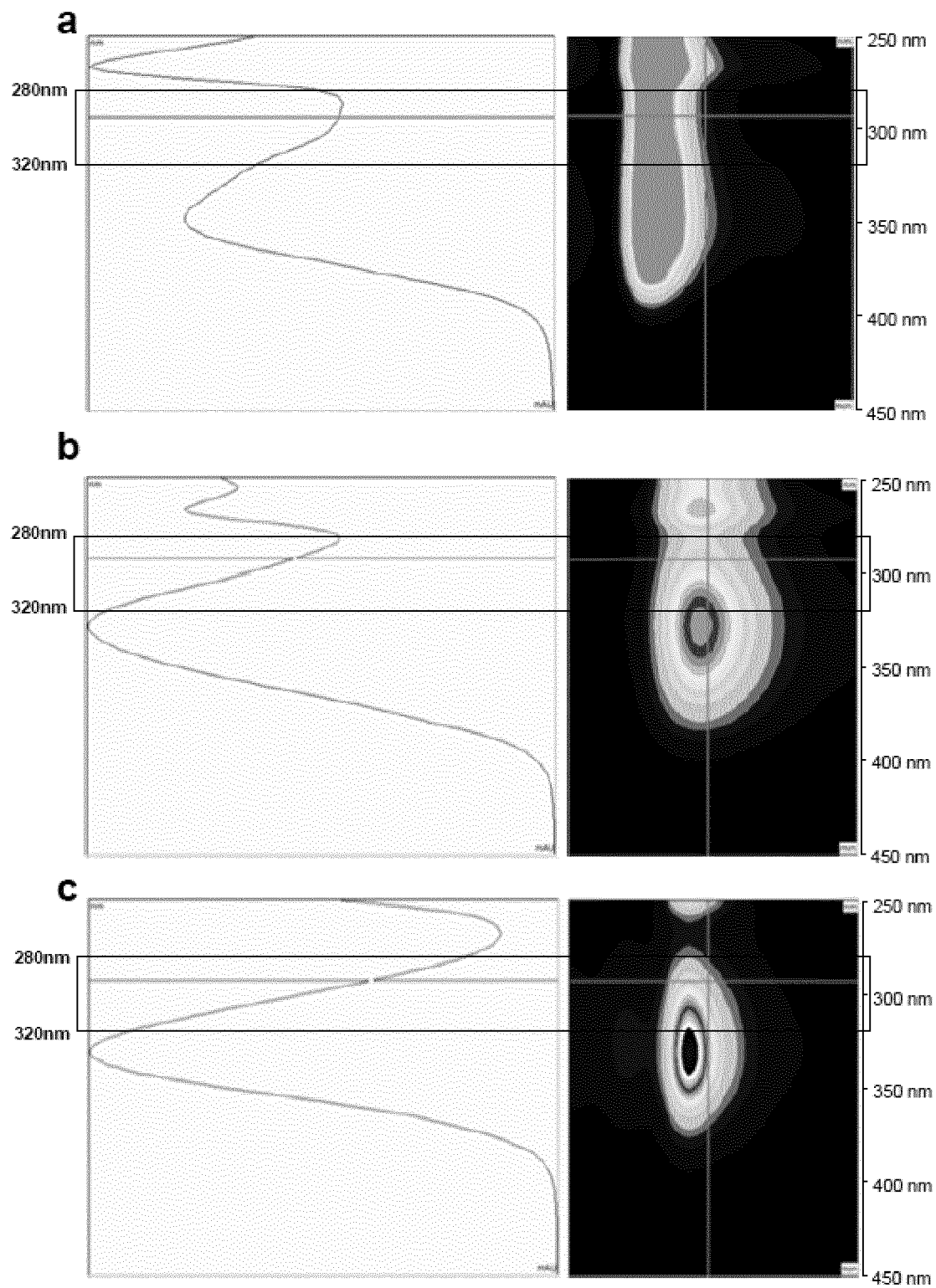
FIG. 3: Spectrometric analysis of saiginol. HPLC-PDA profiling of a) kaempferol-3-O-Glc-2"-O-Rha-7-O-Rha, b) saiginol A (kaempferol-3-O-Glc-2"-O-Rha-6"-sinapoyl-7-O-Rha) and c) sinapoyl-Glc in the spectral range between 260 nm and 450 nm.

UV-VIS spectra in the range between 260 nm and 450 nm were recorded and analyzed via HPLC-PDA profiling for kaempferol-3-Glc-2"-Rha-7Rha (FIG. 3A), saiginol A (kaempferol-3-Glc-2"-Rha-6"-sinapoyl-7Rha, FIG. 3B) and sinapoyl-glucose (FIG. 3C). HPLC-PDA (HPLC/photodiode array detection) was performed on Dionex Ultimate 3000 system (San Jose, Calif., USA). Column chromatography was carried out on a Luna® (ɸ 2.00×150 mm, phenomenex) at a flow rate of 0.2 ml min$^{-1}$ and monitoring was accomplished by PDA (200-600 nm).

The flavonol-glycoside kaempferol-3-Glc-2"-Rha-7Rha, a precursor of saiginol A, appeared to be much less efficient in UV-B absorption than the phenylacylated saiginol A (kaempferol-3-Glc-2"-Rha-6"-sinapoyl-7Rha)(see FIG. 3A, B). The UV-VIS spectra of a Saiginol A revealed a Amax at 201.5 (3.47), 223.0 (3.61), 266.5 (3.37) and 331.5 nm (3.47).

The substances kaempferol-3-O-Glc-2"-O-Rha-7-O-Rha and sinapoyl-Glc were purified and obtained from *Arabidopsis* plant extracts (Nakabayashi et al., 2008).

Example 4: Tissue Specificity of Saiginol Accumulation

Plant Material

*Arabidopsis* C24 plants were cultured on agar plates in a growth chamber under normal long day light conditions (16 h day, 140-160 µmol photons m$^{-2}$ s$^{-1}$, 20° C.; 8 h night, 16° C.) for 14 days and transferred to soil. Tissue materials were harvested and immediately frozen in liquid nitrogen, and stored at −80° C. until further use. Relative amount was compared and evaluated using detected peak area normalized by fresh weight material.

The inventive saiginols were predominantly present in floral tissues but also to a lesser extent in the stem, silique and the cauline leaf but are essentially, or maybe even totally, absent in rosette leaves, senescent leaves and the root (FIG. 4) suggesting that they accumulate in the tissues which are highly exposed to light irradiation and most important with respect to facility. Further detailed spatial analysis of flavonol profiles revealed that the inventive saiginols predominantly accumulate in the floral petal and to a lesser extent in the stamen and pistil, but are probably absent in pollen.

Example 5: Metabolite Quantitative Trait Loci (mQTL) Analysis for Saiginols

The inventors aimed to narrow down the genomic basis for the capability of accession C24 to produce the inventive saiginols, compared to the accession Col0 that is not capable to produce the inventive saiginols. Therefore, near Isogenic Lines (NILs) were obtained from the saiginol-producing accession C24 and the non-producing accession Col0 by reciprocal introgression as described previously (Torjek et al., 2008, J. Hered. 99, 396-406).

In Brief:

In order to create a desired NIL, a plant having the phenotype of interest (here accession C24 capable of saiginol production, also called "donor") is crossed with an accession not capable of saiginol production (here Col0, also called "background"). The result is a F1 generation having a genome that consists of 50% of the genome of C24 and 50% of the genome of Col0. During gametogenesis of this F1 generation, crossing-over occurs leading to Col0-derived chromosomes with substitutions from C24 and C24-derived chromosomes having substitutions from Col0. Several generations of backcrossing with the Col0 parent line (also called background) leads to daughter generations with a more and more reduced amount of genomic segments from C24 within the Col0 background. This process is also called reciprocal introgression. Here, *Arabidopsis* lines derived from Col0 containing genomic fragments of C24 were named "N lines". Vice versa, it is also possible to backcross the F1 generation with the C24 line leading to daughter generations with a more and more reduced amount of genomic segments from Col0 within the C24 background. In this case, the accession C24 would be the background line, and the accession Col0 the donor. Here, *Arabidopsis* lines derived from C24 containing genomic fragments of Col0 were named "M lines".

In total, 45 M lines (C24 background) and 69 N lines (Col0 background) were used for saiginol targeted mQTL analysis. The presence or absence of the inventive saiginols in the NILs was assessed by LC-MS (compare Example 1 and 2).

Figure 4:
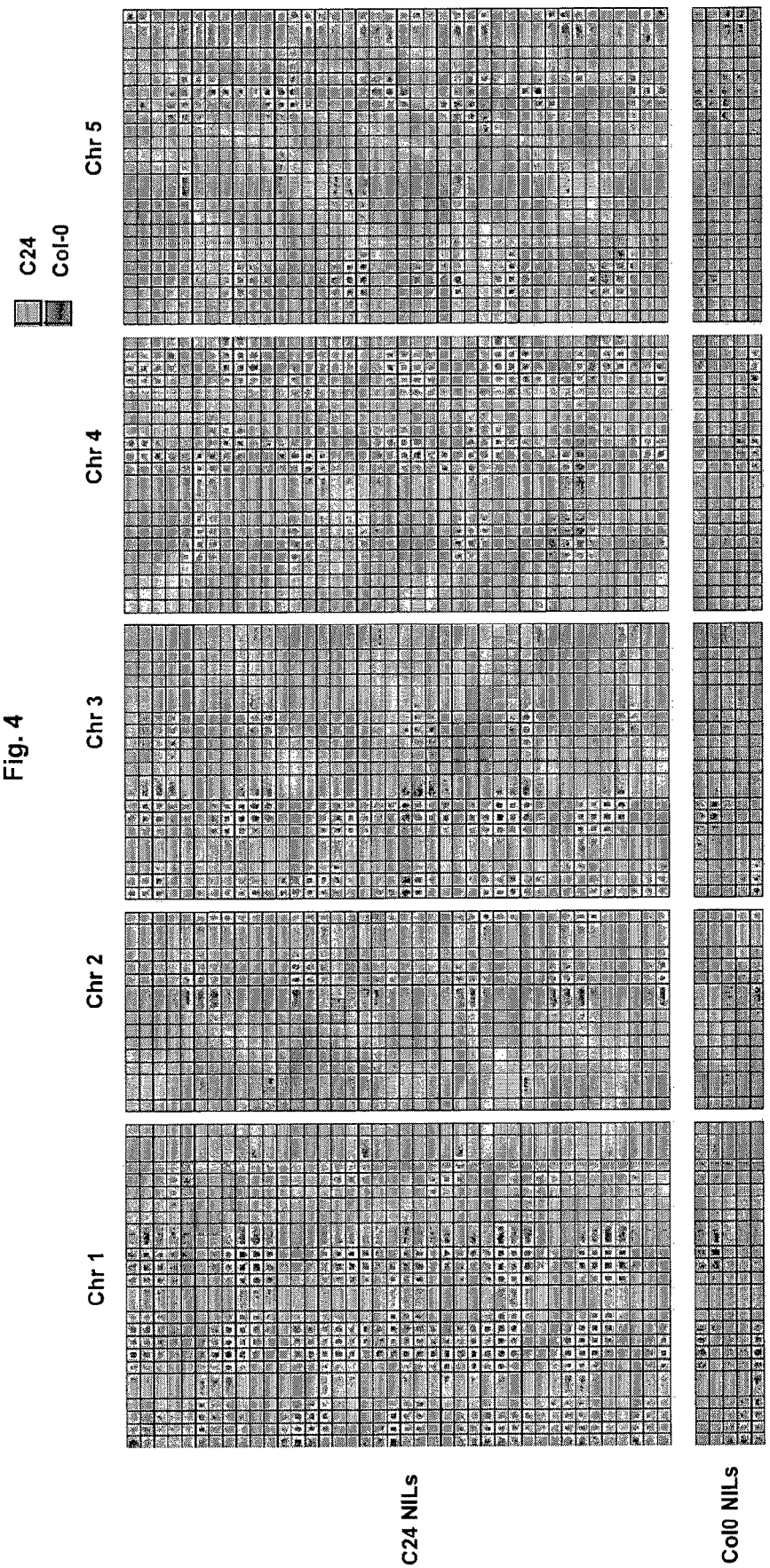
FIG. 4: Chromosomal mapping of metabolite Quantitative Trait Loci (mQTL) for saiginol production. The chromosomal region on chromosome 2 indentified to be responsible for saiginol production (At2g22230-At2g3160) is delimited by a frame.

Intriguingly, the inventors found a loss-of-function line in the NILs having a C24 background, i.e. a M line that is not capable of saiginol production (see NIL M16, FIG. 5 and FIG. 6 *b*), wherein the substituted genome segment (provided by Col0) mapped to chromosome 2 (At2g22230-At2g31610) as shown in FIG. 4.

Figure 5:
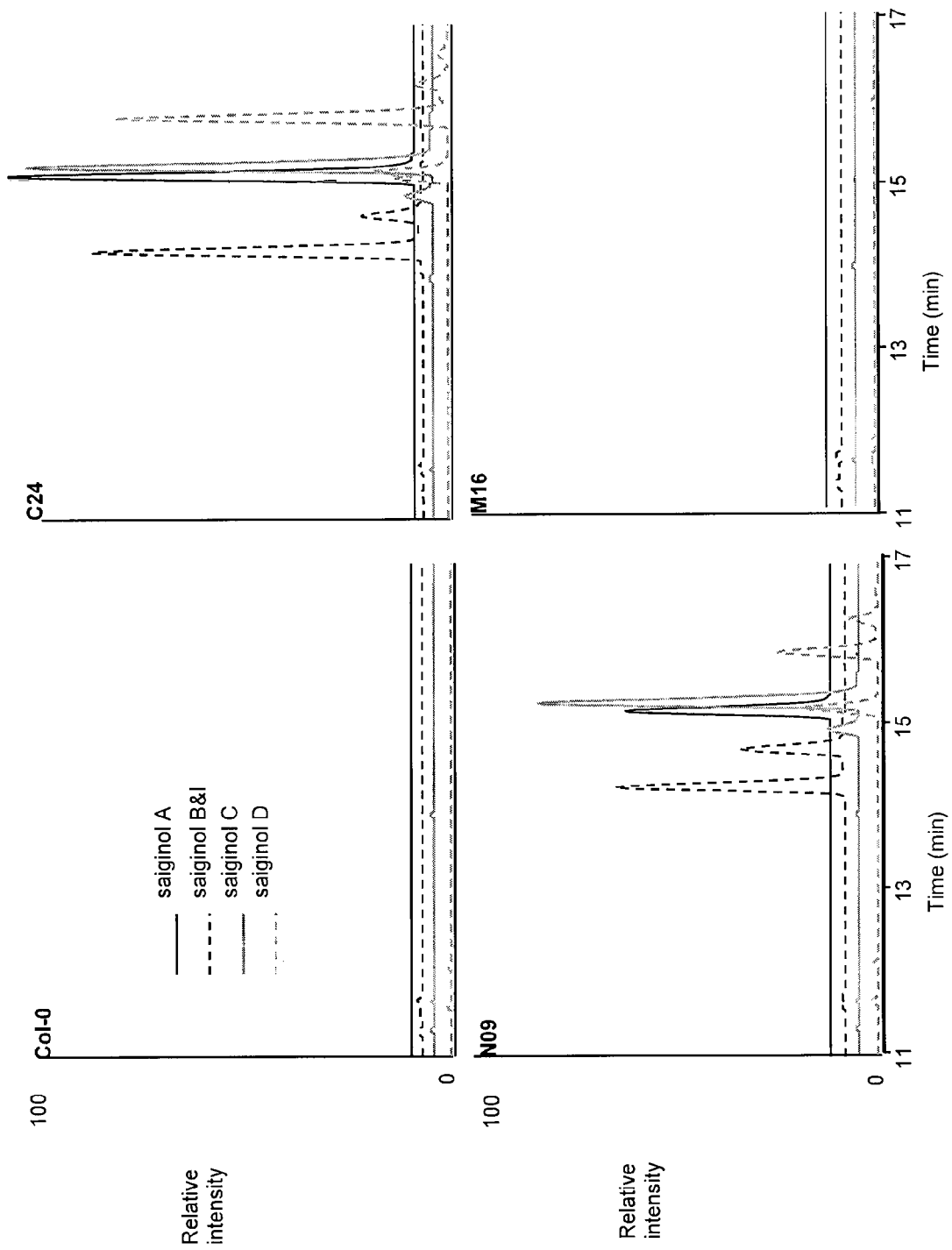
FIG. 5: Saiginol A production in near isogenic lines (NIL) of Col0 and C24 accessions. Chromatograms of gain-of-function and loss-of-function near isogenic lines (NIL) obtained from mQTL analysis of reciprocal crosses between Col0 and C24 are shown. N and M lines are Col0 and C24 background introgression lines, respectively. Chromatograms show ion extracted chromatograms for saiginol A (945m/z), B & I (901m/z), C (885m/z) and D (799m/z), respectively.
Figure 6:
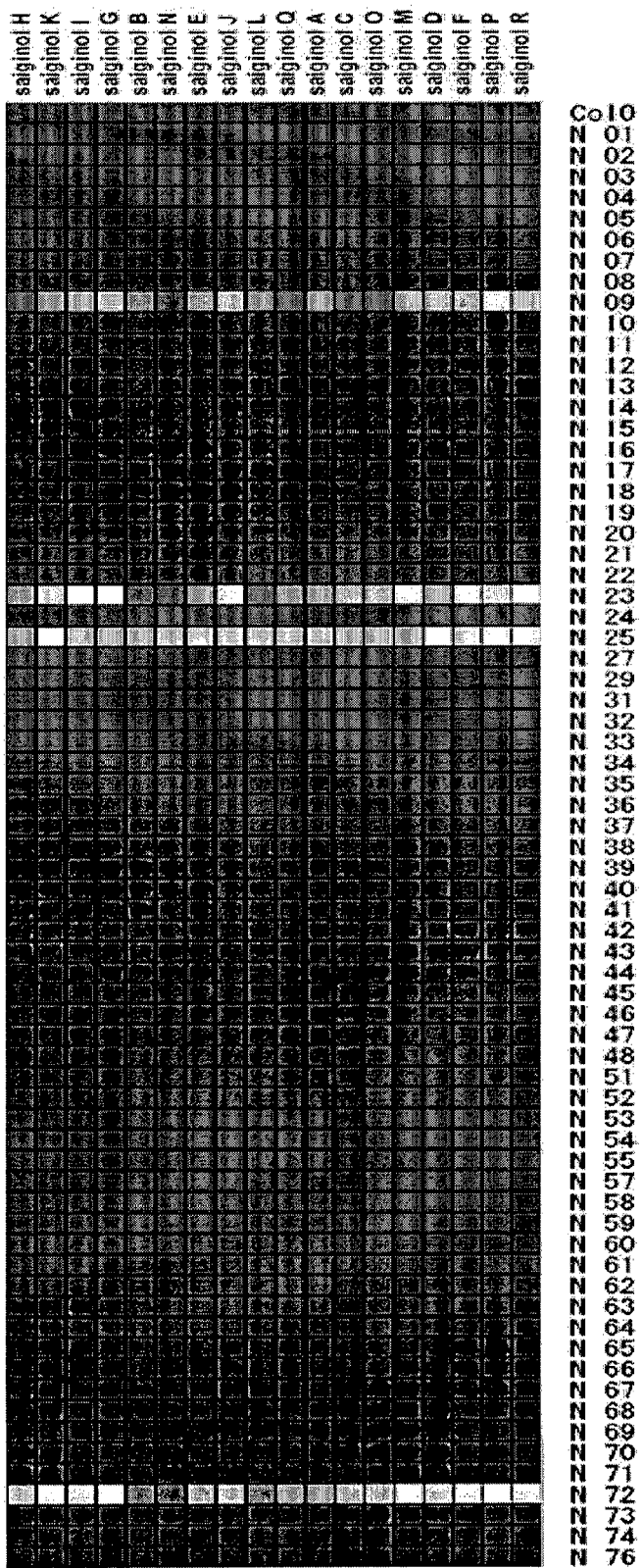
FIG. 6: mQTL analysis of saiginol A in near isogenic lines (NIL) of Col0 and C24 accessions. In total 45 M lines (C24 background) and 69 N lines (Col0 background) were used for saiginol targeted mQTL analysis. The heatmap shows values of saiginol A production displaying on a $\log_2$ scale divided by the average of all values.
Figure 6:
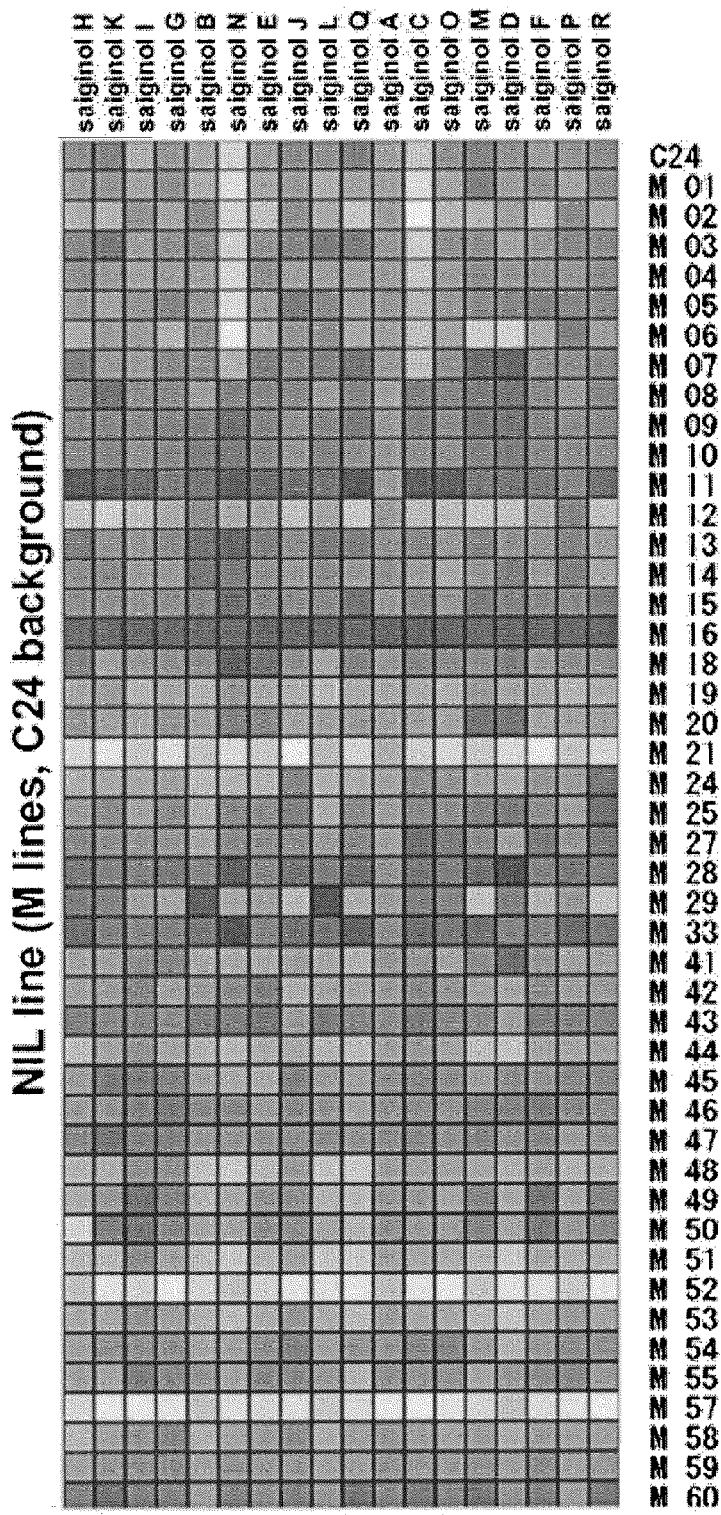

Interestingly a genomic substitution (provided by C24) in the same chromosomal segment led to a gain-of-function line within the NILs having a Col0 background, i.e. a N line that is now capable of saiginol production (see NIL N09, FIG. 5 and FIG. 6 *a*). Thus it can be concluded that a gene of accession C24 residing on chromosome 2 (At2g22230-At2g31610) is responsible to the production of the inventive saiginols.

O. Torjek et al. (2008): Construction and analysis of 2 reciprocal *Arabidopsis* introgression line populations. *J. Hered.* 99, 396-406.

Example 6: Transcript Profiling Via Microarray Analysis

The inventors further performed transcript profiling experiments in several accessions producing the inventive saiginols (among them C24) and in several accession not producing the inventive saiginols (among them Col0) in order to compare the gene expression between producers and non-producers in the region of chromosome 2 assigned to be relevant for saiginol production (see Example 2) to narrow down the genetic basics for saiginol production Transcriptome analysis was carried out using ATH1 microarrays as described previously. The experiment was performed with five producing accessions (C24, Cvi, Da, Rsch and RLD) and five non-producing accessions (Col0, La-er, Ws, Sap and Stw).

In brief, the total RNA was extracted from frozen plant materials (see above) of each accession used by using the RNeasy Plant Mini Kit (Qiagen) according to the manufacturer's instructions.

Subsequently, labelled target cRNA was prepared according to the manufacturer's instructions of the *Arabidopsis* Genome ATH1 DNA array (Affymetrix, Santa Clara, Calif., USA). For this, first double-stranded cDNA was prepared from 40 µg of total RNA by use of the SuperScript Choice System (invitrogen), again according to the manufacturer's instructions. Said cDNA was then transcribed in vitro using BioArray High Yield RNA Transcript Kit (Enzo, New York, N.Y., USA) into labelled cRNA.

Following purification and fragmentation, the labeled cRNA was hybridized to *Arabidopsis* Genome ATH1 GeneChip array in a Hybridization Oven model 640 (Affymetrix). Washing and staining of the GeneChips were carried out using GeneChip Fluidics Station model 400. Scanning of the GeneChips was carried out with gene Array Scanner (Agilent Technologies). Duplicate hybridisations were carried out for Col0 and C24, while for all other accessions a single hybridization was performed.

Figure 7:
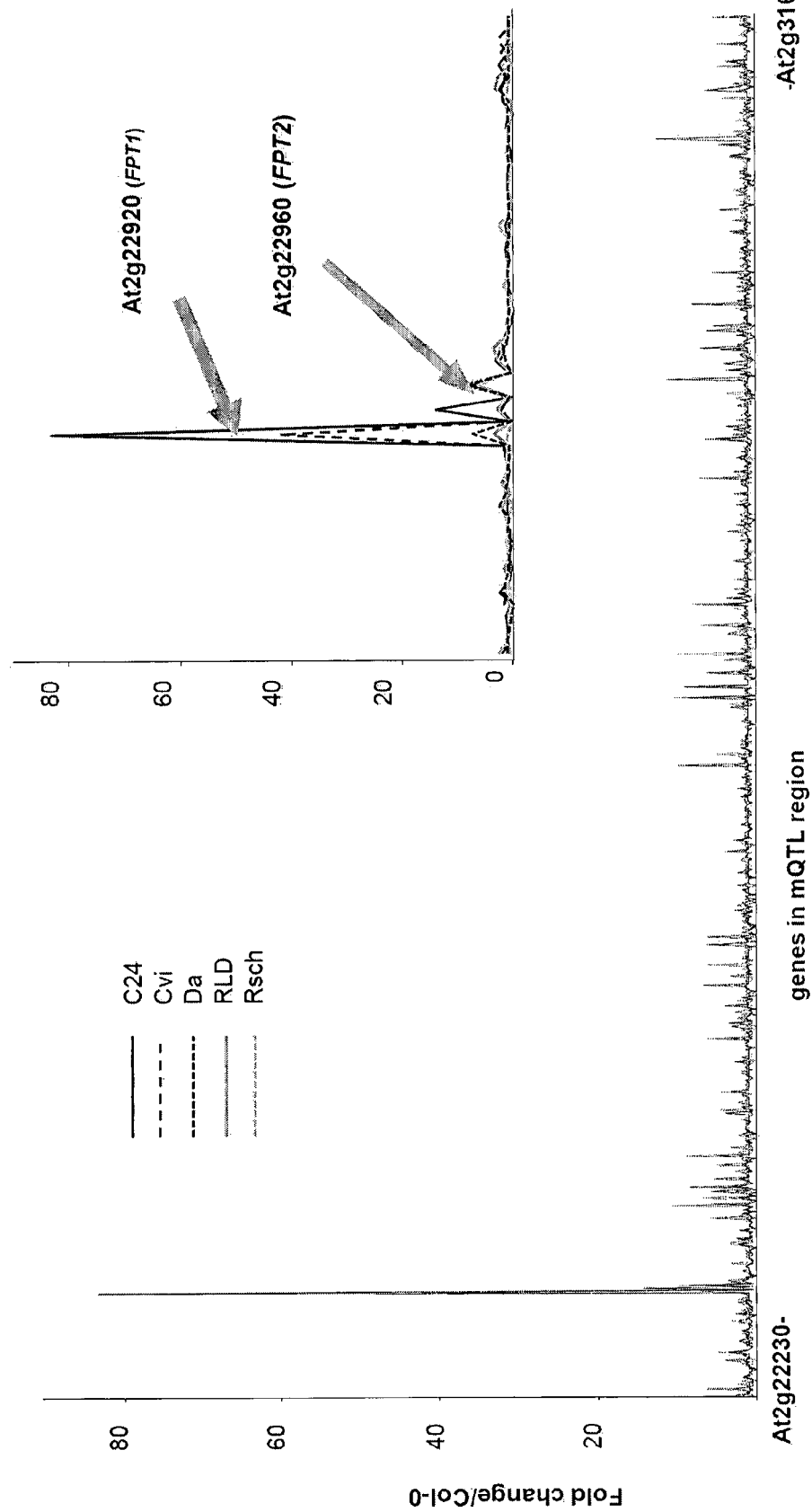
FIG. 7: shows a microarray analysis of gene expression of the genes encoded in the genomic region of chromosome 2 encoding the mQTL in five producing accessions (C24, Cvi, Da, Rsch and RLD) and five non-producing accessions (Col0, La-er, Ws, Sap and Stw). Duplicate hybridisations were carried out for Col0 and C24 for all other accessions a single hybridization was performed. Intensity indicates fold change compared to the expression level in Col0.
Figure 7:
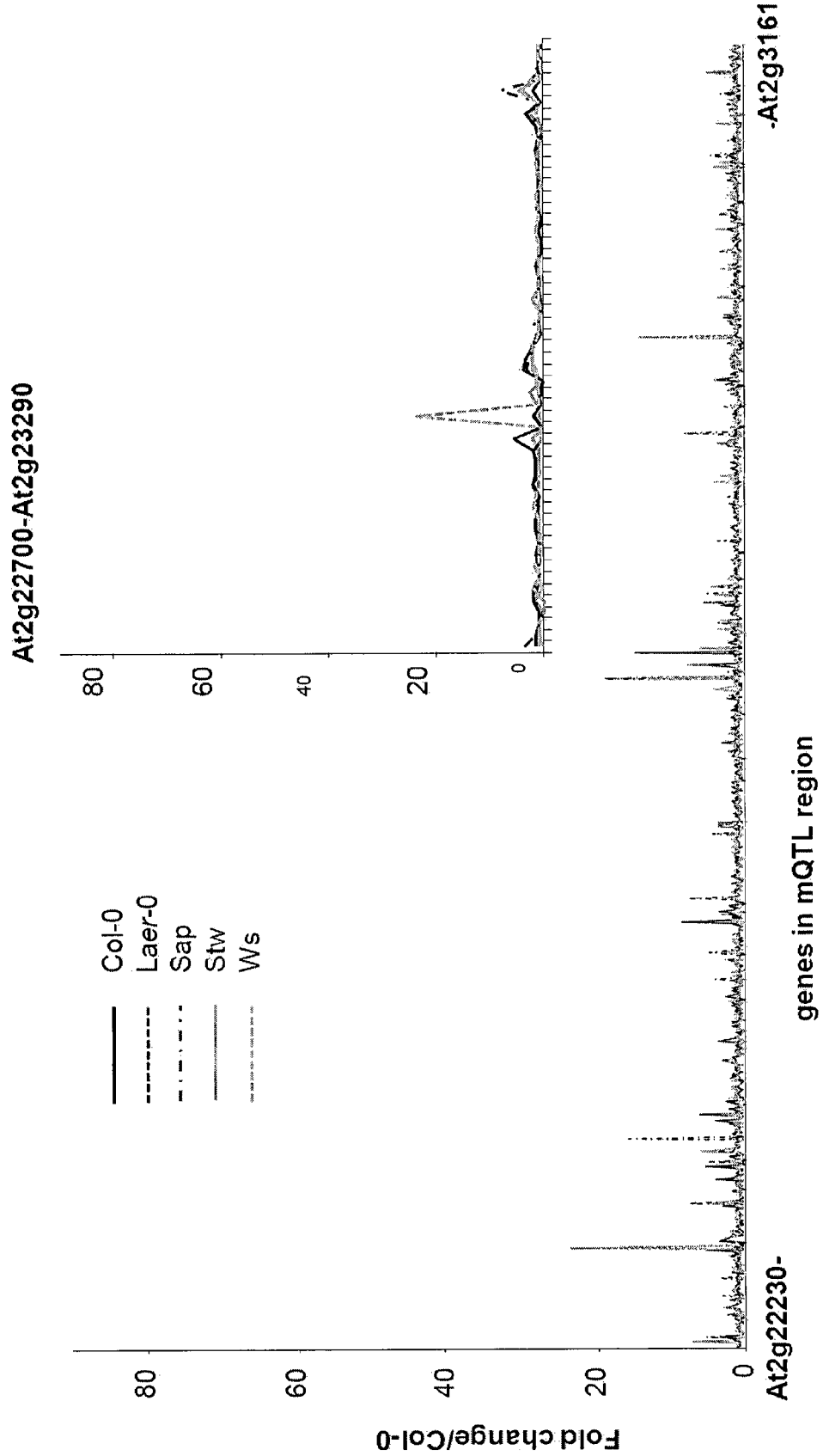

As a result, the expression levels were generally very similar between the genotypes although a number of genes were significantly different between producing and non-producing accessions including several transposable elements. However, only two genes were dramatically altered between Col0 and C24, whereas the remaining 827 genes, which were localized to the chromosomal segment of interest exhibited regular expression (see FIG. 7). The genes altered in their expression between Col0 and C24 were renamed as putative flavonol phenylacyltransferases 1 and 2 (FPT1 and FPT2). The gene transcripts for FPT1 and FPT2 were more than 17.7fold and 6.7fold higher in accession C24 than in accession Col0.

Example 7: Cloning of Full-Length cDNA of FPT1 and FPT2 Genes from Col0 and C24 *Arabidopsis*

The C24 and Col0 alleles of both genes (FPT1 and FPT2) were cloned and the transcript production was evaluated. For this, first the total RNA was extracted from frozen plant materials (see above) of both accessions Col0 and C24 by using the RNeasy Plant Mini Kit (Qiagen©) according to the manufacturer's instructions.

The mRNA contained in the total RNA that was used as template, was transcribed into oligo(dT)-primed cDNA by using using SuperScript III Reverse Transcriptase (Invitrogen©, Germany) according to the manufacturer's protocol. After digestion of the remaining RNA by an RNase H treatment, $\frac{1}{10}$ of the cDNA reaction volume was used for PCR with gene-specific primers for FPT2 (SEQ-ID No. 5 & 6) or with gene-specific primers for FPT1 (SEQ-ID No. 19 & 20).

The obtained PCR products were purified, cloned into a bacterial vector, transformed into *E. coli*, expressed in *E. coli* and purified. A cDNA segment was subcloned into GATEWAY pENTR Dual Selection vector (Invitrogen©, Germany). Then, 50 ng of the resulting plasmid expressing are mixed with 50 µl of *Escherichia coli* One Shot® TOP10 Chemically Competent *E. coli* cells (Invitrogen©, Germany) and incubated on ice for 10 min. The mix is subsequently heated to 42° C. for 45 seconds followed by 5 min incubation in ice. 1 ml of Lysogeny Broth (LB) medium is added before incubation at 37° C. for 1h. Bacteria transformed in such a way are then plated on LB-agar plates containing 50 µg/ml of kanamycin for selection of positive clones. A positive clone was grown in LB medium over night. Afterwards the cells were pelleted and the expressed plasmids containing the cloned cDNA fragment were isolated using the kit NucleoSpin Plasmid (Macherey-Nagel, Germany). Finally, the fragments were sequenced.

As a result, FPT1 transcript was invariant between Col0 and C24 (see SEQ-ID No. 3). However, the FPT2-Col0 allele encoded four different transcripts: FPT2-1(Col0) (737 bp in length, SEQ-ID No. 7), FPT2-2(Col0) (651 bp in length, SEQ-ID No. 8), FPT2-3(Col0) (631 bp in length, SEQ-ID No. 9) and FPT2-4(Col0) (560 bp in length, SEQ-ID No. 10). In contrast, FPT2-C24 encoded a single but considerably longer transcript (1305 bp, see SEQ-ID No. 1).

Example 8: Genomic Sequence of FPT2 Gene in *Arabidopsis* Accessions

Primers used for amplification and sequencing of FPT2 are described below. Four primer sets for both producing/ non-producing accessions, two primer sets for only producing accessions were used. DNA fragments amplified by sets of primers were sequenced by ABI PRISM® 3700 Genetic Analyzer (Applied Biosystems, USA)

| Set | Forward Primer | Reverse Primer |
|---|---|---|
| 1 | TGGACTAGTACGAGAATTGCAAAG (TT1f v2F; SEQ-ID No. 11) | ACCGGGAAGAAACTTGACGA (TT1f v2R; SEQ-ID No. 12) |
| 2 | CGTGGAGCGACCAGTGAT (TT2f v4F; SEQ-ID No. 13) | CTTCACGTACCCTCTCGTCA (TT2f v4R; SEQ-ID No. 14) |
| 3 | CTTATGCAGGGCTACCACAGT (TT3f v2F; SEQ-ID No. 15) | ACCACTGTTTACCAAAAACCGC (TT3f v2R; SEQ-ID No. 16) |
| 4 | ATATCATATGAATAACAGCATC (TT4f v1F; SEQ-ID No. 17) | GCATAGGGCATCATCATCTC (TT4f v1R; SEQ-ID No. 18) |

Genomic sequence analyses of FPT2 revealed a large gene deletion (~2279 bp) in Col0, spanning the region corresponding to the second to tenth exons of FPT2-C24. This analysis indicated that the four transcripts of FPT2-Col0 described above (see Example 6) are alternative splicing variants.

Example 9: Overexpression of FPT2 and FPT1 in Col0 Plants

In order to experimentally test the function of FPT1 and FPT2 in vivo, the inventors performed complementation assays in Col0 accessions by introducing an expression vector containing one of the transcripts described in Example 6 and over-expressing these transcripts.

FPT1(Col0) and FPT1(C24), indicate FPT1 cloned from Col0 and C24, respectively.

FPT2-1(Col0), FPT2-2(Col0) and FPT2(C24) indicate FPT2 cloned from Col0 (FPT2-1 is shortest transcript and FPT2-2 is longest transcript) and C24, respectively.

A cDNA segment was subcloned into GATEWAY pK2GW7 vector (Invitrogen©, Germany). Then, obtained plasmids were transformed to *Agrobacterium tumefaciens* strain GV3101 pmp 90. Positive clones, which were checked by kanamycin selection, were suspended in 20 µl of sterile water and plated out on YEB petridishes with gentamycin (25 mg/l), rifampicin (100 mg/l) and the bacterial resistance marker kanamycin (50 mg/l). After incubation for 48 hours at 28° C., the solution was mixed with transformation medium (5% sucrose medium) for flower dipping transformation. T1 seedling plants have been selected by MS-agar plates (Murashige-Skoog-Medium agar plates) containing 50 µg/ml of kanamycin for selection of positive clones. These antibiotics selection were repeated for T2 and T3 generation seedling to obtain T3 homozygote transgenic plants.

In order to determine the saiginol production in the transformed plants, flower and leaf materials of Col-0, NIL N09, tt4 mutant and transgenic lines (FPT2(C24)-OX, FPT2-1(Col0)-OX, FPT1(C24)-OX) were harvested for saiginol profile by chromatographic methods as described previously.

Figure 8:
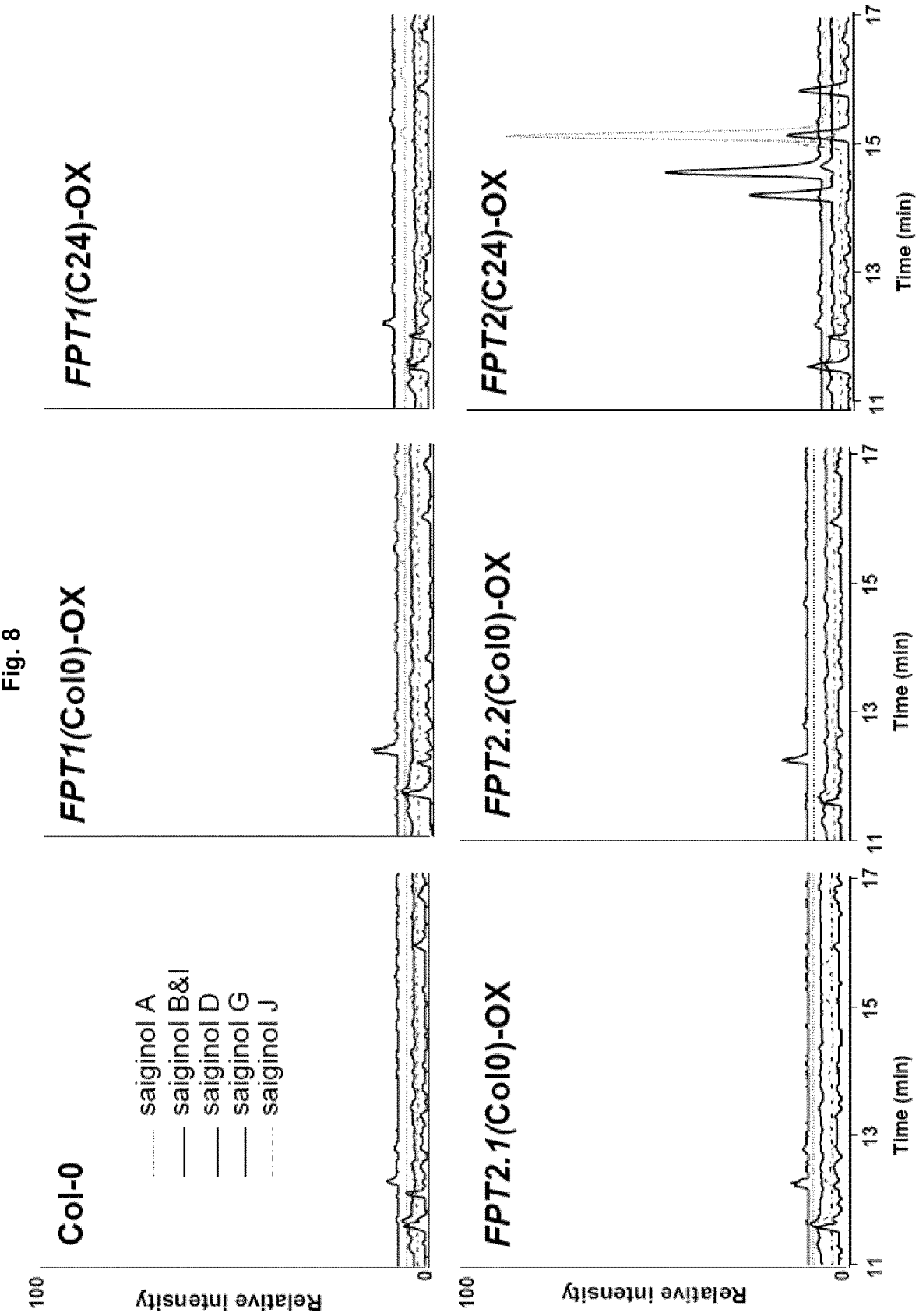
FIG. 8: In vivo functional characterization of FPT1 and 2 by metabolite profiling of transgenic plants.

As a result, overexpression of FPT1, irrespective if derived from C24 (FPT1(C24)) or Col0 (FPT1(Col0)), did not lead to a production of saiginols in Col0 plants (see FIG. 8) The same result was obtained for the overexpression of the shortest transcript (FPT2-1(Col0)), or the longest transcript (FPT2-2(Col0)) of FPT2 derived from Col0 (FIG. 8). Only the overexpression of FPT2 derived from C24 (FPT2 (C24)) led to the production of saiginols in the otherwise non-producing accession Col0 (FIG. 8).

Example 10: UV-B Irradiation Experiment

In order to test the effect of saiginol production with respect to UV-B irradiation in vivo, the following plants were tested in this experiment:

(1) Col0 as a representative for a non-producing accession (2) NIL N09—the gain-of-function line (C24 donor, Col0 background, Example 5)

(3) FPT2(C24)-OX—transgenic Col0 plant overexpressing FPT2(C24) (Example 8)

(4) FPT2-1(Col0)-OX—transgenic Col0 plant overexpressing FPT2-1(Col0) (Example 8)

(5) FPT1 (C24)-OX—transgenic Col0 plant overexpressing FTP1(C24) (Example 8)

(6) tt4—a mutant *Arabidopsis* line lacking flavonoids

Plants were cultured on agar plate in a growth chamber under normal long day light conditions (16 h day, 140-160 µmol photons $m^{-2} s^{-1}$, 20° C.; 8 h night, 16° C.) for 14 days and transferred to soil.

One week after transferring the plants to the soil and before plant bolting, plants were started to be irradiated with UV-B light in addition to the normal light regimen. UV-B light was irradiated 2h per day during midday time (stated 5-7h after starting normal light). The intensities of UV-B light tested in two trials were 1000 mW/m² and 2000 mW/m².

After bolting of the plants, the seeds were collected and both the seed yield and the seed germination rate were determined using 2 weeks old seedling.

The seed yield was calculated as ratio between the seed yield (in mg) of an UV-B radiated plant and the seed yield (in mg) of a control plant without additional UV-B irradiation.

Not surprisingly, the flavonoid less tt4 mutant line was especially prone to UV-B irradiation and showed the lowest seed yield and seed germination rate (FIG. 9b, c).

The seed yield of the non-producing accession Col0 was reduced in comparison to not UV-B irradiated Col0 plants, especially with higher UV-B intensity (FIG. 9b). The Col0 lines overexpressing FPT1(C24) or FPT2-1(Col0) were indistinguishable from regular Col0 (FIG. 9b).

However, the seed yield in the gain-of-function line NIL N09 and the Col0 line overexpressing FPT2(C24) was considerably higher compared to normal Col0 plants (FIG. 9b). Moreover, the germination rate of the seeds was also doubled in NIL N09 and FPT2(C24)-OX compared to Col0 (FIG. 9c), revealing that the production of germinable seeds was almost five times higher in the gain-of-function (NIL N09) line and the C24-FPT2 overexpressing line than in lines that do not produce the inventive saiginols.

In addition, the vitality of the NIL N09 gain-of-function line and the FPT2-C24 overexpressing line was reflected in the number of leaves and inflorescences these lines produced compared to Col0 and tt4 (FIG. 9a). Moreover, NIL N09 and FPT2-C24 overexpressing line was considerably larger than tt4.

For silique production experiment (result shown in FIG. 10), inflorescences from the primary bolts of 5-week-old *Arabidopsis* plants were used. The detached inflorescences were irradiated with UV-B light (1 W m2) for 2 h per day during midday time (5-7 h after the onset of normal light) for 14 days by placing their cut ends in wells of a 96-well microtiter plate containing water.

Example 11: Sunscreen Formulation

A suitable sunscreen composition contains the following components with listed percentages based on total weight of the composition:

Active Ingredients:

titanium oxide (20.0%), saiginol A (7.5%),

Inactive Ingredients:

ethanol (59.9%), hyaluronic acid (2.5%), grape seed oil (5.0%), sesame oil (2.5%), sunflower seed oil (2.5%), and tetrahexyldecyl ascorbate (0.1%).

Example 12: Transformation of Tobacco and Tomato Plants

A cDNA segment was subcloned into GATEWAY pK2GW7 vector (Invitrogen©, Germany). Then, obtained plasmids were transformed to *Agrobacterium tumefaciens* strain GV2260 pmp 90. Positive clones, which were checked by spectinomycin selection, were suspended in 20 µl of sterile water and plated out on YEB petridishes with gentamycin (25 mg/l), rifampicin (100 mg/l) and the bacterial resistance marker spectinomycin (50 mg/l). After incubation for 24 hours at 28° C., the solution was mixed with transformation medium (5% sucrose medium) for transformation. Tobacco or tomato leaf disc (1×1 cm) which was injured by metal blade was used for injection. After dipping into *agrobacterium* solution, leaf discs were incubated on MS-agar plate for 48 h under darkness. After this treatment, leaf disc has been transferred to MS-agar plate (Murashige-Skoog-Medium agar plates) containing 50 µg/ml of kanamycin for selection of positive clones and 6-Benzylaminopurine (BAP) and indole-3-acetic acid (IAA) for induction of callus root.

Example 13: Secondary Metabolite Profiling of Transgenic Tobacco Plants by LC-MS Application of liquid chromatographyÐmass spectrometry (LC-MS) using the method described in Example 2 resulted in the detection of a total of 3 peaks annotated as putative phenyacylated flavonol-glycosides in tobacco. All data were processed using Xcalibur 2.1 software (Thermo Fisher Scientific, Waltham, USA). This result indicates that FPT2 gene can be employed to metabolic engineering in other plant species. Since function of FPT2 has a broader function with lower substrate specificity, it can be used to transform other plant species than *Arabidopsis* and improve their UV-B resistance.

SEQUENCE LIST
SEQ-ID No. 1: cDNA of C24 FPT2
ATGAGAACTTTTTCACCCAAGTTGCTGCTTCTTCTTTTACTTGTTTTAAGACATCATGCTGAATCTGGCTCTA

TCGTCAAGTTTCTTCCCGGTTTTGAAGGCCCTCTTCCTTTCGAACTTGAAACCGGGTACATCGGTATTGGTGA

AGAAGAAGAACTGCAATCGTTTTACTATTTCATTAAGTCTGAGAAGAATCCAAAAGAAGATCCTCTTCTTCTT

TGGATATCTGGAGGACCTGGTTGCTCTTCTATTTCTGCTCTTCTTTTGAGAATGGACCTGTGGCTCTAAAGT

TCGAGGTTTACAATGAAACTCTCCCTTATTTGGTCTCTACTACATATTCATGGACCAAGATGACGAACGTATT

ATTCTTGGATCAGCCTATTGGAGTTGGCTTCTCCTACAAAAGAACTCCAAATCTTGATAAATCGAGTGACACA

ATAGAAGTATTGCGGATATACGAATTTCTTCAGAAGTGGCTAGGTGAACATCCTGAGTTTTTCTCCAACACTT

TTTACGTAGGAGGAGATTCTTATTCCGGTAAGATTGTTCCAGCTATCGTTGATAAAATCTCACAAGAAAATTA

TTTGTGCTGCAAACCTCCAATAAATCTTCAGGGTTATGTTCTCGGAAACCCAATAACAAATTTGGAATCTGAT

TCTAACTATCGTATTCCATATGCTCATGGAATGGCATTAATTTCTGATGAGCTCTACGAATCCCTGAAGAGAA

ACTGCAAAGGAAGATATAAACCGTGGATCCATCTAACAAAAAATGTTTGAACTTGTTGAAAAATACAATAA

GTGTTCTGATAAAATATTTAGAGAACTAATATTATTACCACAGTGTGATGAAAGATCTCCACTCTGCTGGGGC

TACCACAGTACACTAGCTAAATATTGGGCCAATGACGAGAGGGTACGTGAAGCTCTTCAAATAAGAAAGGGAA

GTATAGGAAAATGGATACGATGTAATACGAATATACATTACGGTGACGACATTATTAGCAGCATACCATATCA

TATGAATAACAGCATCAACGGATACCGATCTCTCATTTACAGTGGTGATCACGATATGGAGGTACCTTTCCTT

GCAACTGAAGCTTGGATAAGATCTCTCAATTATCCTATTATTGATGATTGGAGGCCTTGGATAATAAACAATC

AGATTTCAGGATACACGATGACCTATGCCAATAAGATGACATATGCTACTATCAAGGGAGGTGGACACACTGC

AGAGTATAAACCAGCGGAGAGCTTTATCATGTTCCAACGATGGATCAGTGGCCAGTCTCTGTAA

SEQ-ID No. 2: amino acid sequence coded by SEQ-ID No. 1
MRTFSPKLLLLLLLVLRHHAESGSIVKFLPGFEGPLPFELETGYIGIGEEEELQSFYYFIKSEKNPKEDPLLL

WISGGPGCSSISALLFENGPVALKFEVYNETLPYLVSTTYSWTKMTNVLFLDQPIGVGFSYKRTPNLDKSSDT

IEVLRIYEFLQKWLGEHPEFFSNTFYVGGDSYSGKIVPAIVDKISQENYLCCKPPINLQGYVLGNPITNLESD

SNYRIPYAHGMALISDELYESLKRNCKGRYKTVDPSNKKCLKLVEKYNKCSDKIFRELILLPQCDERSPLCWG

YHSTLAKYWANDERVREALQIRKGSIGKWIRCNTNIHYGDDIISSIPYHMNNSINGYRSLIYSGDHDMEVPFL

ATEAWIRSLNYPIIDDWRPWIINNQISGYTMTYANKMTYATIKGGGHTAEYKPAESFIMFQRWISGQSL

SEQ-ID No. 3: cDNA of C24 FPT1
ATGAAATCAACACTAAAATTGCTGCTTCTGCTTCTGTTTATGTTAAACCATCATGTTGATTCTGGCTCTATCG

TCAAGTTTCTTCCCGGCTTTGAAGGCCCTCTTCCTTTCGAACTCGAAACCGGGTACATTGGTATTGGTGAGGA

AGAGGAAGTACAGTTGTTCTACTACTTTATAAAGTCTGAGAGAAATCCAAAAGAAGACCCTCTTCTTCTCTGG

TTAAGTGGAGGACCTGGATGTTCATCTATCACTGGCCTTCTTTTCGAGAATGGACCTTTGGCTTTGAAGTCCG

AGGTTTACAATGGAAGTGTCCCTTCTTTGGTCTCTACTACATATTCGTGGACAAAGACGGCGAACATAATATT

CTTGGATCAGCCTATTGGAGCTGGCTTCTCCTACTCAAGAATCCCACTTATTGATACGCCTAGTGACACAGGC

GAAGTTAAGAATATCCATGAGTTTCTCCAAAAGTGGTTAAGCAAGCATCCACAGTTTTCTTCCAATCCTTTCT

ATGCTAGCGGAGATTCTTATTCCGGTATGATTGTTCCAGCCCTCGTTCAAGAAATTTCGAAAGGAAATTATAT

ATGTTGCAAACCTCCTATAAATCTACAGGGCTATATACTCGGGAACCCAATAACATATTTTGAAGTCGACCAA

AACTATCGCATTCCATTTTCTCATGGAATGGCACTTATTTCAGATGAACTATACGAGTCAATTAGGAGAGACT

GCAAAGGAAATTATTTCAACGTGGATCCACGTAACACAAAATGTTTGAAACTTGTTGAAGAATACCATAAGTG

TACCGACGAACTAAATGAATTCAATATATTATCACCAGATTGCGACACGACATCTCCTGATTGCTTTGTATAT

CCATATTATCTCCTTGGCTACTGGATCAACGACGAGAGCGTTCGCGATGCTCTTCATGTTAATAAGAGCAGTA

TTGGAAAATGGGAGCGATGTACTTATCAAAATAGAATCCCATACAACAAAGACATCAATAACAGCATACCATA

CCATATGAATAACAGTATTAGTGGCTACCGATCTCTCATCTACAGTGGTGATCATGATTTGGTGGTTCCTTTC

-continued

CTTGCAACTCAAGCCTGGATAAAATCTCTAAATTACTCCATCATTCATGAATGGAGACCTTGGATGATTAAAG

ATCAAATCGCTGGGTATATAATATATTTTTGTGTTATACACGAGAACTTATTCCAATAA

SEQ-ID No. 4: amino acid sequence coded by SEQ-ID No. 3
MKSTLKLLLLLLFMLNHHVDSGSIVKFLPGFEGPLPFELETGYIGIGEEEEVQLFYYFIKSERNPKEDPLLLW

LSGGRGCSSITGLLFENGPLALKSEVYNGSVPSLVSTTYSWTKTANIIFLDQPIGAGFSYSRIPLIDTRSDTG

EVKNIHEFLQKWLSKHPQFSSNPFYASGDSYSGMIVPALVQEISKGNYICCKPPINLQGYILGNPITYFEVDQ

NYRIPFSHGMALISDELYESIRRDCKGNYFNVDPRNTKCLKLVEEYHKCTDELNEFNILSPDCDTTSPDCFVY

PYYLLGYWINDESVRDALHVNKSSIGKWERCTYQNRIPYNKDINNSIPYHMNNSISGYRSLIYSGDHDLVVPF

LATQAWIKSLNYSIIHEWRPWMIKDQIAGYIIYFCVIHENLFQ

SEQ-ID No. 5: forward primer for amplification of FPT2 cDNA (At2g22980)
ATGAGAACTTTTTCACCCAAGTT SEQ-ID No. 6: reverse primer for amplification of FPT2 cDNA (At2g22960)
TCATCATCTCTTATTATTACAGA SEQ-ID No. 7: cDNA of Col0 FPT2-1
ATGAGAACTTTTTCACCCAAGTTGCTGCTTCTTCTTTTACTTGTTTTAAGACATCATGCTGAATCTGGCTCTA

TCGTCAAGTTTCTTCCCGGTTTTGAAGGCCCTCTTCCTTTCGAACTTGAAACCGGGGCTACCACAGTACACTA

GCTAAATATTGGGCCAATGACGAGAGGGTACGTGAAGCTCTTCAAATAAGAAAGGGAAGTATAGGAAAATGGA

TACGATGTAATTCGAATATACATTACGATGACGACATTATTAGCAGCATACCATATCATATGAATAACAGCAT

CAACGGATACCGATCTCTTATTTACAGGTTTGATTAAAATTACATTTTAAAGAATCGATCTAGTTCTCTATAC

AAACTATGCGGTTTTTGGTAAACAGTGGTGATCACGATATGGAGGTACCTTTCCTTGCAACTGAAGCTTGGAT

AAGATCTCTTAATTATCCTATTATTGATGATTGGAGGCCTTGGATAATAAACAATCAGATTGCTGGGTGAATA

ATTTTTACAATTTTTTTTTTGCTTCTTTATTCATTAACTCAGTCGAATCATGAGCTCATTAGTCATTTTGAA

ATCCCTCTTACGATTTTCTTGGACAGATACACGATGACCTATGCCAATAAGATGACATATGCTACTATCAAGG

GAGGTGGACACACTGCAGAGTATAAACCAGCGGAGAGCTTTATCATGTTCCAACGATGGATCAGTGGCCAGCC

TCTGTAA

SEQ-ID No. 8: cDNA of Col0 FPT2-2
ATGAGAACTTTTTCACCCAAGTTGCTGCTTCTTCTTTTACTTGTTTTAAGACATCATGCTGAATCTGGCTCTA

TCGTCAAGTTTCTTCCCGGTTTTGAAGGCCCTCTTCCTTTCGAACTTGAAACCGGGGCTACCACAGTACACTA

GCTAAATATTGGGCCAATGACGAGAGGGTACGTGAAGCTCTTCAAATAAGAAAGGGAAGTATAGGAAAATGGA

TACGATGTAATTCGAATATACATTACGATGACGACATTATTAGCAGCATACCATATCATATGAATAACAGCAT

CAACGGATACCGATCTCTTATTTACAGTGGTGATCACGATATGGAGGTACCTTTCCTTGCAACTGAAGCTTGG

ATAAGATCTCTTAATTATCCTATTATTGATGATTGGAGGCCTTGGATAATAAACAATCAGATTGCTGGATACA

CGATGACCTATGCCAATAAGATGACATATGCTACTATCAAGGCAAGTTTTTTTTTTTGTTCTTACTCTTAAT

GTTTTTTATTACACAAATCATTTTGTTTCTCAGTAACTGTTTTGAGGGGTTTACTATAGGGAGGTGGACACAC

TGCAGAGTATAAACCAGCGGAGAGCTTTATCATGTTCCAACGATGGATCAGTGGCCAGCCTCTGTAA

SEQ-ID No. 9: cDNA of Col0 FPT2-3
ATGAGAACTTTTTCACCCAAGTTGCTGCTTCTTCTTTTACTTGTTTTAAGACATCATGCTGAATCTGGCTCTA

TCGTCAAGTTTCTTCCCGGTTTTGAAGGCCCTCTTCCTTTCGAACTTGAAACCGGGGCTACCACAGTACACTA

GCTAAATATTGGGCCAATGACGAGAGGGTACGTGAAGCTCTTCAAATAAGAAAGGGAAGTATAGGAAAATGGA

TACGATGTAATTCGAATATACATTACGATGACGACATTATTAGCAGCATACCATATCATATGAATAACAGCAT

CAACGGATACCGATCTCTTATTTACAGGTTTGATTAAAATTACATTTTAAAGAATCGATCTAGTTCTCTATAC

AAACTATGCGGTTTTTGGTAAACAGTGGTGATCACGATATGGAGGTACCTTTCCTTGCAACTGAAGCTTGGAT

AAGATCTCTTAATTATCCTATTATTGATGATTGGAGGCCTTGGATAATAAACAATCAGATTGCTGGATACACG

-continued

ATGACCTATGCCAATAAGATGACATATGCTACTATCAAGGGAGGTGGACACACTGCAGAGTATAAACCAGCGG

AGAGCTTTATCATGTTCCAACGATGGATCAGTGGCCAGCCTCTGTAA

SEQ-ID No. 10: cDNA of Co10 FPT2-4
ATGAGAACTTTTTCACCCAAGTTGCTGCTTCTTCTTTTACTTGTTTTAAGACATCATGCTGAATCTGGCTCTA

TCGTCAAGTTTCTTCCCGGTTTTGAAGGCCCTCTTCCTTTCGAACTTGAAACCGGGGCTACCACAGTACACTA

GCTAAATATTGGGCCAATGACGAGAGGGTACGTGAAGCTCTTCAAATAAGAAAGGGAAGTATAGGAAAATGGA

TACGATGTAATTCGAATATACATTACGATGACGACATTATTAGCAGCATACCATATCATATGAATAACAGCAT

CAACGGATACCGATCTCTTATTTACAGTGGTGATCACGATATGGAGGTACCTTTCCTTGCAACTGAAGCTTGG

ATAAGATCTCTTAATTATCCTATTATTGATGATTGGAGGCCTTGGATAATAAACAATCAGATTGCTGGATACA

CGATGACCTATGCCAATAAGATGACATATGCTACTATCAAGGGAGGTGGACACACTGCAGAGTATAAACCAGC

GGAGAGCTTTATCATGTTCCAACGATGGATCAGTGGCCAGCCTCTGTAA

SEQ-ID No. 11: forward primer of set 1 for amplification of FPT2 genome
sequence
TGGACTAGTACGAGAATTGCAAAG SEQ-ID No. 12: reverse primer of set 1 for amplification of FPT2 genome
sequence
ACCGGGAAGAAACTTGACGA SEQ-ID No. 13: forward primer of set 2 for amplification of FPT2 genome
sequence
CGTGGAGCGACCAGTGAT SEQ-ID No. 14: reverse primer of set 2 for amplification of FPT2 genome
sequence
CTTCACGTACCCTCTCGTCA SEQ-ID No. 15: forward primer of set 3 for amplification of FPT2 genome
sequence
CTTATGCAGGGCTACCACAGT SEQ-ID No. 16: reverse primer of set 3 for amplification of FPT2 genome
sequence
ACCACTGTTTACCAAAAACCGC SEQ-ID No. 17: forward primer of set 4 for amplification of FPT2 genome
sequence
ATATCATATGAATAACAGCATC SEQ-ID No. 18: reverse primer of set 4 for amplification of FPT2 genome
sequence
GCATAGGGCATCATCATCTC SEQ-ID No. 19: forward primer for amplification of FPT1 cDNA
(At2g22920)
ATGAAATCAACACCAAAAT SEQ-ID No. 20: reverse primer for amplification of FPT1 cDNA
(At2g22920)
ATTTAGGTAAGGTCATTCAAGTA SEQ-ID No. 21: amino acid (aa) sequence of a variant of BLOCK 1
GPGCSSxxxL (x = random amino acid)

SEQ-ID No. 22: amino acid (aa) sequence of a variant of BLOCK 2
GDSYSG

---

The invention claimed is:

1. A transgenic UV-B tolerant *Arabidopsis* plant cell, *Arabidopsis* plant tissue or *Arabidopsis* plant comprising an exogenous nucleic acid molecule consisting of the cDNA encoding a flavonol phenylacyltransferase 2 protein having at least 95% sequence identity to SEQ-ID NO:2, wherein said exogenous nucleic acid molecule has been introduced by genetic manipulation into a plant that does not naturally express said nucleic acid molecule, wherein said exogenous nucleic acid molecule is operably linked to a promoter, wherein said transgenic plant cell, plant tissue or plant has enhanced tolerance to UV-B irradiation relative to a native plant cell, plant tissue or plant of the same species that does not naturally express said nucleic acid molecule, and wherein said enhanced UV-B tolerance is assessed after UV-B irradiation treatment for at least 2 hours per day for 28 days with 2000 mW/m$^2$.

2. The transgenic UV-B tolerant plant cell, plant tissue or plant according to claim 1, wherein said flavonol phenylacyltransferase 2 protein synthesizes a compound of general formula (I)

(I)

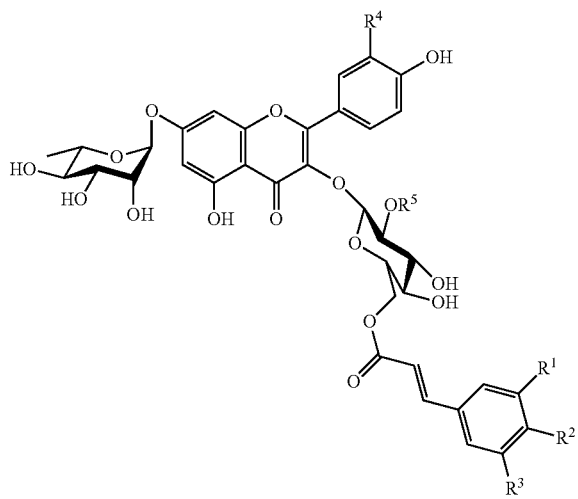

wherein
R¹, R² and R³ are independently of each other selected from: —H, —OH, and —OCH₃;
R⁴ is selected from —H, —OH, and —OCH₃;
R⁵ represents —H,

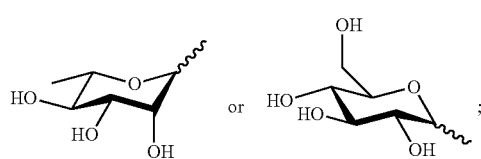

and enantiomers, mixtures of enantiomers, diastereoisomers, mixtures of diastereoisomers, hydrates and solvates thereof.

3. The transgenic UV-B tolerant plant cell, plant tissue or plant according to claim 1, wherein said flavonol phenylacyltransferases 2 protein synthesizes a compound of general formula (II)

(II)

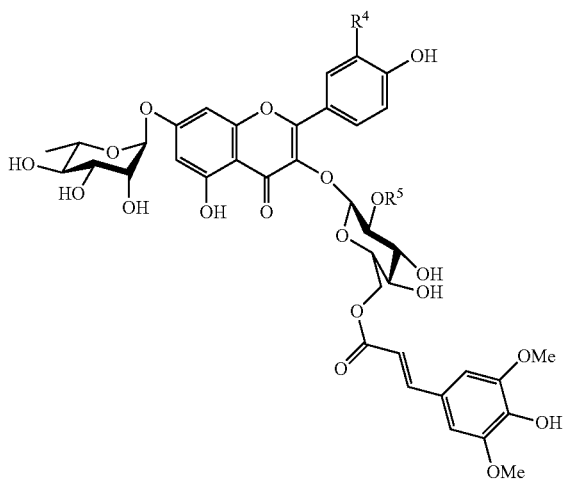

wherein
R⁴ is selected from —H, —OH, and —OCH₃;
R⁵ represents —H or

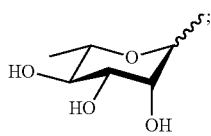

and enantiomers, mixtures of enantiomers, diastereoisomers, mixtures of diastereoisomers, hydrates and solvates thereof.

4. The transgenic UV-B tolerant plant cell, plant tissue or plant according to claim 1, wherein said flavonol phenylacyltransferases 2 protein synthesizes a compound of general formula (III)

(III)

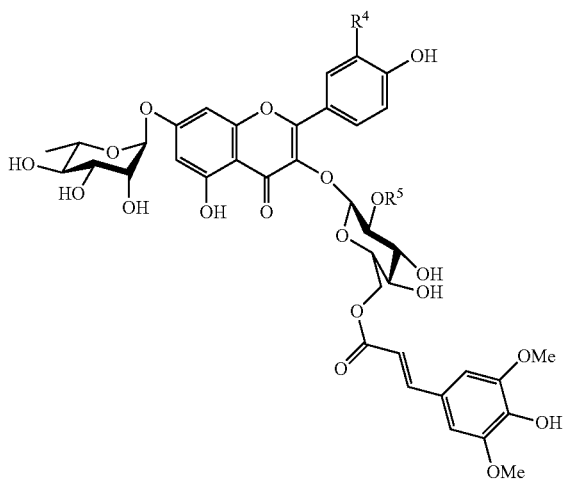

wherein
R⁴ is selected from —H, —OH, and —OCH₃;
R⁵ represents —H or

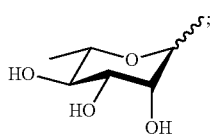

and enantiomers, mixtures of enantiomers, diastereoisomers, mixtures of diastereoisomers, hydrates and solvates thereof.

5. The transgenic UV-B tolerant plant cell, plant tissue or plant according to claim 1, wherein said flavonol phenylacyltransferases 2 protein synthesizes a compound of general formula (IV)

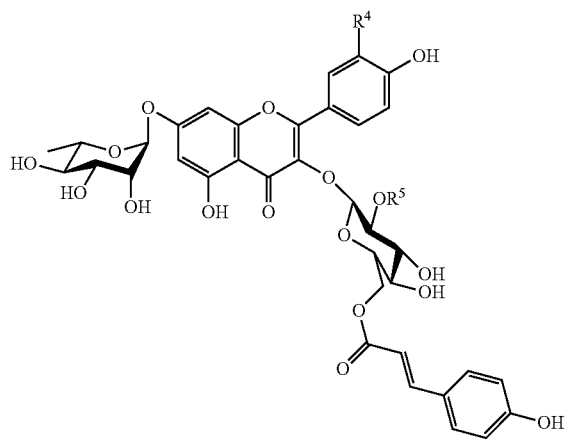

(IV)

wherein
$R^4$ is selected from —H, —OH, and —OCH$_3$;
$R^5$ represents —H or

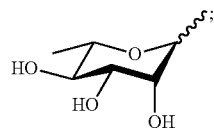

and enantiomers, mixtures of enantiomers, diastereoisomers, mixtures of diastereoisomers, hydrates and solvates thereof.

6. The transgenic UV-B tolerant plant cell, plant tissue or plant according to claim 1, wherein said flavonol phenylacyltransferases 2 protein synthesizes a compound selected from the group consisting of Saiginol A*, Saiginol B*, Saiginol C*, Saiginol G*, Saiginol H*, Saiginol I*, Saiginol M*, Saiginol N*, Saiginol O*, Saiginol A, Saiginol B, Saiginol C, Saiginol D, Saiginol E, Saiginol F, Saiginol G, Saiginol H, Saiginol I, Saiginol J, Saiginol K, Saiginol L, Saiginol M, Saiginol N, Saiginol O, Saiginol P, Saiginol Q, and Saiginol R.

7. The transgenic UV-B tolerant plant cell, plant tissue or plant according to claim 1, wherein said exogenous nucleic acid molecule consists of a cDNA encoding a flavonol phenylacyltransferase 2 protein, wherein said nucleic acid molecule has at least 95% sequence identity to SEQ-ID NO:1.

* * * * *